(12) United States Patent
Desimone et al.

(10) Patent No.: US 10,792,857 B2
(45) Date of Patent: Oct. 6, 2020

(54) POLYMERIC MICRONEEDLES AND RAPID ADDITIVE MANUFACTURING OF THE SAME

(71) Applicant: The University of North Carolina at Chapel Hill, Chapel Hill, NC (US)

(72) Inventors: Joseph M. Desimone, Monte Sereno, CA (US); Gregory R. Robbins, Redwood City, CA (US); Ashley R. Johnson, Coppell, TX (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 416 days.

(21) Appl. No.: 15/557,003

(22) PCT Filed: Mar. 12, 2016

(86) PCT No.: PCT/US2016/022231
§ 371 (c)(1),
(2) Date: Sep. 8, 2017

(87) PCT Pub. No.: WO2016/149152
PCT Pub. Date: Sep. 22, 2016

(65) Prior Publication Data
US 2018/0064920 A1 Mar. 8, 2018

Related U.S. Application Data

(60) Provisional application No. 62/132,990, filed on Mar. 13, 2015.

(51) Int. Cl.
*B29C 64/124* (2017.01)
*A61B 5/15* (2006.01)
(Continued)

(52) U.S. Cl.
CPC ...... *B29C 64/124* (2017.08); *A61B 5/150022* (2013.01); *A61B 5/150282* (2013.01);
(Continued)

(58) Field of Classification Search
CPC .... B29C 64/124; B29C 64/129; B29C 64/135
See application file for complete search history.

(56) References Cited

U.S. PATENT DOCUMENTS 5,236,637 A * 8/1993 Hull ............... B29C 35/08
264/401
5,391,072 A * 2/1995 Lawton ............ B29C 64/129
425/174.4
(Continued)

FOREIGN PATENT DOCUMENTS

EP 2213284 A1 8/2010
WO WO-03/015860 A1 2/2003
(Continued)

OTHER PUBLICATIONS

Kim et al., Exposure Time Variation Method Using DMD for Microstereolithography, Journal of Advanced Mechanical Design, Systems, and Manufacturing, vol. 6, No. 1, 2012. (Year: 2012).*
(Continued)

*Primary Examiner* — Atul P. Khare
(74) *Attorney, Agent, or Firm* — Ballard Spahr LLP

(57) ABSTRACT

The invention generally relates to microneedle devices, methods of making same, pharmaceutical compositions comprising same, and methods of treating a disease comprising administering same. Specifically, the disclosed microneedle devices comprise a plurality of biocompatible microneedles having one or more of: (i) a curved, discontinuous, undercut, and/or perforated sidewall; (ii) a sidewall comprising a breakable support; and (iii) a cross-section that
(Continued)

is non-circular and non-polygonal. The microneedles may also be tiered. Alternatively, the microneedles may be tiered. This abstract is intended as a scanning tool for purposes of searching in the particular art and is not intended to be limiting of the present invention.

17 Claims, 46 Drawing Sheets

(51) Int. Cl.
  *B29C 64/129* (2017.01)
  *B29C 64/135* (2017.01)
  *A61M 37/00* (2006.01)

(52) U.S. Cl.
  CPC ... *A61B 5/150984* (2013.01); *A61M 37/0015* (2013.01); *B29C 64/129* (2017.08); *B29C 64/135* (2017.08); *A61M 2037/0023* (2013.01); *A61M 2037/0046* (2013.01); *A61M 2037/0053* (2013.01)

(56) References Cited

U.S. PATENT DOCUMENTS

| | | | | |
|---|---|---|---|---|
| 9,205,601 | B2* | 12/2015 | DeSimone | B33Y 10/00 |
| 9,360,757 | B2* | 6/2016 | DeSimone | B29C 64/245 |
| 9,453,142 | B2* | 9/2016 | Rolland | C08G 18/10 |
| 9,486,964 | B2* | 11/2016 | Joyce | B29C 64/20 |
| 9,975,295 | B2* | 5/2018 | Rolland | B29C 64/205 |
| 10,155,345 | B2* | 12/2018 | Ermoshkin | B29C 64/20 |
| 10,166,725 | B2* | 1/2019 | Willis | B29C 64/277 |
| 10,538,030 | B2* | 1/2020 | DeSimone | B22C 1/22 |
| 2004/0267205 | A1* | 12/2004 | Stemme | A61M 37/0015 604/173 |
| 2008/0167601 | A1 | 7/2008 | Laermer et al. | |
| 2008/0213461 | A1* | 9/2008 | Gill | A61K 9/0021 427/2.3 |
| 2011/0028905 | A1* | 2/2011 | Takada | A61K 31/496 604/180 |
| 2011/0098651 | A1 | 4/2011 | Falo, Jr. et al. | |
| 2013/0295212 | A1* | 11/2013 | Chen | B29C 64/129 425/150 |
| 2014/0005606 | A1 | 1/2014 | Chen et al. | |
| 2015/0034007 | A1* | 2/2015 | Fischer | G03F 7/0037 118/620 |

FOREIGN PATENT DOCUMENTS

| | | |
|---|---|---|
| WO | WO-2006/138719 A2 | 12/2006 |
| WO | WO-2008/053481 A1 | 5/2008 |
| WO | WO-2012/144718 A1 | 10/2012 |
| WO | WO-2014/004301 A1 | 1/2014 |

OTHER PUBLICATIONS

Yun et al., Development of DMD-based micro-stereolithography apparatus for biodegradable multi-material micro-needle fabrication, Journal of Mechanical Science and Technology 27 (10) (2013) 2973-2978. (Year: 2013).*

Johnson et al., Single-Step Fabrication of Computationally Designed Microneedles by Continuous Liquid Interface Production, PLoS ONE 11(9): e0162518. pp. 1-17, 2016. (Year: 2016).*

Tumbleston et al., Continuous liquid interface production of 3D objects, Science vol. 347, Issue 6228, pp. 1349-1352, 2015. (Year: 2015).*

Chu, L.Y. et al: "Separable arrowhead microneedles". Journal of Controlled Release. 149(3):242-249. (2010).

International Search Report and Written Opinion dated Jun. 2, 2016 by the International Searching Authority for International Patent Application No. PCT/US2016/022231, which was filed on Mar. 12, 2016 and published as WO 2016/149152 on Sep. 22, 2016 (Applicant—The University of North Carolina at Chapel Hill) (14 pages).

International Preliminary Report on Patentability dated Sep. 19, 2017 by the International Searching Authority for International Patent Application No. PCT/US2016/022231, which was filed on Mar. 12, 2016 and published as WO 2016/149152 on Sep. 22, 2016 (Applicant—The University of North Carolina at Chapel Hill) (8 pages).

* cited by examiner $$Force_{single\,MN} = \frac{Force_{total,array}}{\#\,of\,needles} \quad (Eq1)$$

Traditional MN Array $$Force_{single\,MN} = \frac{Force_{total,array}}{\#\,of\,needles\,per\,layer} \quad (Eq2)$$

Tiered MN Array

STEP #3

STEP #4

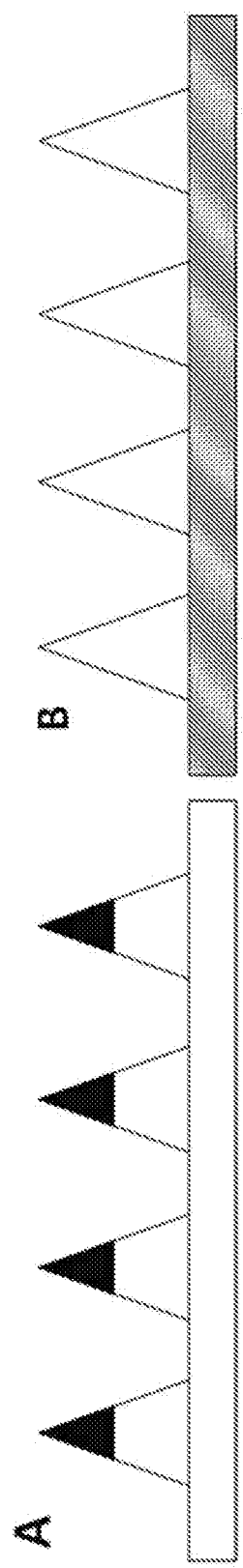
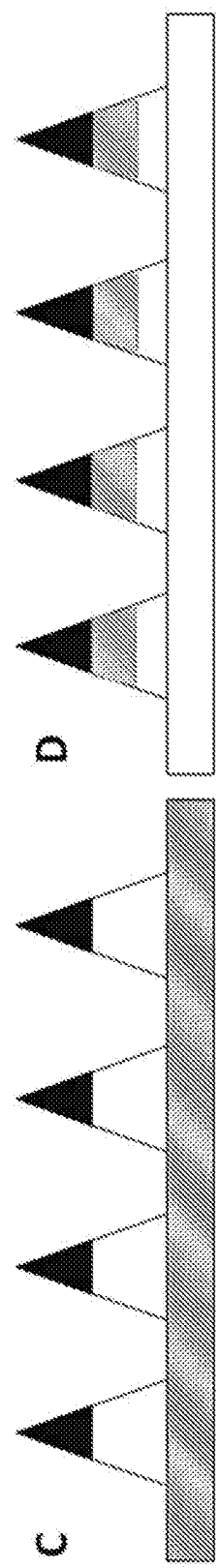
FIG. 10A
FIG. 10B
FIG. 10C
FIG. 10D

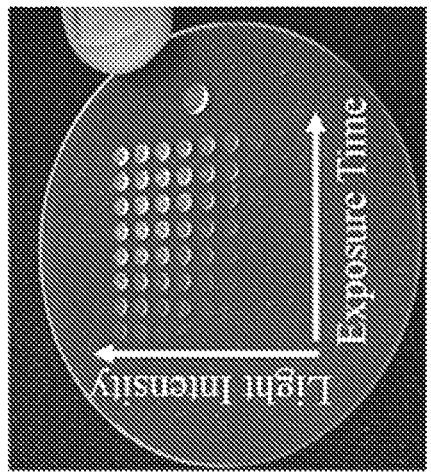
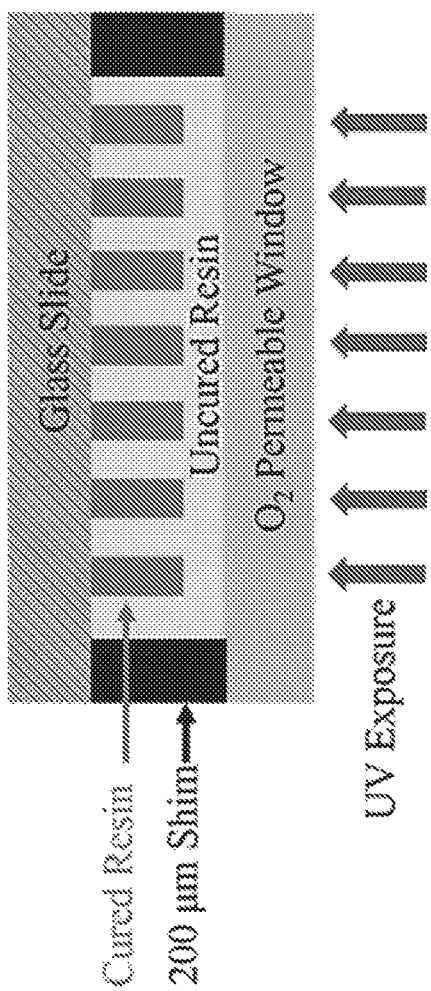
FIG. 13B
FIG. 13A

POLYMERIC MICRONEEDLES AND RAPID ADDITIVE MANUFACTURING OF THE SAME

CROSS-REFERENCE TO RELATED APPLICATIONS

This Application is a U.S. National Phase Application of International Application No. PCT/US2016/022231, filed Mar. 12, 2016, which claims the benefit of U.S. Provisional Application No. 62/132,990, filed on Mar. 13, 2015, which is incorporated herein by reference in its entirety.

STATEMENT REGARDING FEDERALLY SPONSORED RESEARCH

This invention was made with government support under Grant No. HDTRA 1-13-1-0045 awarded by the Department of Defense. The government has certain rights in the invention.

BACKGROUND

Polymeric microneedles are usually fabricated in three distinct steps: master fabrication, mold fabrication, and mold filling. Each of these steps present unique challenges that have hindered the commercialization of microneedle technology. In a typical process, a metal or silicon master would be created using traditional microfabrication techniques, such as deep reactive ion etching (DRIE), wet etching, laser ablation, or tilted ultraviolet photolithography. Taken as a whole, master fabrication processes are time consuming, require expensive equipment and substantial expertise, and limit control over the shape of the resulting microneedle. For example, dry etching techniques used to make microneedles vertically etch on the order of 1-5 µm per minute, producing a microneedle master at upwards of ~1.5 hours, depending on microneedle height. Due to extensive process optimization required to generate a microneedle structure, substantial lead time is also required. Following the master fabrication, a mold is then cast in polydimethylsiloxane (PDMS) and filled with a formulation of interest using a series of vacuum and centrifugation steps. These time-consuming vacuum and centrifugation steps (on the order of hours to days) limit opportunity for cost effective scale-up of manufacturing processes.

Due to the current processing limitations, microneedle size, shape, sharpness, aspect ratio, and spacing are therefore dictated by feasibility of fabrication rather than ideal design. However, numerous studies indicate that proper optimization of microneedle morphology and spacing is essential to successful and complete insertion into the skin. Therefore, there remains a need for devices and methods that overcome these deficiencies and that effectively provide polymeric microneedles.

SUMMARY

In accordance with the purpose(s) of the invention, as embodied and broadly described herein, the invention, in one aspect, relates to microneedle devices, methods of making same, pharmaceutical compositions comprising same, and methods of treating a disease comprising administering same.

Disclosed are microneedle devices comprising: (a) a backing; and (h) a plurality of biocompatible microneedles projecting from the backing, and wherein the microneedles comprise one or more of: (i) a curved, discontinuous, undercut, and/or perforated sidewall; (ii) a sidewall comprising a breakable support; and (iii) a cross-section that is non-circular and non-polygonal, and/or wherein the microneedles are tiered, and wherein the microneedles have a cross-sectional width that varies in both dimensions along at least a portion of their length.

Also disclosed are methods of delivering a therapeutic agent to a subject, the method comprising administering to the subject a microneedle device comprising: (a) a backing; and (b) a plurality of biocompatible microneedles projecting from the backing, wherein the microneedles comprise a therapeutic agent and one or more of: (i) a curved, discontinuous, undercut, or perforated sidewall; (ii) a sidewall comprising a breakable support; and (iii) a cross-section that is non-circular and non-polygonal, and/or wherein the microneedles are tiered, thereby delivering the therapeutic agent.

Also disclosed are methods of treating a disease in a subject, the method comprising administering to the subject a microneedle device comprising: (a) a backing; and (b) a plurality of biocompatible microneedles projecting from the backing, wherein the microneedles comprise a therapeutic agent and one or more of: (i) a curved, discontinuous, undercut, or perforated sidewall; (ii) a sidewall comprising a breakable support; and (iii) a cross-section that is non-circular and non-polygonal, and/or wherein the microneedles are tiered, thereby treating the disease.

Also disclosed are of methods of detecting a biomarker in a sample, the method comprising: (a) providing a microneedle device comprising: (i) a backing; and (ii) a plurality of biocompatible microneedles projecting from the backing, wherein the microneedles comprise a probe for the biomarker and one or more of: (1) a curved, discontinuous, undercut, and/or perforated sidewall; (2) a sidewall comprising a breakable support; and (3) a cross-section that is non-circular and non-polygonal, and/or wherein the microneedles are tiered; (b) contacting the device with the sample; and (c) identifying the biomarker, thereby detecting the biomarker in the sample.

Also disclosed are methods of making a disclosed microneedle device.

Also disclosed are methods of making a microneedle device, the method comprising the steps of (a) providing a build elevator and an optically transparent build surface, wherein the build elevator and the build surface together define a build region there between, wherein the build surface is permeable to a polymerization inhibitor, and wherein the build surface is in fluid communication with a source of the polymerization inhibitor; (b) filling the build region with a polymerizable liquid; (c) irradiating the build region through the build surface to produce a solid polymerized region in the build region; (d) forming or maintaining a liquid film release layer between the solid polymerized region and the build surface, wherein the liquid film release layer comprises the polymerizable liquid, and wherein the polymerization of the liquid is inhibited by the polymerization inhibitor; and (e) advancing the build elevator away from the build surface to create a subsequent build region between the solid polymerized region and the build surface while concurrently filling the subsequent build region with the polymerizable liquid, wherein the device comprises: (f) a backing; and (g) a plurality of biocompatible microneedles projecting from the backing, wherein the microneedles comprise one or more of: (i) a curved, discontinuous, undercut, or perforated sidewall; (ii) a sidewall comprising a breakable support; and (iii) a cross-section that is non-circular and non-polygonal, and/or wherein the microneedles are tiered, thereby making the microneedle device.

Also disclosed are microneedle devices comprising: a backing; and a plurality of polymeric biocompatible microneedles projecting from the backing. In various aspects, the microneedles and/or backing are biocompatible. In various aspects, the microneedles and/or backing are biodegradable and/or bioabsorbable. In various aspects, the microneedles have a curved, discontinuous or undercut sidewall. In various aspects, the microneedles have a non-circular or non-polygonal (e.g., non-square) cross-section.

Also disclosed are methods of delivering a therapeutic agent to a subject in need thereof, comprising administering to said subject a microneedle device as taught herein comprising the therapeutic agent.

Also disclosed are methods of treating a disease or condition in a subject in need thereof, comprising administering to said subject a microneedle device as taught herein comprising a therapeutic agent for treatment thereof.

Also disclosed are methods of making a microneedle device as taught herein, comprising the steps of: (a) providing a build elevator and an optically transparent build surface defining a build region there between, said build surface being permeable to a polymerization inhibitor, and with said build surface in fluid communication with a source of the polymerization inhibitor (b) filling said build region with a polymerizable liquid, said polymerizable liquid contacting said build surface, (c) irradiating said build region through said build surface to produce a solid polymerized region in said build region, while forming or maintaining a liquid film release layer comprised of said polymerizable liquid formed between said solid polymerized region and said build surface, wherein the polymerization of which liquid film is inhibited by said polymerization inhibitor; and (d) advancing said build elevator with said polymerized region adhered thereto away from said build surface to create a subsequent build region between said polymerized region and said build surface while concurrently filling said subsequent build region with polymerizable liquid as in step (b), to thereby form the microneedle device.

While aspects of the present invention can be described and claimed in a particular statutory class, such as the system statutory class, this is for convenience only and one of skill in the art will understand that each aspect of the present invention can be described and claimed in any statutory class. Unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

BRIEF DESCRIPTION OF THE DRAWINGS

The accompanying figures, which are incorporated in and constitute a part of this specification, illustrate several aspects and together with the description serve to explain the principles of the invention.

FIG. 1A shows a representative depiction of a microneedle patch with arrows representing individual needles. FIG. 1B-E show representative depictions of individual microneedles with breakable supports at the base (1B), middle (1C), top (1D), and undercut (1E) of the microneedle. FIG. 1F-I shows a representative depiction of microneedles with separation at the base (1F), middle (1G), top (1H), and undercut (1I) of the microneedle after insertion in the skin followed by application of torsion or other physical force.

FIG. 2A shows a representative depiction of a microneedle patch with arrows representing individual needles. FIG. 2B-D show representative depictions of individual microneedles with horizontal (2B), diagonal (2C), or multi-directional (2E) breakable perforations. FIG. 2E-G show representative depictions of microneedles with separation horizontal (2E), diagonal (2F), or multi-directional (2G) after insertion in the skin and application of torsion or other physical force.

FIG. 3A shows a representative depiction of a microneedle patch with arrows representing individual needles. FIG. 3B-D show representative depictions of individual microneedles with horizontal (3B), diagonal (3C), or multi-directional (3D) chemical perforations. FIG. 3E-G show representative depictions of microneedles with separation horizontal (3E), diagonal (3F), or multi-directional (3G) following exposure to stimuli that trigger disruption of the chemical perforation.

FIG. 10A-D show representative examples of multi-component microneedles with layers along the z-axis in which the needle tip (10A), patch backing (10B), needle tip and patch backing (10C), and multiple layers of the needle (10D) comprise different compositions.

FIG. 13A and FIG. 13B show representative images measuring dot thickness to quantify dead zone and cure thickness. Specifically, FIG. 13A shows a representative schematic of a differential dead zone thickness measurement. FIG. 13B shows a representative image of cured thickness as a function of photon flux and exposure time. Each exposed dot has a diameter of 3 mm.

FIG. 19A-C show representative images of TMPTA microneedles with 1000 μm (19A), 700 μm (19B), and 400 μm (19C) nominal heights height. Scale bars are 500 μm. FIG. 19D shows a representative 1800× view of a microneedle tip with a tip radius less than 5 μm. Scale bar is 5 μm.

FIG. 20A-C show representative images illustrating that microneedle arrays made of TMPTA (20A), PAA (20B), and PEG (20C) on murine skin can be visualized using a green tissue marking dye. FIG. 20D show a representative image illustrating that no insertion sites are visualized on a piece of control skin to which no microneedles were applied.

FIG. 21A shows the representative dimensions of an individual needle used for insulin loading calculations. FIG. 21B shows the representative size of a patch required to dose 4 U of insulin.

FIG. 22A shows a representative diagram of the cylinder dimensions, FIG. 22B shows a representative image of CLIP vehicle control and OVA-647 loaded PAA cylinders, and FIG. 22C shows a representative florescence microscopy image of OVA-647 signal in vehicle control and OVA-647 loaded PAA cylinders.

Figure 1:
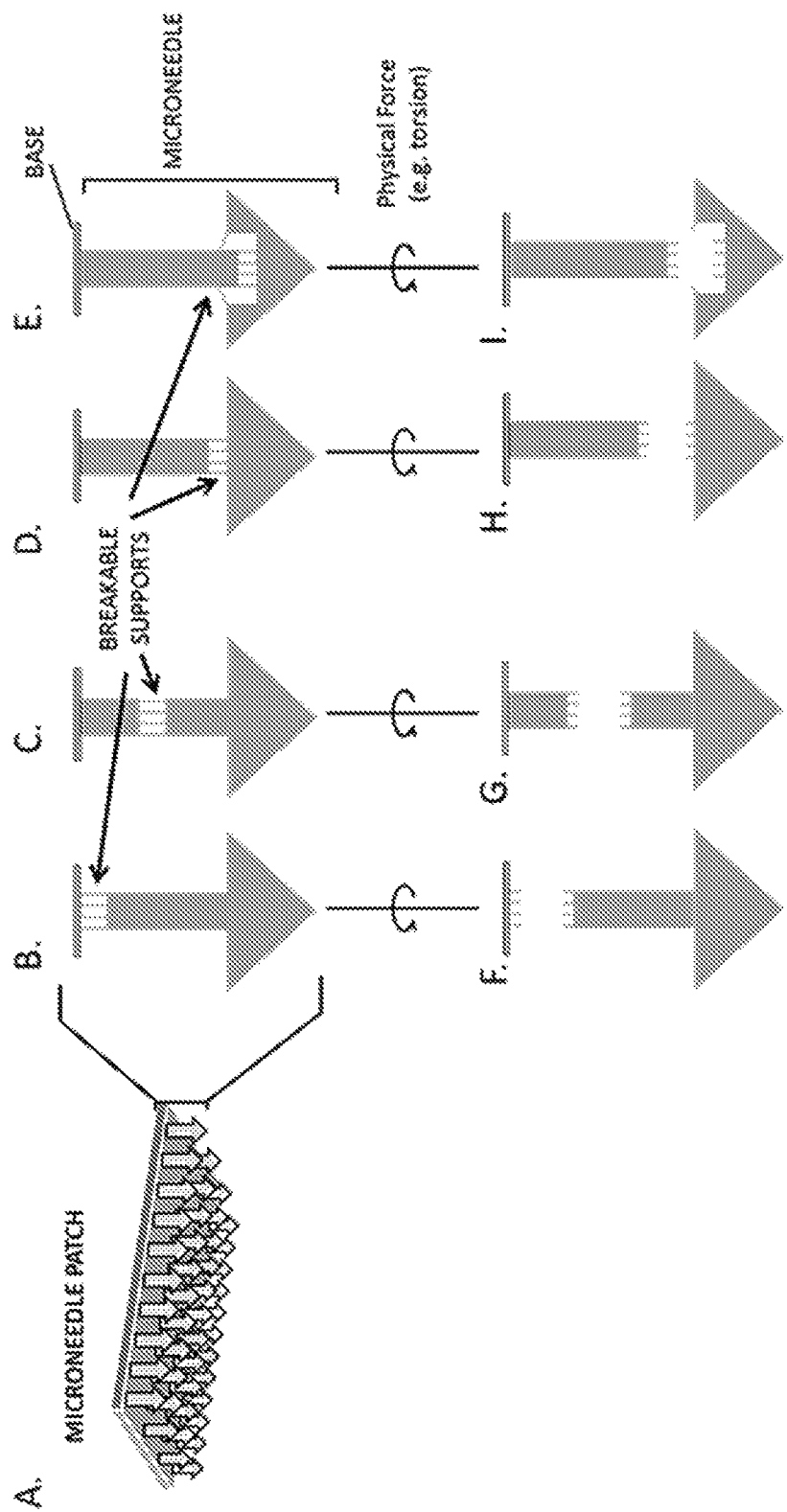
FIG. 1A-I show representative diagrams of microneedles engineered with breakable supports. Specifically.
Figure 2:
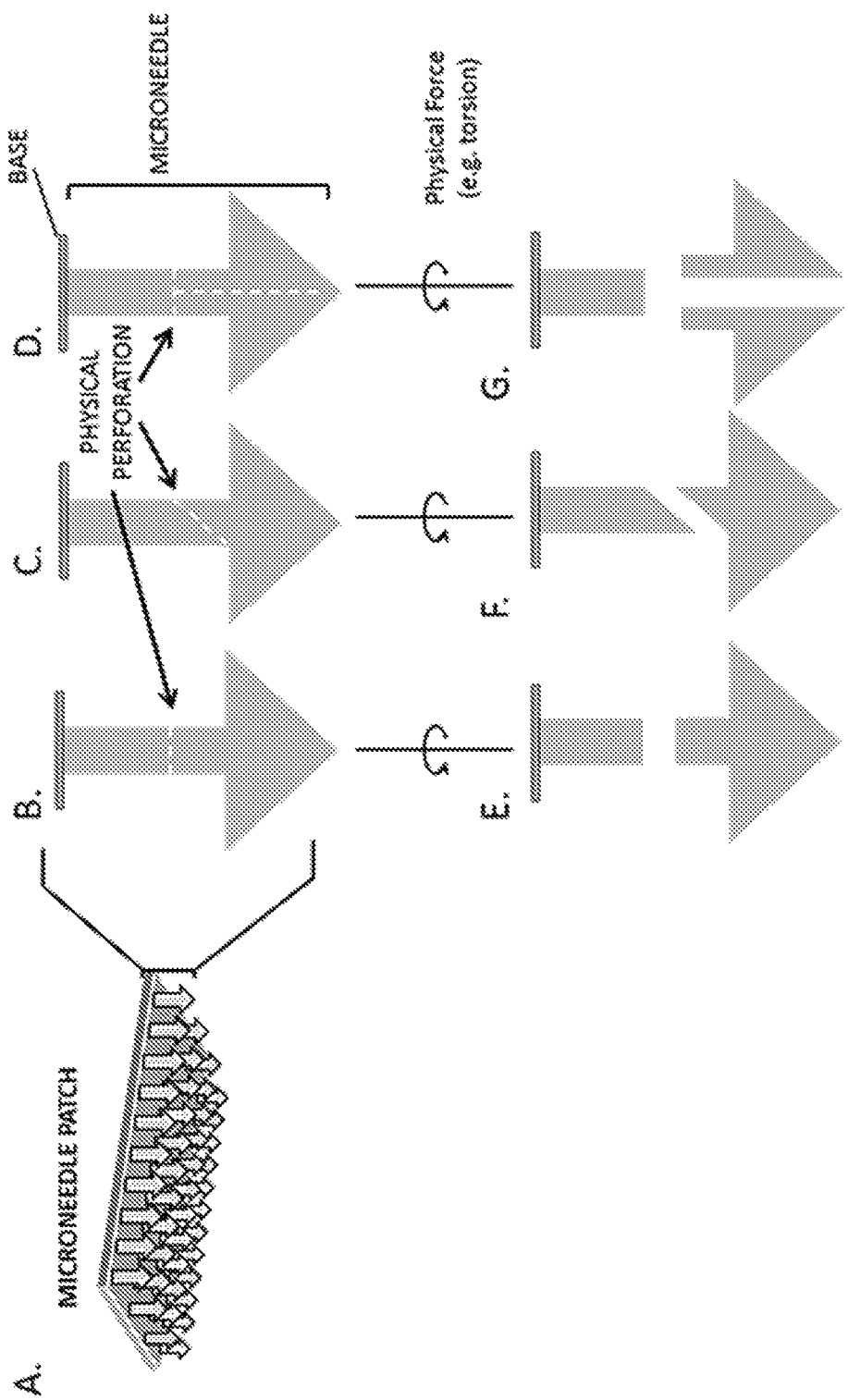
FIG. 2A-G show representative diagrams of microneedles engineered with physical perforations. Specifically.
Figure 3:
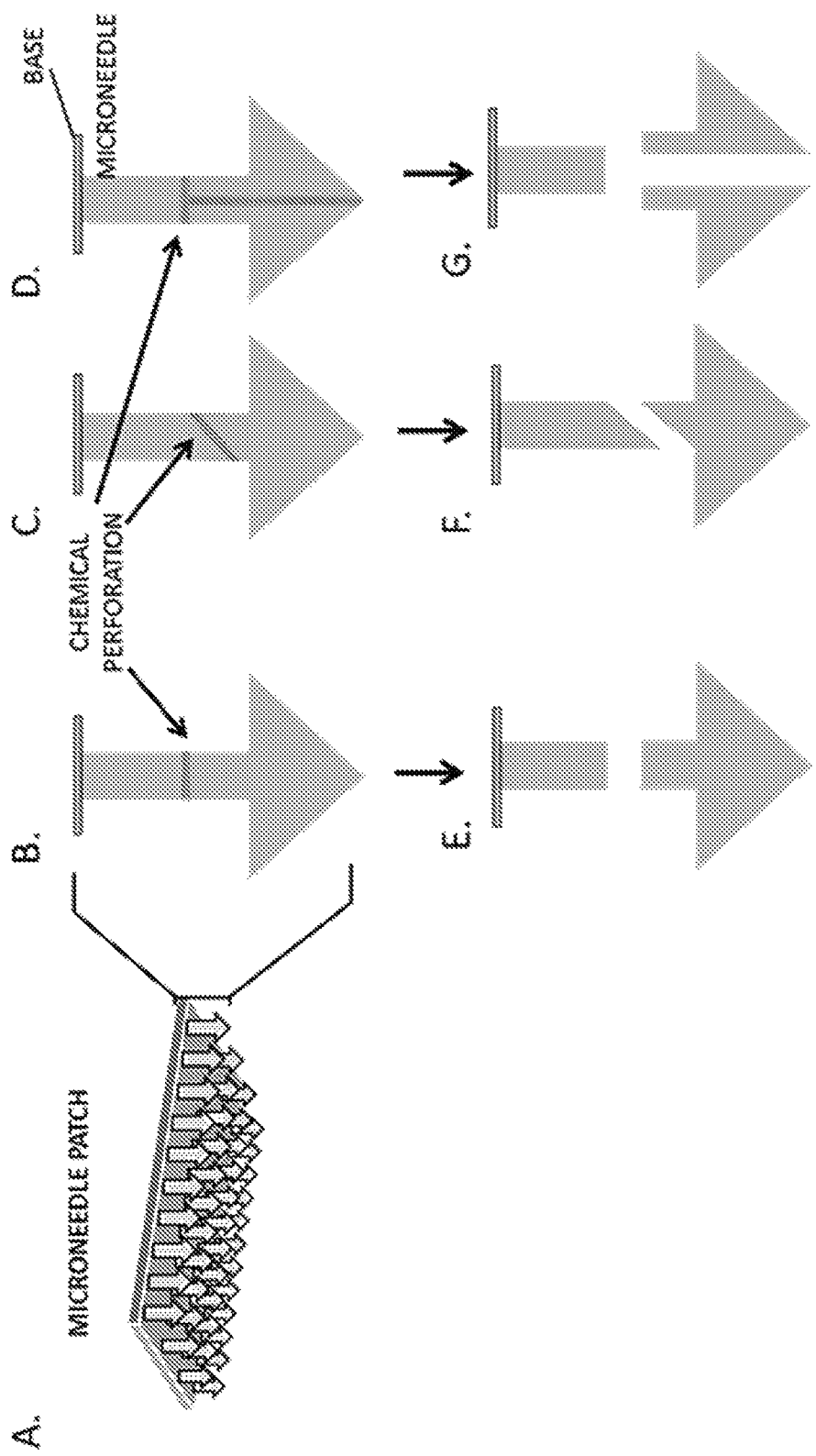
FIG. 3A-G show representative diagrams of breakable microneedles engineered with chemical perforations. Specifically.

Additional advantages of the invention will be set forth in part in the description which follows, and in part will be obvious from the description, or can be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

DETAILED DESCRIPTION

The present invention can be understood more readily by reference to the following detailed description of the invention and the Examples included therein.

Before the present compounds, compositions, articles, systems, devices, and/or methods are disclosed and described, it is to be understood that they are not limited to specific synthetic methods unless otherwise specified, or to particular reagents unless otherwise specified, as such may, of course, vary. It is also to be understood that the terminology used herein is for the purpose of describing particular aspects only and is not intended to be limiting. Although any methods and materials similar or equivalent to those described herein can be used in the practice or testing of the present invention, example methods and materials are now described.

Throughout this application, various publications are referenced. The disclosures of these publications in their entireties are hereby incorporated by reference into this application in order to more fully describe the state of the art to which this pertains. The references disclosed are also individually and specifically incorporated by reference herein for the material contained in them that is discussed in the sentence in which the reference is relied upon. Further, the dates of publication provided herein may be different from the actual publication dates, which can require independent confirmation.

A. DEFINITIONS

The present invention now will be described more fully hereinafter with reference to the accompanying drawings, in which illustrative aspects of the invention are shown. In the drawings, the relative sizes of regions or features may be exaggerated for clarity. This invention may, however, be embodied in many different forms and should not be construed as limited to the aspects set forth herein rather, these aspects are provided so that this disclosure will be thorough and complete, and will fully convey the scope of the invention to those skilled in the art.

In addition, spatially relative terms, such as "under," "below," "lower," "over," "upper," and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly.

It will be understood that when an element is referred to as being "coupled" or "connected" to another element, it can be directly coupled or connected to the other element or intervening elements may also be present. In contrast, when an element is referred to as being "directly coupled" or "directly connected" to another element, there are no intervening elements present. Like numbers refer to like elements throughout. As used herein the term "and/or" includes any and all combinations of one or more of the associated listed items.

Well-known functions or constructions may not be described in detail for brevity and/or clarity.

The disclosures of all patent references cited herein are hereby incorporated by reference to the extent they are consistent with the disclosure set forth herein. As used herein in the description of the invention and the appended claims, the singular forms "a," "an," and "the" are intended to include the plural forms as well, unless the context clearly indicates otherwise.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the present application and relevant art and should not be interpreted in an idealized or overly formal sense unless expressly so defined herein. The terminology used in the description of the invention herein is for the purpose of describing particular aspects only and is not intended to be limiting of the invention. All publications, patent applications, patents and other references mentioned herein are incorporated by reference in their entirety. In case of a conflict in terminology, the present specification is controlling.

Also as used herein, "and/or" refers to and encompasses any and all possible combinations of one or more of the associated listed items, as well as the lack of combinations when interpreted in the alternative ("or").

Unless the context indicates otherwise, it is specifically intended that the various features of the invention described herein can be used in any combination. Moreover, the present invention also contemplates that In various aspects of the invention, any feature or combination of features set forth herein can be excluded or omitted. To illustrate, if the specification states that a complex comprises components A, B and C, it is specifically intended that any of A, B or C, or a combination thereof, can be omitted and disclaimed.

The term "about," as used herein when referring to a measurable value, such as, for example, an amount or concentration and the like, is meant to encompass variations of ±20%, ±10%, ±5%, ±1%, ±0.5%, or even ±0.1% of the specified amount. A range provided herein for a measureable value may include any other range and/or individual value therein.

As used herein, "hiocompatible" refers to materials that are not unduly reactive or harmful to a subject upon administration.

"Biodegradable" as used herein refers to the ability of a material to be broken down in vivo upon administration to a subject. For example, the materials may be dissolvable in skin tissue. See, e.g., Lee et al., "Dissolving Microneedles for Transdermal Drug Delivery," Biomaterials 29(13):2113-2124, 2008, In various aspects, materials may be chosen to biodegrade at a predetermined rate, e.g., for controlled delivery of a therapeutic agent cargo.

"Bioabsorbable" as used herein means capable of being absorbed into living tissue.

The amount of agents that may be incorporated in the microneedles described herein can vary from picogram levels to milligram levels, depending on the size of microneedles and/or encapsulation efficiency. Non-limiting examples of agents include organic materials such as horseradish peroxidase, phenolsulfonphthalein, nucleotides, nucleic acids (e.g., oligonucleotides, polynucleotides, siRNA, shRNA), aptamers, antibodies or portions thereof (e.g., antibody-like molecules), hormones (e.g., insulin, testosterone), growth factors, enzymes (e.g., peroxidase, lipase, amylase, organophosphate dehydrogenase, ligases, restriction endonucleases, ribonucleases, RNA or DNA polymerases, glucose oxidase, lactase), cells (e.g., red blood cells, stem cells), bacteria or viruses, other proteins or peptides, small molecules (e.g., drugs, dyes, amino acids, vitamins, antioxidants), lipids, carbohydrates, chromophores, light emitting organic compounds (such as luciferin, carotenes) and light emitting inorganic compounds (e.g., chemical dyes and/or contrast enhancing agents such as indocyanine green), immunogenic substances such as vaccines, antibiotics, antifungal agents, antiviral agents, therapeutic agents, diagnostic agents or pro-drugs, analogs or combinations of any of the foregoing.

Examples of immunogenic vaccine substances that can be included in the microneedles described herein include, but are not limited to, those in BIOTHRAX® (anthrax vaccine adsorbed, Emergent Biosolutions, Rockville, Md.); TICE® BCG Live (Bacillus Calmette-Guerin for intravesical use, Organon Tekina Corp. LLC, Durham, N.C.); MYCOBAX® BCG Live (Sanofi Pasteur Inc); DAPTACEL® (diphtheria and tetanus toxoids and acellular pertussis [DTaP] vaccine adsorbed, Sanofi Pasteur Inc.); INFANRIX® (DTaP vaccine adsorbed, GlaxoSmithKline); TRIPEDIA® (DTaP vaccine, Sanofi Pasteur); TRIHIBIT® (DTaP/Hib #, sanofi pasteur); KINRIX® (diphtheria and tetanus toxoids, acellular pertussis adsorbed and inactivated poliovirus vaccine, GlaxoSmithKline); PEDIARIX® (DTaP-HepB-IPV, GlaxoSmithKline); PENTACEL® (diphtheria and tetanus toxoids and acellular pertussis adsorbed, inactivated poliovirus and Haemophilus b conjugate [tetanus toxoid conjugate] vaccine, sanofi pasteur); Diphtheria and Tetanus Toxoids, adsorbed (for pediatric use, Sanofi Pasteur); DECAVAC® (diphtheria and tetanus toxoids adsorbed, for adult use, Sanofi Pasteur); ACTHIB® (Haemophilus b tetanus toxoid conjugate vaccine, Sanofi Pasteur); PEDVAXHIB® (Hib vaccine, Merck); Hiberix (Haemophilus b tetanus toxoid conjugate vaccine, booster dose, GlaxoSmithKline); COMVAX® (Hepatitis B-Hib vaccine, Merck); HAVRIX® (Hepatitis A vaccine, pediatric, GlaxoSmithKline); VAQTA® (Hepatitis A vaccine, pediatric, Merck); ENGERIX-B® (Hep B, pediatric, adolescent, GlaxoSmithKline); RECOMBIVAX HB®

(hepatitis B vaccine, Merck); TWINRIX®, (HepA/HepB vaccine, 18 years and up, GlaxoSmithKline); CERVARIX® (human papillomavirus bivalent [types 16 and 18] vaccine, recombinant, GlaxoSmithKline); GARDASIL® (human papillomavirus bivalent [types 6, 11, 16 and 18] vaccine, recombinant, Merck); AFLURIA® (Influenza vaccine, 18 years and up, CSL); AGRIFLU™ (influenza virus vaccine for intramuscular injection, Novartis Vaccines); FLUARIX® (Influenza vaccine, 18 years and up, GaxoSmithKline); FLULAVAL® (Influenza vaccine, 18 years and up, GlaxoSmithKline); FLUVIRIN® (Influenza vaccine, 4 years and up, Novartis Vaccine); FLUZONE® (Influenza vaccine, 6 months and up, Sanofi Pasteur); FLUMIST® (Influenza vaccine, 2 years and up, MedImmune); IPOL® (e-IPV polio vaccine, sanofi Pasteur); JE VAX® (Japanese encephalitis virus vaccine inactivated, BIKEN, Japan); IXIARO® (Japanese encephalitis virus vaccine inactivated, Novarits); MENACTRA® (Meningococcal [Groups A, C, Y and W-135] and diphtheria vaccine, Sanofi Pasteur); MENOMUNE®-A/C/Y/W-135 (Meningococcal polysaccharide vaccine, sanofi pasteur); MMRII® (MMR vaccine, Merck); MENVEO® (Meningococcal [Groups A, C, Y and W-135] oligosaccharide diphtheria CRM 197 conjugate vaccine, Novartis Vaccines); PROQUAD® (MMR and varicella vaccine, Merck); PNEUMOVAX 23® (pneumococcal polysaccharide vaccine, Merck); PREVNAR® (pneumococcal vaccine, 7-valent, Wyeth/Lederle); PREVNAR-13® (pneumococcal vaccine, 13-valent, Wyeth/Lederle); POLIO VAX™ (poliovirus inactivated, sanofi pasteur); IMOVAX® (Rabies vaccine, Sanofi Pasteur); RABAVERT™ (Rabies vaccine, Chiron); ROTATEQ® (Rotavirus vaccine, live, oral pentavalent, Merck); ROTARIX® (Rotavirus, live, oral vaccine, GlaxoSmithKline); DECAVAC™ (tetanus and diphtheria toxoids vaccine, sanofi pasteur); Td (generic) (tetanus and diphtheria toxoids, adsorbed, Massachusetts Biol. Labs); TYPHIMV1® (typhoid Vi polysaccharide vaccine, Sanofi Pasteur); ADACEL® (tetanus toxoid, reduced diphtheria toxoid and acellular pertussis, sanofi pasteur); BOOSTRIX® (tetanus toxoid, reduced diphtheria toxoid and acellular pertussis, GlaxoSmithKline); VIVOTIF® (typhoid vaccine live oral Ty21a, Bema Biotech); ACAM2000™ (Smallpox (vaccinia) vaccine, live, Acambis, Inc.); DRYVAX® (Smallpox (vaccinia) vaccine); VARIVAX® (varicella [live] vaccine, Merck); YF-VAX® (Yellow fever vaccine, Sanofi Pasteur); ZOSTAVAX®, (Varicella zoster, Merck); or combinations thereof. Any vaccine products listed in database of Center for Disease Control and Prevention (CDC) can also be included in the compositions described herein.

As used herein, "small molecule" refers to natural or synthetic molecules including, but not limited to, peptides, peptidomimetics, amino acids, amino acid analogs, polynucleotides, polynucleotide analogs, aptamers, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

The term "antibiotic" is used herein to describe a compound that acts as an antimicrobial, bacteriostatic, or bactericidal agent. Example antibiotics include, but are not limited to, penicillins, cephalosporins, penems, carbapenems, monobactams, aminoglycosides, sulfonamides, macrolides, tetracyclins, lincosides, quinolones, chloramphenicol, vancomycin, metronidazole, rifampin, isoniazid, spectinomycin, trimethoprim, and sulfamethoxazole.

The term "therapeutic agent" is art-recognized and refers to any chemical moiety, that is a biologically, physiologically, or pharmacologically active substance that acts locally or systemically in a subject. Examples of therapeutic agents, also referred to as "drugs," are described in well-known literature references such as the Merck Index, the Physicians Desk Reference, and The Pharmacological Basis of Therapeutics, and they include, without limitation, medicaments; vitamins; mineral supplements; substances used for the treatment, prevention, diagnosis, cure or mitigation of a disease or illness; substances which affect the structure or function of the body; or pro-drugs, which become biologically active or more active after they have been placed in a physiological environment. Various forms of a therapeutic agent may be used which are capable of being released from the subject composition into adjacent tissues or fluids upon administration to a subject. Examples include steroids and esters of steroids (e.g., estrogen, progesterone, testosterone, androsterone, cholesterol, norethindrone, digoxigenin, cholic acid, deoxycholic acid, and chenodeoxycholic acid), boron-containing compounds (e.g., carborane), chemotherapeutic nucleotides, drugs (e.g., antibiotics, antivirals, antifungals), enediynes (e.g., calicheamicins, esperamicins, dynemicin, neocarzino statin chromophore, and kedarcidin chromophore), heavy metal complexes e.g., cisplatin), hormone antagonists (e.g., tamoxifen), non-specific (non-antibody) proteins (e.g., sugar oligomers), oligonucleotides antisense oligonucleotides that bind to a target nucleic acid sequence (e.g., mRNA sequence)), peptides, proteins, antibodies, photodynamic agents (e.g., rhodamine 123), radionuclides (e.g., I-131, Re-186, Re-188, Y-90, Bi-212, At-211, Sr-89, Ho-166, Sm-153, Cu-67 and Cu-64), toxins (e.g., ricin), and transcription-based pharmaceuticals.

In various aspects, the therapeutic agent can include a pain medication. Examples of pain medications include, but are not limited to, acetaminophen, non-steroidal antiinflammatory medications (NSAIDs), corticosteroids; narcotics; anti-convulsants; local anesthetics, and any combinations thereof. NSAIDs that can be included In various aspects of the microneedles provided herein include, but not limited to, ibuprofen, naproxin, aspirin, fenoprofen, flurbiprofen, ketoprofen, oxaprozin, diclofenac sodium, etodolac, indomethacin, ketorolac, sulindac, tolmetin, meclofenamate, mefenamic acid, nabumetone, piroxicam and COX-2 inhibitors. In various aspects, the pain medications can include acetaminophen combinations (e.g., acetaminophen with a narcotic) such as acetaminophen with codeine; acetaminophen with hydrocodone; and acetaminophen with oxycodone.

In various aspects of the device, the substrate can be formed from any flexible material. In such aspects, the substrate can be sufficiently flexible to conform to a surface upon contact with the surface, e.g., a tissue or an organ surface, while allowing the microneedles to penetrate the tissue to the desired depth. In one aspect, the flexible substrate comprises a silk fibroin film integrated with silk fibroin microneedles. In alternative aspects, the substrate can be any rigid material.

In various aspects the microneedles are provided in the form of a patch which comprises a backing and a plurality of microneedles projecting from the backing. The backing can be made of the same material or a different material, and can have a substantially flat surface, a curved surface, a wavy surface or any combination thereof. In various aspects, the surface is configured to have a curvature profile similar to that of a target surface to be penetrated.

The backing can be of any shape and/or any dimension determined from, for example, design of the microneedle device, area/shape of a target site to be treated, and/or size of microneedle applicators. In various aspects, the shape and dimension of the backing can be configured to fit any applicator that currently uses hypodermic needles as the barrier penetration method (e.g., syringes), any microinjection equipment, any microneedle holders, any microneedle administration or applicator devices, any microneedle array applicator devices, and/or microneedle array cartridge systems. Non-limiting examples of the microneedle or microneedle array injectors or applicators include the ones described in U.S. Patent Application Nos.: US 2008/0183144; US 2003/0208167; US 2010/0256597; and U.S. Patent Nos.: U.S. Pat. Nos. 6,743,211; and 7,842,008, See also US 2013/0338632 to Kaplan et al.

In various aspects, microneedles as taught herein may be hollow and/or porous. See, e.g., Burton et al., "Rapid Intradermal Delivery of Liquid Formulations Using a Hollow Microstructured Array," Pharm. Res. 28:31-40, 2011.

B. MICRONEEDLE (MN) DEVICES

In one aspect, disclosed are microneedle devices comprising: (a) a backing; and (b) a plurality of biocompatible microneedles projecting from the backing, and wherein the microneedles comprise one or more of: (i) a curved, discontinuous, undercut, and/or perforated sidewall; (ii) a sidewall comprising a breakable support; and (iii) a cross-section that is non-circular and non-polygonal, and/or wherein the microneedles are tiered, and wherein the microneedles have a cross-sectional width that varies in both dimensions along at least a portion of their length.

In one aspect, disclosed are microneedle devices comprising: (a) a backing; and (b) a plurality of biocompatible microneedles projecting from the backing, wherein said biocompatible microneedles are biodegradable and/or bioabsorbable, and/or wherein said microneedles have a curved, discontinuous or undercut sidewall and/or have a non-circular or non-polygonal (e.g., non-square) cross-section.

In a further aspect, the microneedles have an average diameter of from 5, 10, 25, 50 or 100, to 250, 500, 750 or 1,000 micrometers, and/or an average length of from 5, 10, 25, 50 or 100, to 250, 500, 750 or 1,000 micrometers, and/or an average distance from one another of from 5, 10, 25, 50 or 100, to 250, 500, 750 or 1,000 micrometers.

In a further aspect, the microneedles have an average diameter of from 5 to 1,000 micrometers, and/or an average length of from 5 to 1,500 micrometers, and/or an average distance from one another of from 5 to 1,000 micrometers.

In a further aspect, the microneedles have an average diameter of from about 5 micrometers to about 1,000 micrometers and/or an average length of from about 5 micrometers to about 1,500 micrometers, and/or an average distance of from about 5 micrometers to about 1,000 micrometers from one another. In a still further aspect, the microneedles have an average diameter of from about 5 micrometers to about 1,000 micrometers and an average length of from about 5 micrometers to about 1,500 micrometers, and an average distance of from about 5 micrometers to about 1,000 micrometers from one another. In yet a further aspect, the microneedles have an average diameter of from about 5 micrometers to about 1,000 micrometers and an average length of from about 5 micrometers to about 1,500 micrometers, or an average distance of from about 5 micrometers to about 1,000 micrometers from one another. In an even further aspect, the microneedles have an average diameter of from about 5 micrometers to about 1,000 micrometers or an average length of from about 5 micrometers to about 1,500 micrometers, and an average distance of from about 5 micrometers to about 1,000 micrometers from one another. In a still further aspect, the microneedles have an average diameter of from about 5 micrometers to about 1,000 micrometers or an average length of from about 5 micrometers to about 1,500 micrometers, or an average distance of from about 5 micrometers to about 1,000 micrometers from one another.

In a further aspect, the microneedles have an average diameter of from about 5 micrometers to about 1,000 micrometers. In a still further aspect, the microneedles have an average diameter of from about 5 micrometers to about 750 micrometers. In yet a further aspect, the microneedles have an average diameter of from about 5 micrometers to about 500 micrometers. In an even further aspect, the microneedles have an average diameter of from about 5 micrometers to about 250 micrometers. In a still further aspect, the microneedles have an average diameter of from about 5 micrometers to about 100 micrometers. In yet a further aspect, the microneedles have an average diameter of from about 5 micrometers to about 50 micrometers. In an even further aspect, the microneedles have an average diameter of from about 5 micrometers to about 25 micrometers. In a still further aspect, the microneedles have an average diameter of from about 5 micrometers to about 10 micrometers. In yet a further aspect, the microneedles have an average diameter of from about 10 micrometers to about 1,000 micrometers. In an even further aspect, the microneedles have an average diameter of from about 25 micrometers to about 1,000 micrometers. In a still further aspect, the microneedles have an average diameter of from about 50 micrometers to about 1,000 micrometers. In yet a further aspect, the microneedles have an average diameter of from about 100 micrometers to about 1,000 micrometers. In an even further aspect, the microneedles have an average diameter of from about 250 micrometers to about 1,000 micrometers. In a still further aspect, the microneedles have an average diameter of from about 500 micrometers to about 1,000 micrometers. In yet a further aspect, the microneedles have an average diameter of from about 750 micrometers to about 1,000 micrometers.

In a further aspect, the microneedles have an average length of from about 5 micrometers to about 1,000 micrometers. In a still further aspect, the microneedles have an average length of from about 5 micrometers to about 750 micrometers. In yet a further aspect, the microneedles have an average length of from about 5 micrometers to about 500 micrometers. In an even further aspect, the microneedles have an average length of from about 5 micrometers to about 250 micrometers. In a still further aspect, the microneedles have an average length of from about 5 micrometers to about 100 micrometers. In yet a further aspect, the microneedles have an average length of from about 5 micrometers to about 50 micrometers. In an even further aspect, the microneedles have an average length of from about 5 micrometers to about 25 micrometers. In a still further aspect, the microneedles have an average length of from about 5 micrometers to about 10 micrometers. In yet a further aspect, the microneedles have an average length of from about 10 micrometers to about 1,000 micrometers. In an even further aspect, the microneedles have an average length of from about 25 micrometers to about 1,000 micrometers. In a still further aspect, the microneedles have an average length of from about 50 micrometers to about 1,000 micrometers. In yet a further aspect, the microneedles have an average length of from about 100 micrometers to about 1,000 micrometers. In an even further aspect, the microneedles have an average length of from about 250 micrometers to about 1,000 micrometers. In a still further aspect, the microneedles have an average length of from about 500 micrometers to about 1,000 micrometers. In yet a further aspect, the microneedles have an average length of from about 750 micrometers to about 1,000 micrometers.

In a further aspect, the microneedles have an average distance of from about 5 micrometers to about 1,000 micrometers from one another. In a still further aspect, the microneedles have an average distance of from about 5 micrometers to about 750 micrometers. In yet a further aspect, the microneedles have an average distance of from about 5 micrometers to about 500 micrometers. In an even further aspect, the microneedles have an average distance of from about 5 micrometers to about 250 micrometers. In a still further aspect, the microneedles have an average distance of from about 5 micrometers to about 100 micrometers. In yet a further aspect, the microneedles have an average distance of from about 5 micrometers to about 50 micrometers. In an even further aspect, the microneedles have an average distance of from about 5 micrometers to about 25 micrometers. In a still further aspect, the microneedles have an average distance of from about 5 micrometers to about 10 micrometers. In yet a further aspect, the microneedles have an average distance of from about 10 micrometers to about 1,000 micrometers. In an even further aspect, the microneedles have an average distance of from about 25 micrometers to about 1,000 micrometers. In a still further aspect, the microneedles have an average distance of from about 50 micrometers to about 1,000 micrometers. In yet a further aspect, the microneedles have an average distance of from about 100 micrometers to about 1,000 micrometers. In an even further aspect, the microneedles have an average distance of from about 250 micrometers to about 1,000 micrometers. In a still further aspect, the microneedles have an average distance of from about 500 micrometers to about 1,000 micrometers. In yet a further aspect, the microneedles have an average distance of from about 750 micrometers to about 1,000 micrometers.

In a further aspect, the microneedles have a tip diameter of less than 20, 15, 10, 8, 5, or 3 micrometers. In a still further aspect, the microneedles have a tip diameter of less than 20, 15, 10, 8, or 5 micrometers. In yet a further aspect, the microneedles have a tip diameter of less than 20, 15, 10, or 8 micrometers. In an even further aspect, the microneedles have a tip diameter of less than 20, 15, or 10 micrometers. In a still further aspect, the microneedles have a tip diameter of less than 20 or 15 micrometers. In yet a further aspect, the microneedles have a tip diameter of less than 15, 10, 8, 5, or 3 micrometers. In an even further aspect, the microneedles have a tip diameter of less than 10, 8, 5, or 3 micrometers. In a still further aspect, the microneedles have a tip diameter of less than 8, 5, or 3 micrometers. In yet a further aspect, the microneedles have a tip diameter of less than 5 or 3 micrometers.

In a further aspect, the microneedles have a tip diameter of less than about 20 micrometers. In a still further aspect, the microneedles have a tip diameter of less than about 15 micrometers. In yet a further aspect, the microneedles have a tip diameter of less than about 10 micrometers. In an even further aspect, the microneedles have a tip diameter of less than about 8 micrometers. In a still further aspect, the microneedles have a tip diameter of less than about 5 micrometers. In yet a further aspect, the microneedles have a tip diameter of less than about 3 micrometers.

In a further aspect, the backing and the microneedles comprise the same material. In a still further aspect, the backing and the microneedles comprise different materials.

In a further aspect, the microneedles comprise a polymer. In a still further aspect, the microneedles comprise more than one polymer. In a still further aspect, the microneedles are metal-free. In yet a further aspect, the microneedles comprise less than about 0.01 wt % metal. In an even further aspect, the microneedles comprise less than about 0.1 wt % metal. In a still further aspect, the microneedles comprise less than about 1 wt % metal. In yet a further aspect, the microneedles comprise less than about 5 wt % metal. In an even further aspect, the microneedles comprise less than about 10 wt % metal. In a still further aspect, the microneedles comprise less than about 25 wt % metal. In yet a further aspect, the microneedles comprise less than about 50 wt % metal. In an even further aspect, the microneedles comprise less than about 75 wt % metal. In a still further aspect, the microneedles comprise less than about 90 wt % metal. In yet a further aspect, the microneedles comprise less than about 95 wt % metal. In an even further aspect, the microneedles comprise less than about 99 wt % metal. In a still further aspect, the microneedles comprise metal.

In a further aspect, the microneedles have a cross-sectional width that varies in both dimensions along at least a portion of their length. In a still further aspect, the microneedles have a cross-sectional width that varies in both dimensions along their entire length. Thus, in various aspects, the length of the microneedles is not flat in either dimension.

In a further aspect, the microneedles were not produced via an "in-plane" or an "out-of-plane" technique. In a still further aspect, the microneedles were not produced via an "in-plane" technique. In yet a further aspect, the microneedles were not produced via an "out-of-plane" technique.

In a further aspect, the backing comprises a cross-section. In a still further aspect, the cross-section of the microneedle has a thickness different from the thickness of the cross-section of the backing. In yet a further aspect, the thickness of the cross-section of the microneedle is greater than the thickness of the cross-section of the backing. In an even further aspect, the thickness of the cross-section of the microneedle is less than the thickness of the cross-section of the backing. Accordingly, in various aspects, the microneedles were not punched out from the backing.

In a further aspect, the shape and/or thickness of the cross-section of the microneedles is not limited by the shape and/or thickness of the cross-section of the backing.

In a further aspect, the backing is free of cuts. In a still further aspect, the backing is free of holes. In yet a further aspect, the backing is free of cuts, wherein the cuts were used to form the microneedles. In an even further aspect, the backing is free of holes, wherein the holes were used to form the microneedles.

In a further aspect, the microneedles comprise a curved, discontinuous, undercut, or perforated sidewall. In a still further aspect, the microneedles comprise a curved, discontinuous, or undercut sidewall. In yet a further aspect, the microneedles comprise a curved sidewall. In an even further aspect, the microneedles comprise a discontinuous sidewall. In a still further aspect, the microneedles comprise an undercut sidewall. In yet a further aspect, the microneedles comprise a perforated sidewall.

In a further aspect, the microneedles comprise a sidewall comprising a breakable support.

In a further aspect, the microneedles comprise a cross-section that is non-circular and non-polygonal.

In a further aspect, the microneedles are hollow.

In a further aspect, the microneedles are tiered.

In a further aspect, the microneedles are dissolvable. In a still further aspect, the entire microneedle is dissolvable. In yet a further aspect, a portion of the microneedle is dissolvable such as, for example, the tip of the microneedle. Thus, in various aspects, the microneedles dissolve at a rate of from about One minute per patch to about one month per patch. In a further aspect, the microneedles dissolve at a rate of from about one minute per patch to about two weeks per patch. In a still further aspect, the microneedles dissolve at a rate of from about one minute per patch to about one week per patch. In yet a further aspect, the microneedles dissolve at a rate of from about one minute per patch to about 3 days per patch. In an even further aspect, the microneedles dissolve at a rate of from about one minute per patch to about one day per patch. In a still further aspect, the microneedles dissolve at a rate of from about one minute per patch to about 12 hours per patch. In yet a further aspect, the microneedles dissolve at a rate of from about one minute per patch to about 6 hours per patch. In an even further aspect, the microneedles dissolve at a rate of from about one minute per patch to about one hour per patch. In a still further aspect, the microneedles dissolve at a rate of from about one minute per patch to about 30 minutes per patch. In yet a further aspect, the microneedles dissolve at a rate of from about 30 minutes per patch to about one month per patch. In an even further aspect, the microneedles dissolve at a rate of from about one hour per patch to about one month per patch. In a still further aspect, the microneedles dissolve at a rate of from about 6 hours per patch to about one month per patch. In yet a further aspect, the microneedles dissolve at a rate of from about 12 hours per patch to about one month per patch. In an even further aspect, the microneedles dissolve at a rate of from about one day per patch to about one month per patch. In a still further aspect, the microneedles dissolve at a rate of from about 3 days per patch to about one month per patch. In yet a further aspect, the microneedles dissolve at a rate of from about one week per patch to about one month per patch. In yet a further aspect, the microneedles dissolve at a rate of from about two weeks per patch to about one month per patch.

In a further aspect, the microneedles dissolve at a rate of less than about one minute per patch. In a still further aspect, the microneedles dissolve at a rate of from about 1 second per patch to about one minute per patch. In yet a further aspect, the microneedles dissolve at a rate of from about 1 second per patch to about thirty seconds per patch. In an even further aspect, the microneedles dissolve at a rate of from about 1 second per patch to about 10 seconds per patch. In a still further aspect, the microneedles dissolve at a rate of from about 10 seconds per patch to about one minute per patch. In yet a further aspect, the microneedles dissolve at a rate of from about 30 seconds per patch to about one minute per patch.

In a further aspect, the microneedles are biodegradable and/or bioabsorbable. In a still further aspect, the microneedles are biodegradable. In yet a further aspect, the microneedles are bioabsorbable. In an even further aspect, the microneedles are biodegradable and bioabsorbable.

In a further aspect, the microneedles comprise a biodegradable and/or bioabsorbable polymer. In a still further aspect, the microneedles comprise at least two biodegradable and/or bioabsorbable polymers. In yet a further aspect, the polymer is selected from poly(ethylene glycol), poly(caprolactone), and polyacrylic acid, or a combination thereof.

In a further aspect, the microneedles comprise a therapeutic agent. In a further aspect, the therapeutic agent comprises a protein therapeutic or a small molecule therapeutic. In yet a further aspect, the therapeutic agent is coated onto or dispersed in said microneedles. In an even further aspect, the therapeutic agent is coated onto the microneedles. In a still further aspect, the therapeutic agent is dispersed in the microneedles.

In a further aspect, the therapeutic agent is released from the microneedles. The release of the therapeutic agent may occur upon insertion or over a period of time. For example, in various aspects, the therapeutic agent may be released from the microneedle over a time period of about 1 minute to about 6 months. In a further aspect, the therapeutic agent may be released from the microneedle over a time period of about 1 minute to about 3 months. In a still further aspect, the therapeutic agent may be released from the microneedle over a time period of about 1 minute to about 1 month. In yet a further aspect, the therapeutic agent may be released from the microneedle over a time period of about 1 minute to about 2 weeks. In an even further aspect, the therapeutic agent may be released from the microneedle over a time period of about 1 minute to about 1 week. In a still further aspect, the therapeutic agent may be released from the microneedle over a time period of about 1 minute to about 3 days. In yet a further aspect, the therapeutic agent may be released from the microneedle over a time period of about 1 minute to about 1 day. In an even further aspect, the therapeutic agent may be released from the microneedle over a time period of about 1 minute to about 12 hours. In a still further aspect, the therapeutic agent may be released from the microneedle over a time period of about 1 minute to about 6 hours. In yet a further aspect, the therapeutic agent may be released from the microneedle over a time period of about 1 minute to about 1 hour. In an even further aspect, the therapeutic agent may be released from the microneedle over a time period of about 1 minute to about 30 minutes. In a still further aspect, the therapeutic agent may be released from the microneedle over a time period of about 30 minutes to about 6 months. In yet a further aspect, the therapeutic agent may be released from the microneedle over a time period of about 1 hour to about 6 months. In an even further aspect, the therapeutic agent may be released from the microneedle over a time period of about 6 hours to about 6 months. In a still further aspect, the therapeutic agent may be released from the microneedle over a time period of about 12 hours to about 6 months. In yet a further aspect, the therapeutic agent may be released from the microneedle over a time period of about 1 day to about 6 months. In an even further aspect, the therapeutic agent may be released from the microneedle over a time period of about 3 days to about 6 months. In a still further aspect, the therapeutic agent may be released from the microneedle over a time period of about 1 week to about 6 months. In yet a further aspect, the therapeutic agent may be released from the microneedle over a time period of about 2 weeks to about 6 months. In an even further aspect, the therapeutic agent may be released from the microneedle over a time period of about 1 month to about 6 months. In a still further aspect, the therapeutic agent may be released from the microneedle over a time period of about 3 months to about 6 months.

In a further aspect, the therapeutic agent may be released from the microneedle over a time period of less than about 1 minute. In a still further aspect, the therapeutic agent may be released from the microneedle over a time period of about 1 second to about 1 minute. In yet a further aspect, the therapeutic agent may be released from the microneedle over a time period of about 1 second to about 30 seconds. In an even further aspect, the therapeutic agent may be released from the microneedle over a time period of about 1 second to about 10 seconds. In a still further aspect, the therapeutic agent may be released from the microneedle over a time period of about 10 seconds to about 1 minute. In yet a further aspect, the therapeutic agent may be released from the microneedle over a time period of about 30 seconds to about 1 minute.

1. Breakable Microneedles

In a further aspect, disclosed are breakable microneedles. A microneedle may be breakable, for example, due to the shape of the microneedle (e.g., due to the presence of holes or a thinner structure). Alternatively, a microneedle may be breakable due to a difference in the mechanical properties of the support, as compared to the remainder of the microneedle.

A breakable microneedle may be broken intentionally to remove the microneedles embedded in the skin from the patch backing on the skin surface. Without wishing to be bound by theory, removal of the patch backing may improve patient comfort. Moreover, removal of the patch backing may allow for verification that the intended payload is delivered to the sample and/or subject by ensuring that none of the therapeutic (or what amount of therapeutic) is present on the breakable support after patch administration.

In a further aspect, the microneedles comprise breakable supports. As used herein, "breakable" is capable of being broken.

In various aspects, breakable is via a breakable support. Thus, in various aspects a microneedle sidewall may comprise at least one breakable support. For example, the support may resist breaking under application of a normal force, but allow separation through torsion, shearing, or other energy inputs. In a still further aspect, the microneedles comprise a sidewall comprising a breakable support.

In various aspects, breakable is via a perforation such as, for example, a physical perforation or a chemical perforation.

In a further aspect, the microneedles comprise a perforated sidewall. As used herein, a "perforation" refers to a specific plane within the microneedle that is chemically or physically distinct from the remainder of the array. In this way, one part of the microneedle (e.g., the tip) may be separated from the rest of the microneedle (e.g., the base). In various aspects, a perforation includes a hole or slit. In various aspects a microneedle sidewall may comprise at least one perforation.

In a further aspect, the sidewall is physically perforated. For example, a sidewall may be physically perforated by computer design.

In a further aspect, the sidewall is chemically perforated. For example, a sidewall may be chemically perforated by a water soluble material. Thus, in various aspects, chemically perforated may be dissolvable. In a further aspect, chemically perforated may be mechanically distinct.

Microneedles that can be mechanically or chemically fragmented or removed from the backing are useful in that they allow for rapid administration of therapeutics that have long term drug release without the long term patch application. For example, if a needle patch composition is designed to release drug over a period of one week, then breakable microneedles could be applied to the skin, fragmented, and the patch backing removed, with the microneedle fragments embedded in the skin to release drug. This could afford patients the benefit of long-term drug delivery without the need to wear a patch for the entire duration of therapy. Below are examples of breakable microneedle designs that can be formed from additive manufacturing as taught herein.

a. Breakable Microneedles having Physical Supports

In a further aspect, the microneedles comprise a sidewall comprising a breakable support. The breakable support may be made up of the same material as the rest of the microneedle. Alternatively, the breakable support may be made up of a different material than the rest of the microneedle.

Thus, in various aspects, microneedles are formed with supports that resist breaking under application of a normal force to the patch backing, but allow separation through torsion, shearing, or other energy inputs (sound, heat, light, pressure) (FIG. 1A-I). This design would leave a portion(s) of the needle embedded in the skin after patch removal depending on where the breakable supports are positioned.

In a further aspect, of from about 0.1% to about 99% of the sidewall comprises a breakable support. In a still further aspect, of from about 0.1% to about 90% of the sidewall comprises a breakable support. In yet a further aspect, of from about 0.1% to about 75% of the sidewall comprises a breakable support. In an even further aspect, of from about 0.1% to about 50% of the sidewall comprises a breakable support. In a still further aspect, of from about 0.1% to about 25% of the sidewall comprises a breakable support. In yet a further aspect, of from about 0.1% to about 10% of the sidewall comprises a breakable support. In an even further aspect, of from about 0.1% to about 5% of the side-wall comprises a breakable support. In a still further aspect, of from about 0.1% to about 1% of the sidewall comprises a breakable support. In yet a further aspect, of from about 1% to about 99% of the sidewall comprises a breakable support. In an even further aspect, of from about 5% to about 99% of the sidewall comprises a breakable support. In a still further aspect, of from about 10% to about 99% of the sidewall comprises a breakable support. In yet a further aspect, of from about 25% to about 99% of the sidewall comprises a breakable support. In an even further aspect, of from about 50% to about 99% of the sidewall comprises a breakable support. In a still further aspect, of from about 75% to about 99% of the sidewall comprises a breakable support. In yet a further aspect, of from about 90% to about 99% of the sidewall comprises a breakable support.

In a further aspect, all of the microneedles on the array comprise a sidewall comprising a breakable support. In a still further aspect, at least about 75% of the microneedles on the array comprise a sidewall comprising a breakable support. In yet a further aspect, at least about 50% of the microneedles on the array comprise a sidewall comprising a breakable support. In an even further aspect, at least about 25% of the microneedles on the array comprise a sidewall comprising a breakable support. In a still further aspect, at least about 15% of the microneedles on the array comprise a sidewall comprising a breakable support. In yet a further aspect, at least about 10% of the microneedles on the array comprise a sidewall comprising a breakable support. In an even further aspect, at least about 5% of the microneedles on the array comprise a sidewall comprising a breakable support. In a still further aspect, a single microneedle on the array comprises a sidewall comprising a breakable support.

b. Breakable Microneedles having Physical Perforations

In a further aspect, the microneedles comprise a physically perforated Thus, in various aspects, microneedles are formed with physical perforated sidewalls that resist breaking under application of a Normal force to the patch backing, but allow separation through torsion, shearing, or other energy inputs (sound, heat, light, pressure) (FIG. 2A-G). This design differs from the support model in that tiny portions of the needle would be omitted through computer design to make perforations in the existing needle structure rather than adding material in the form of supports. The effect would be similar in that portion(s) of the needle would remain embedded in the skin after patch removal depending on where the perforations were designed.

In a further aspect, of from about 0.1% to about 99% of the sidewall is physically perforated. In a still further aspect, of from about 0.1% to about 90% of the sidewall is physically perforated. In yet a further aspect, of from about 0.1% to about 75% of the sidewall is physically perforated. In an even further aspect, of from about 0.1% to about 50% of the sidewall is physically perforated. In a still further aspect, of from about 0.1% to about 25% of the sidewall is physically perforated. In yet a further aspect, of from about 0.1% to about 10% of the sidewall is physically perforated. In an even further aspect, of from about 0.1% to about 5% of the sidewall is physically perforated. In a still further aspect, of from about 0.1% to about 1% of the sidewall is physically perforated. In yet a further aspect, of from about 1% to about 99% of the sidewall is physically perforated. In an even further aspect, of from about 5% to about 99% of the sidewall is physically perforated. In a still further aspect, of from about 10% to about 99% of the sidewall is physically perforated. In yet a further aspect, of from about 25% to about 99% of the sidewall is physically perforated. In an even further aspect, of from about 50% to about 99% of the sidewall is physically perforated. In a still further aspect, of from about 75% to about 99% of the sidewall is physically perforated. In yet a further aspect, of from about 90% to about 99% of the sidewall is physically perforated.

In a further aspect, all of the microneedles on the array comprise a physically perforated sidewall. In a still further aspect, at least about 75% of the microneedles on the array comprise a physically perforated sidewall. In yet a further aspect, at least about 50% of the microneedles on the array comprise a physically perforated sidewall. In an even further aspect, at least about 25% of the microneedles on the array comprise a physically perforated sidewall. In a still further aspect, at least about 15% of the microneedles on the array comprise a physically perforated sidewall. In yet a further aspect, at least about 10% of the microneedles on the array comprise a physically perforated sidewall. In an even further aspect, at least about 5% of the microneedles on the array comprise physically perforated sidewall. In a still further aspect, a single microneedle on the array comprises a physically perforated sidewall.

c. Breakable Microneedles having Chemical Perforations

In a further aspect, the microneedles comprise a chemically perforated sidewall. Thus, in various aspects, microneedles are formed with chemical perforations that can break down in the skin, allowing for separation through physical (e.g., dissolving, swelling, or cracking), chemical (e.g., pH or oxidation) or enzymatic breakdown (biologically triggered) (FIG. 3A-G). This design would leave a portion(s) of the needle embedded in the skin after patch removal depending on where the chemical perforation is positioned.

In a further aspect, chemically perforated is via a chain-transfer agent. For example, a chain-transfer agent may reduce the size of the polymer chain. Without wishing to be bound by theory, the chain-transfer agent may improve the solubility of the polymer chain. In a still further aspect, the chain-transfer agent is selected from N-acetyl cysteine, cysteine, dithiothreitol, 2-mercaptoethanol, isopropanol, and ethanol.

In a further aspect, of from about 0.1% to about 99% of the sidewall is chemically perforated. In a still further aspect, of from about 0.1% to about 90% of the sidewall is chemically perforated. In yet a further aspect, of from about 0.1% to about 75% of the sidewall is chemically perforated. In an even further aspect, of from about 0.1% to about 50% of the sidewall is chemically perforated. In a still further aspect, of from about 0.1% to about 25% of the sidewall is chemically perforated. In yet a further aspect, of from about 0.1% to about 10% of the sidewall is chemically perforated. In an even further aspect, of from about 0.1% to about 5% of the sidewall is chemically perforated. In a still further aspect, of from about 0.1% to about 1% of the sidewall is chemically perforated. In yet a further aspect, of from about 1% to about 99% of the sidewall is chemically perforated, in an even further aspect, of from about 5% to about 99% of the sidewall is chemically perforated. In a still further aspect, of from about 10% to about 99% of the sidewall is chemically perforated. In yet a further aspect, of from about 25% to about 99% of the sidewall is chemically perforated. In an even further aspect, of from about 50% to about 99% of the sidewall is chemically perforated. In a still further aspect, of from about 75% to about 99% of the sidewall is chemically perforated. In yet a further aspect, of from about 90% to about 99% of the sidewall is chemically perforated.

In a further aspect, all of the microneedles on the array comprise a chemically perforated sidewall. In a still further aspect, at least about 75% of the microneedles on the array comprise a chemically perforated sidewall. In yet a further aspect, at least about 50% of the microneedles on the array comprise a chemically perforated sidewall. In an even further aspect, at least about 25% of the microneedles on the array comprise a chemically perforated sidewall. In a still further aspect, at least about 15% of the microneedles on the array comprise a chemically perforated sidewall. In yet a further aspect, at least about 10% the microneedles on the array comprise a chemically perforated sidewall. In an even further aspect, at least about 5% of the microneedles on the array comprise chemically perforated sidewall. In a still further aspect, a single microneedle on the array comprises a chemically perforated sidewall.

2. Undercut Microneedle Structures

In a further aspect, the microneedles comprise an undercut sidewall.

Microneedle insertion into the skin has been modeled in three distinct phases: insertion, penetration and relaxation. Briefly, the insertion phase spans the period of time from initial contact with the skin until skin breach, penetration spans the time from skin breach until the time at which the maximum penetration depth is reached, and relaxation encompasses the period of time from when the applied insertion force is removed until the needle has reached steady state. In this relaxation phase, the skin's natural elastic properties typically push needles back out of the skin. While some studies have focused on decreasing forces of insertion, few attempts have been made to prevent microneedles from relaxing out of the skin. Utilizing additive manufacturing to make arrowhead or other "undercut" microneedles provides the opportunity to produce microneedles that remain deep within the skin at a specified penetration depth.

Exemplary structural aspects may be found in, for example, patents EP 1 465 535 B1, WO 2008053481 A1, US 2014/0005606 A1, WO2012100002 A1 and the publication "Separable Arrowhead Microneedles" (Chu et. al., Journal of Controlled Release, 149(3):242-249, 2011), O2012100002 A1, US20140170299, and EP 1 465 535 B1 contain undercut microneedles that are produced using "in-plane" and "out-of-plane" techniques, wherein a two dimensional sheet is cut and may then be folded to produce a semi-three dimensional structure. However, each microneedle produced using such techniques is a flat structure that exists within a single spatial plane. A three-dimensional microneedle cannot be produced using "in-plane" and "out-of-plane" approaches, Flat, semi-three dimensional structures such as the folded arrowhead structures in patent US20140170299 are likely to be weaker than a true three-dimensional structure comprised of an equivalent material because of these mechanical limitations. These techniques are typically used to fabricate metal microneedles, which may pose immunological hazards to patients. Further, the semi-three dimensional structure produced using previous techniques limits available cargo loading volume. Chu et. al. demonstrate the ability to produce water soluble arrowhead microneedles using a two-step process, wherein the microneedle tip is filled with a mixture of PVP and PVA. An array of metal shafts are then manually inserted into this mixture to create an arrowhead microneedle. This technique is a multi-step manual batch process that utilizes non-biocompatible materials. In US 2014/0005606 A1, a molding-based method of producing purely biodegradable microneedles is proposed. It is unclear, however, how such undercut structures are removed from a mold. This molding-based process is also subject to the lengthy fabrication times mentioned previously.

3. Tiered Microneedles

Figure 4A:
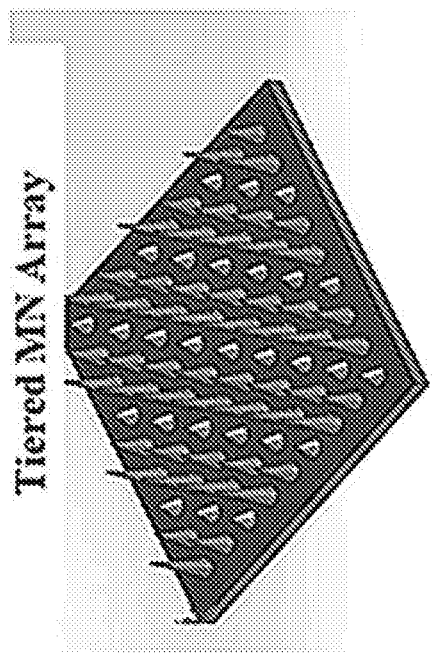
FIG. 4A and FIG. 4B show representative schematics of a traditional microneedle array and theoretical force of insertion (4A) and a tiered microneedle array and theoretical force of insertion (4B).
Figure 4B:
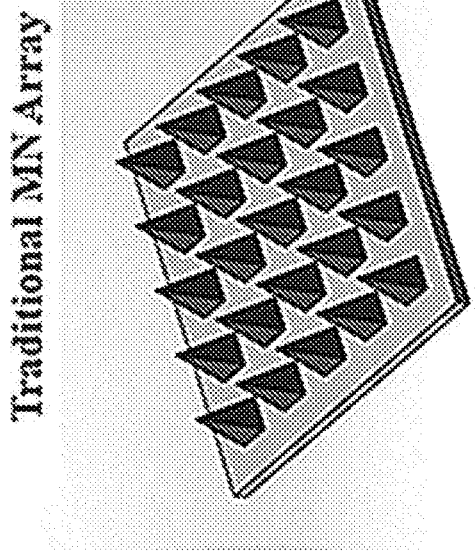

In a further aspect, the microneedles are tiered. As used herein, "tiered" refers to an array of microneedles containing microneedles of multiple different heights. Thus, in various aspects, microneedle patches are provided in which microneedles of multiple different heights are included on a single array ("Tiered Microneedles"). Without wishing to be bound by theory, these microneedles may counteract the "bed-of-nails" effect, in which the force of insertion on a microneedle array is distributed among the individual needles in the array, thereby limiting the total amount of force that can be applied to a single needle (FIG. 4A). Using CLIP to produce an array in which multiple microneedle heights are represented on a single patch (FIG. 4B) enables this force to be concentrated on a smaller number of needles at a given time, thereby reducing the total force required for insertion (Table 1). Ideally, these microneedles would enable facile insertion into the skin using small forces, such as the force of thumb. Without wishing to be bound by theory, small insertion forces should allow microneedles to be fabricated from a wider variety of materials and to insert more deeply into the skin.

TABLE 1

| Number of Layers | Force Required for Insertion* |
| --- | --- |
| 1 | F |
| 3 | F/3 |
| 4 | F/4 |
| n | F/n |

*assumes equal number of needles per tier

In various aspects, a tiered array may comprise microneedles at two or more different heights. In a further aspect, a tiered array may comprise microneedles at two or more different heights. In a still further aspect, a tiered array may comprise microneedles at three or more different heights. In yet a further aspect, a tiered array may comprise microneedles at four or more different heights. In an even further aspect, a tiered array may comprise microneedles at five or more different heights. In a still further aspect, a tiered array may comprise microneedles at six or more different heights. In yet a further aspect, a tiered array may comprise microneedles at seven or more different heights. In an even further aspect, a tiered array may comprise microneedles at eight or more different heights. In a still further aspect, a tiered array may comprise microneedles at nine or more different heights. In yet a further aspect, a tiered array may comprise microneedles at ten or more different heights.

In a further aspect, the different heights may be arranged randomly, in a still further aspect, the different heights may be arranged from shortest to tallest. In yet a further aspect, the different heights may be arranged via alternating rows. In an even further aspect, the different heights may be arranged together such as, for example, dividing the array in half (i.e., half one height and half the other height).

In a further aspect, the microneedles may differ in height by a ratio of at least about 1 to 100. In a still further aspect, the microneedles may differ in height by a ratio of at least about 1 to 80. In yet a further aspect, the microneedles may differ in height by a ratio of at least about 1 to 60. In an even further aspect, the microneedles may differ in height by a ratio of at least about 1 to 50. In a still further aspect, the microneedles may differ in height by a ratio of at least about 1 to 40. In yet a further aspect, the microneedles may differ in height by a ratio of at least about 1 to 20. In an even further aspect, the microneedles may differ in height by a ratio of at least about 1 to 10. In a still further aspect, the microneedles may differ in height by a ratio of at least about 1 to 5. In yet a further aspect, the microneedles may differ in height by a ratio of at least about 1 to 2. In an even further aspect, the microneedles may differ in height by a ratio of at least about 1 to 1.5. In a still further aspect, the microneedles may differ in height by a ratio of at least about 1 to 1.05. In yet a further aspect, the microneedles may differ in height by a ratio of at least about 1 to 1.005. In an even further aspect, the microneedles may differ in height by a ratio of at least about 1 to 1,0005.

4. Microneedles with Curved or Discontinuous Sidewall Profiles

In a further aspect, the microneedles comprise a curved or discontinuous sidewall. In a still further aspect, the microneedles comprise a curved sidewall. In yet a further aspect, the microneedles comprise a discontinuous sidewall.

Figure 5A:
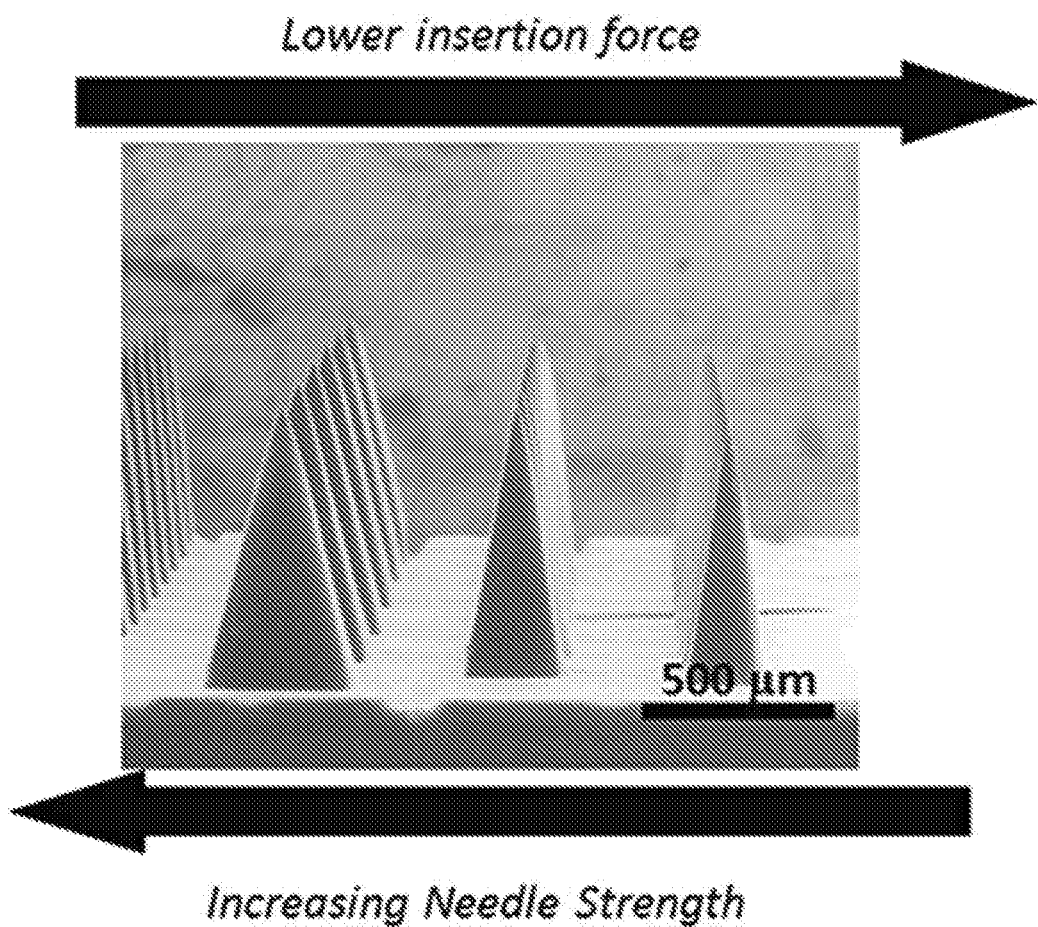
FIG. 5A-D shows representative images of CLIP microneedles with square pyramidal (5A), curved (5B and 5C), and discontinuous (5D) sidewalls.

Some traditional microneedle fabrication techniques (such as tilted LV photolithography) are limited to producing microneedles with a straight sidewall profile. When square pyramidal microneedles are used (shown in FIG. 5A) an inherent tradeoff exists between reducing the force required to insert the needle and improving needle strength. Due to these challenges, high aspect ratio microneedles are subject to buckling.

Figure 5C:
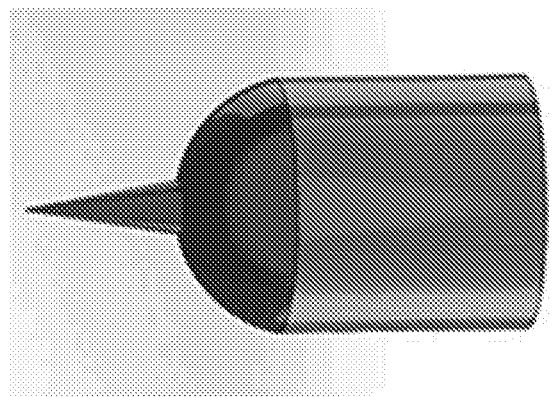
Figure 5B:
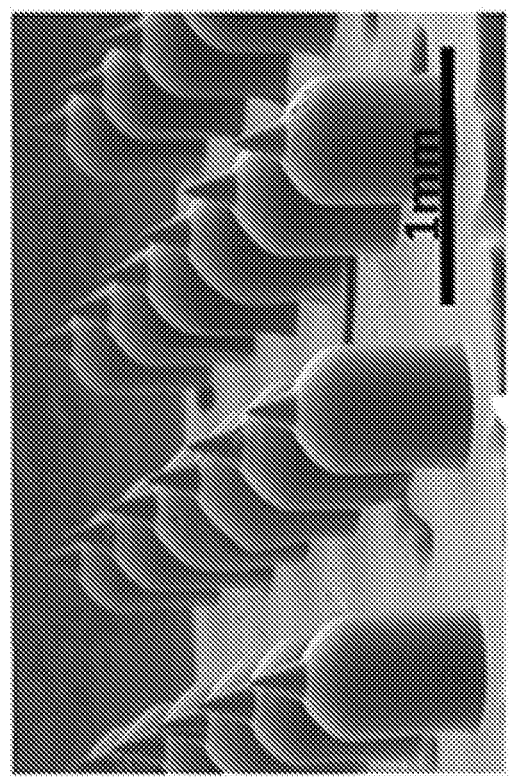
Figure 5D:
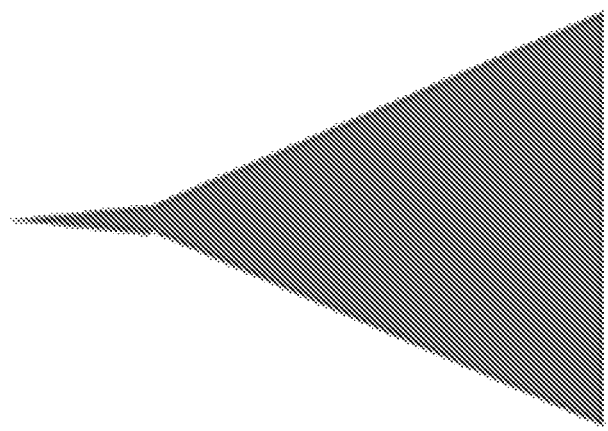
Figure 5D:
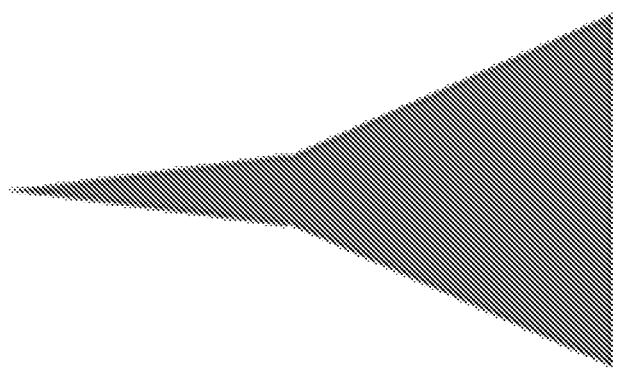
Figure 5D:
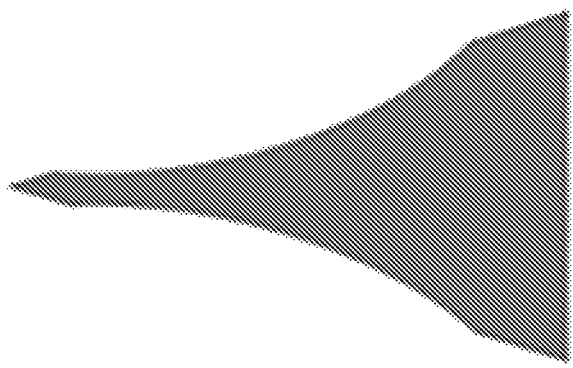

Thus, in various aspects, microneedles are fabricated with curved or discontinuous sidewall profiles (FIG. 5B-D). Without wishing to be bound by the theory, the sharp, narrow tip may allow for insertion into the skin with minimal force because the force required for microneedle insertion decreases with tip sharpness. Once the skin has been breached, the wider, more stable microneedle could effectively insert into the skin without fracture.

5. Microneedles with Complex X-Y Cross-Sections

In a further aspect, the microneedles comprise a cross-section that is non-circular and non-polygonal. Thus, in various aspects, microneedles are fabricated with complex X-Y cross-sections. For example, microneedles may a cross-section that is non-circular or non-polygonal (e.g., non-square, non-rectangle, non-triangular, etc.) in shape in at least a part of the length thereof. Exemplary, non-circular and non-polygonal shapes include, but are not limited to, a star, a cross, a heart, a cone, and a partial sphere (e.g., moon).

Figure 6A:
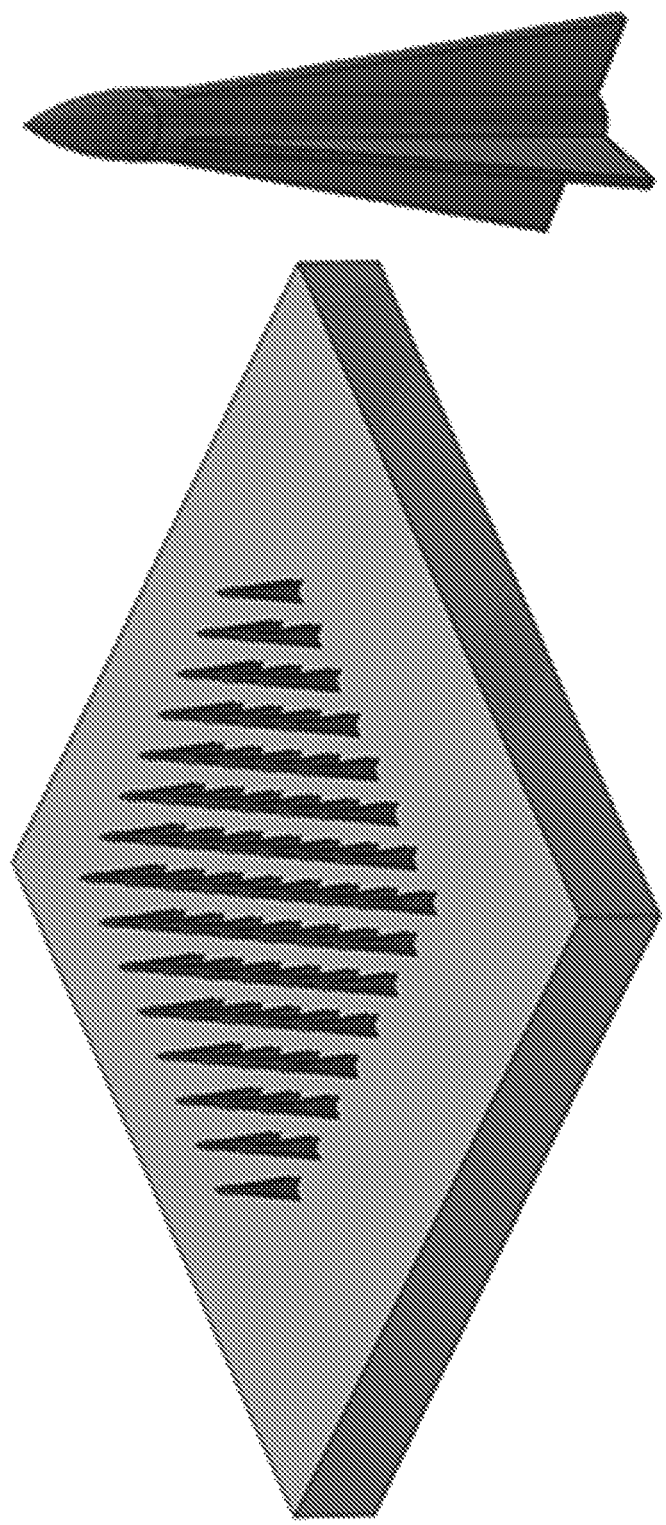
FIG. 6A shows a representative image of a microneedle array comprising microneedles having complex X-Y cross sections.
Figure 6B:
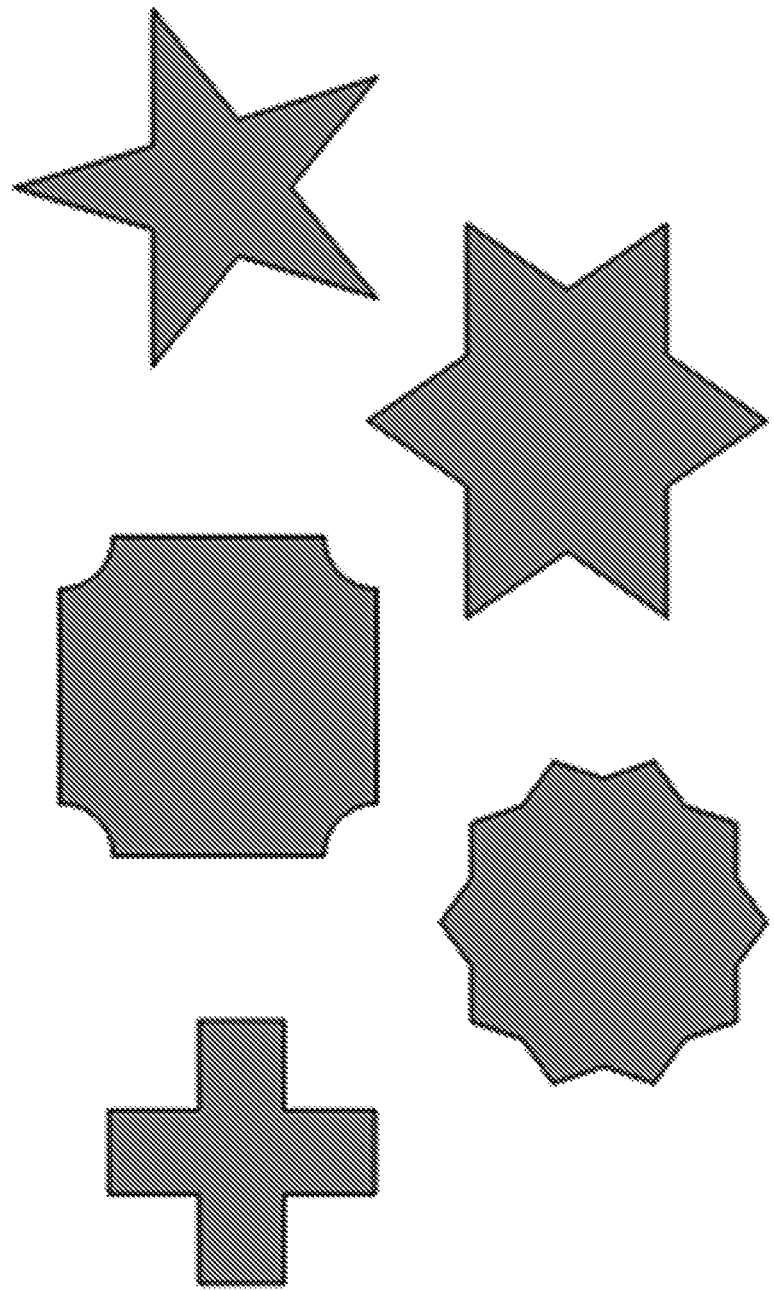
FIG. 6B shows representative images of exemplary non-circular and non-polygonal X-Y cross-sections.

Some common mechanical models correlate the amount of energy required to insert a microneedle into the skin with the volume of tissue that must be deformed during its insertion. Because it may be desirable to insert microneedles into the skin at a specific penetration depth (for targeting certain cell types, accessing the bloodstream, etc.), it may be desirable to produce microneedles that have limited volume for a given height, enabling the amount of force required to insert the needle to a given depth to be reduced. An example of such a design is shown in FIG. 6A. In this specific example, a microneedle with "fins" is designed to maintain the mechanical strength of a tall microneedle. The cutouts between fins reduce the amount of tissue that needs to be deformed to effectively insert this needle into the skin at a given depth. A number of other similar microneedles may be fabricated. Exemplary potential non-circular and non-polygonal cross-sections may include, but are not limited to, those shown in FIG. 6B.

C. METHODS OF MAKING MICRONEEDLES WITH ADDITIVE MANUFACTURING

In one aspect, disclosed are methods of making a disclosed microneedle device.

In one aspect, disclosed are methods of making a microneedle device, the method comprising the steps of: (a) providing a build elevator and an optically transparent build surface, wherein the build elevator and the build surface together define a build region there between, wherein the build surface is permeable to a polymerization inhibitor, and wherein the build surface is in fluid communication with a source of the polymerization inhibitor; (h) filling the build region with a polymerizable liquid; (c) irradiating the build region through the build surface to produce a solid polymerized region in the build region; (d) forming or maintaining a liquid film release layer between the solid polymerized region and the build surface, wherein the liquid film release layer comprises the polymerizable liquid, and wherein the polymerization of the liquid is inhibited by the polymerization inhibitor; and (e) advancing the build elevator away from the build surface to create a subsequent build region between the solid polymerized region and the build surface while concurrently filling the subsequent build region with the polymerizable liquid, wherein the device comprises: (f) a backing; and (g) a plurality of biocompatible microneedles projecting from the backing, wherein the microneedles comprise one or more of: (i) a curved, discontinuous, undercut, or perforated sidewall (ii) a sidewall comprising a breakable support; and (iii) a cross-section that is non-circular and non-polygonal, and/or wherein the microneedles are tiered, thereby making the microneedle device.

In one aspect, disclosed are methods of making a disclosed microneedle device, comprising the steps of: (a) providing a build elevator and an optically transparent build surface defining a build region there between, said build surface being permeable to a polymerization inhibitor, and with said build surface in fluid communication with a source of the polymerization inhibitor; (b) filling said build region with a polymerizable liquid, said polymerizable liquid contacting said build surface; (c) irradiating said build region through said build surface to produce a solid polymerized region in said build region, while forming or maintaining a liquid film release layer comprised of said polymerizable liquid formed between said solid polymerized region and said build surface, wherein the polymerization of which liquid film is inhibited by said polymerization inhibitor; and (d) advancing said build elevator with said polymerized region adhered thereto away from said build surface to create a subsequent build region between said polymerized region and said build surface while concurrently filling said subsequent build region with polymerizable liquid as in step (b), to thereby form said microneedle device. In a further aspect, the method further comprises (e) continuing and/or repeating steps (c) and (d) to produce a subsequent polymerized region adhered to a previous polymerized region until the continued or repeated deposition of polymerized regions adhered to one another forms said microneedle device. In a still further aspect, steps (c) and (d) are carried out concurrently.

Figure 7A:
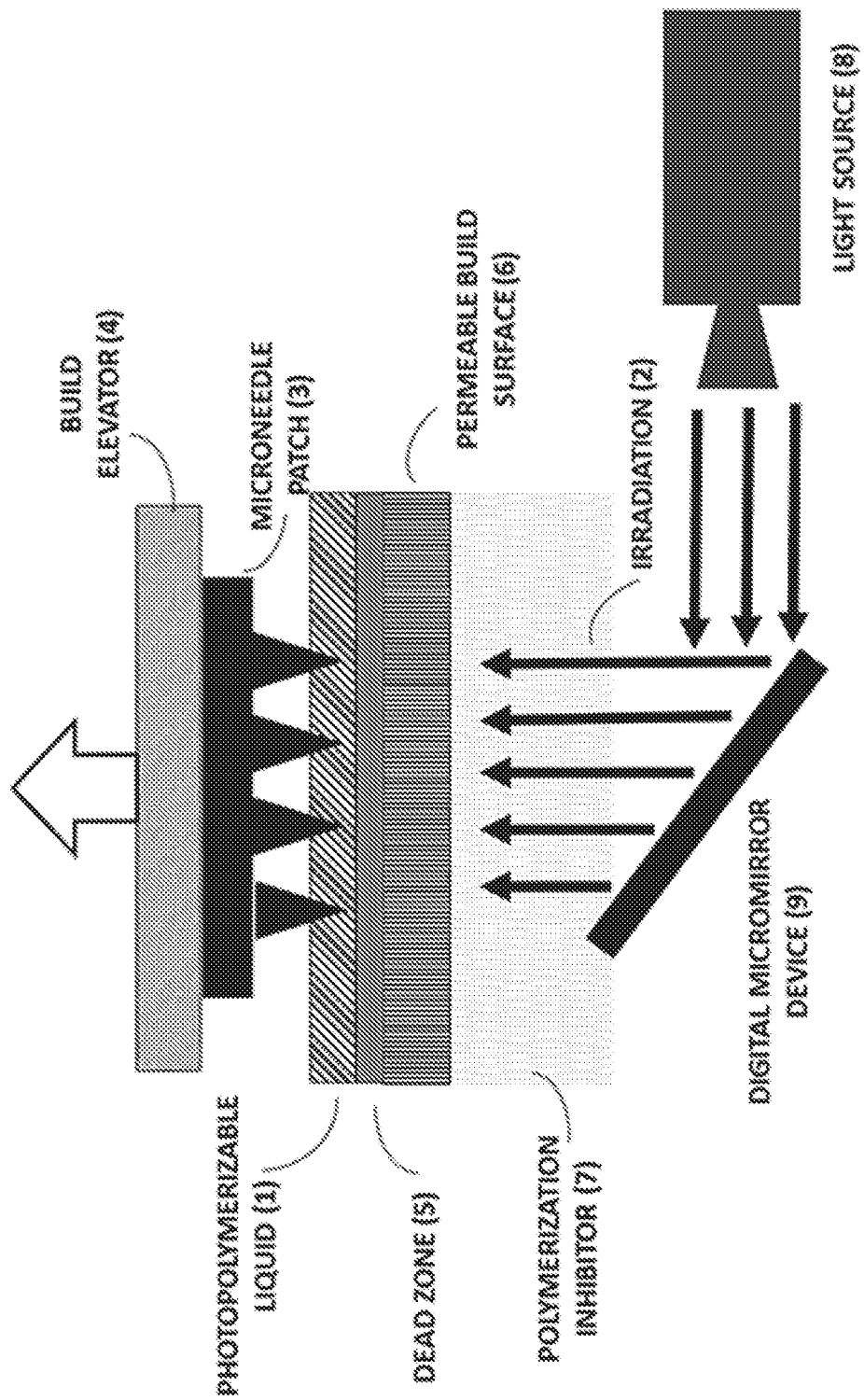
FIG. 7A shows a representative schematic of a Continuous Liquid interface Printer (CLIP).

Aspects of the polymeric microneedles as taught herein may be fabricated with a continuous liquid interface printing (CLIP) apparatus, including, but not limited, to those described in PCT application publication WO 2014/126837 to DeSimone et al., the contents of which are incorporated by reference herein in its entirety. A representative diagram of the CLIP process is shown in FIG. 7A. A photopolymerizable liquid is illuminated with radiation in a shape defined by a computational file (.svg, .ctl, bitmap, etc.) of a microneedle patch. As the photopolymerizable liquid is exposed to radiation, the microneedle patch attaches to build elevator 4, which pulls the part through the liquid resin with a substantially continuous upward movement. Unlike other additive manufacturing approaches, where separation, recoating, and repositioning steps are required between each sequential layer, CLIP enables continuous (i.e., not layer-by-layer) generation of the part through the generation of a liquid "dead zone" at the interface between the permeable build surface and the building microneedle patch. Without wishing to be bound by theory, the dead zone may be created when oxygen, which acts as a polymerization inhibitor, passes through the oxygen-permeable build surface. Because photopolymerization cannot occur in the oxygen containing region ("dead zone"), this region remains fluid, and the building part does not physically attach to the build surface. Irradiation may be generated using, for example, a UV LED light source reflecting off of a digital micromirror device.

Figure 7C:
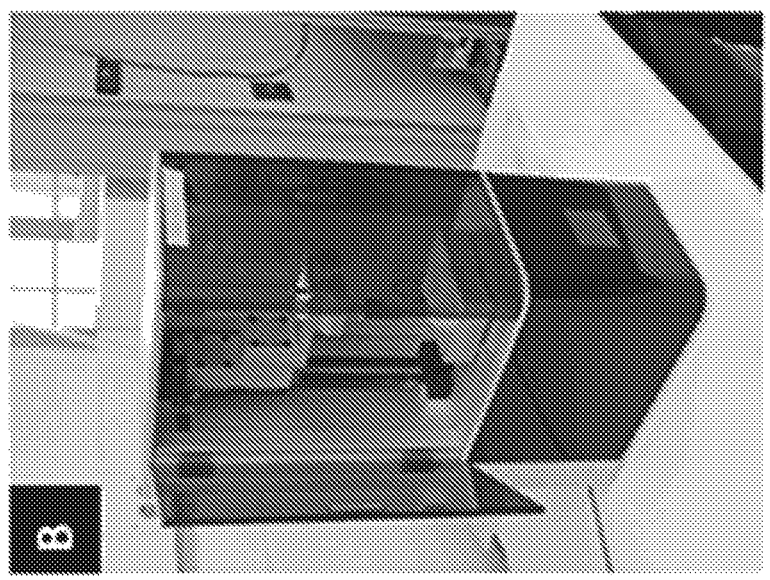
FIG. 7B and FIG. 7C show a representative CLIP7 (7B) and CLIP Mini (7C).
Figure 7B:
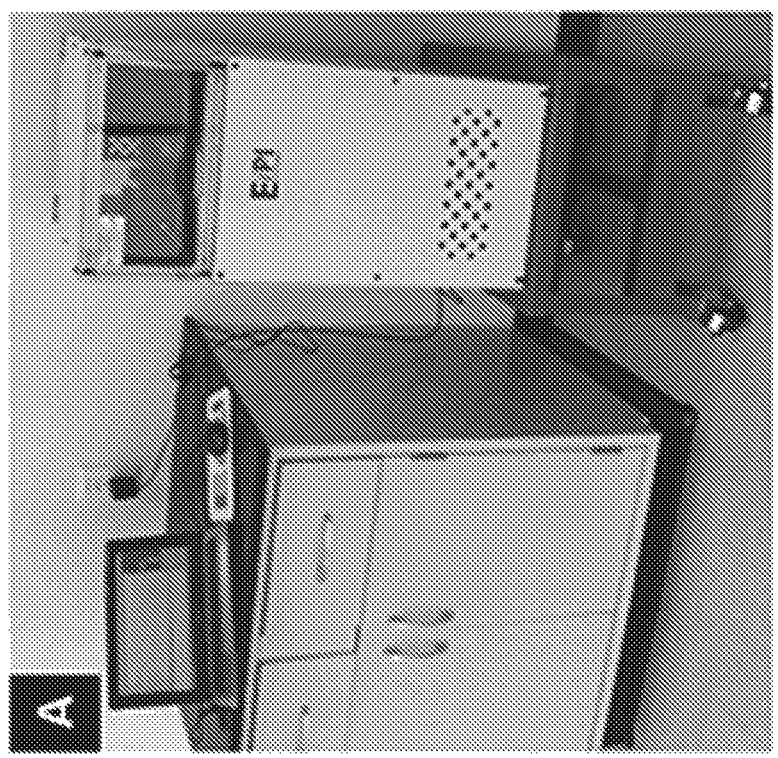

Two examples of CLIP printers and their respective dimensions are shown in FIG. 7B and FIG. 7C and Table 1. These two instruments serve as examples of CLIP printers, but a number of different alternative systems could be utilized. For example, while air is utilized as a photopolymerization inhibitor in these systems, an alternative inhibitor such as pure oxygen or ammonia could also be used. Furthermore, while these systems use ultraviolet light, a number of alternative light sources with irradiation at any point on the electromagnetic spectrum visible, nearIR, gamma radiation, etc.) could be utilized.

Figures 8A, 8B:
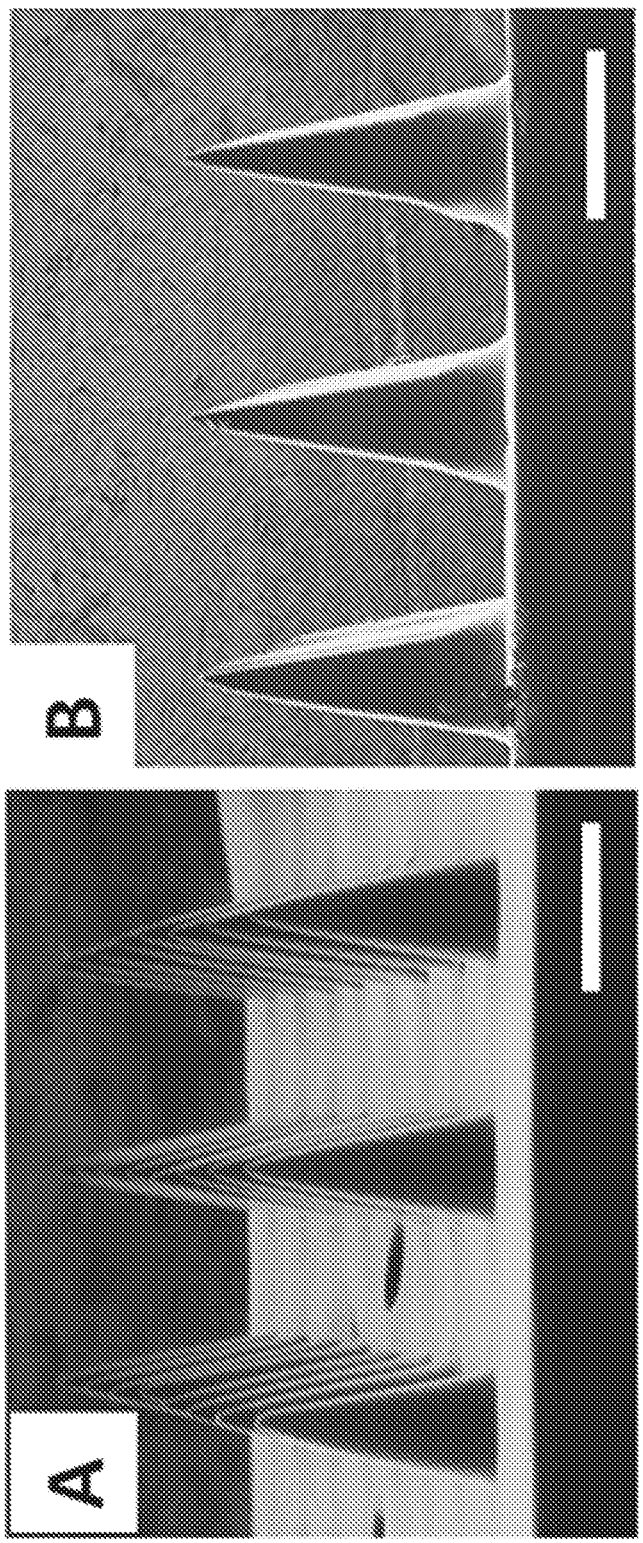
FIG. 8A-C show representative fabricated microneedle compositions. Specifically, polyacrylic acid microneedles (8A), polyethylene glycol microneedles (8B), and polycaprolactone microneedles (8C) measuring 1000 µm in height and 333 µm in width are shown. Scale bars measure 500 µm.
Figure 8C:
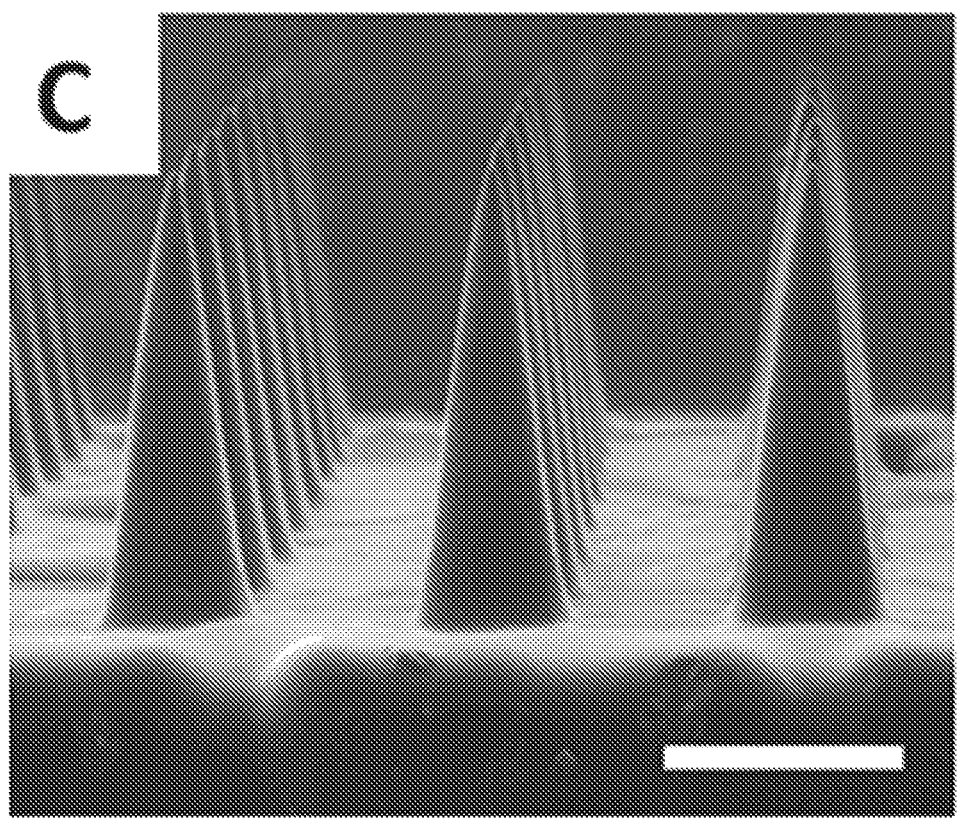

Selection of microneedle compositions may be based on a number of different factors including, but not limited to, solubility, biocompatibility, swelling or degradation kinetics, or mechanical properties, among many others. Exemplary microneedles have been fabricated from a number of compositions such as polyethylene glycol, polyacrylic acid, and polycaprolactone, as shown in FIG. 8A-C.

A number of other materials could also be utilized for the formation of microneedles as taught herein. Some examples include, but are not limited to, polyesters (polycaprolactone, polyalycolic acid, polylactic acid, polylactic-co-glycolic acid), poly ethers (polyethylene glycol), thiol-enes, anhydrides, acrylate polymers (polyacrylic acid, poly methylmethacrylate), vinyl polymers (polyvinyl alcohol, polyvinylpyrrolidone, vinyl carbonates, vinyl esters), acrylamides, natural polymers (hyaluronic acid, chitosan, collagen, gelatin, carboxymethylcellulose), etc. Blends or copolymers of aforementioned materials may be generated to tune material properties. Any of these materials may or may not be functionalized with photoreactive groups. A blend of photoreactive monomer with a non-photoreactive monomer may be utilized, for example, to generate porous needles.

In various aspects, the disclosed microneedles may contain two or more different sections of spatially distinct compositions (as opposed to a copolymer blend). Differences in composition may include, for example, a difference in the type of monomer or polymer utilized in the formulation, a difference in loading of the therapeutic, a difference in crosslinking density of the final needle, a difference in coating of the final microneedle, or any other chemical differences in the liquid resin.

For example, microneedles with different layers may be fabricated. See, e.g., U.S. Pat. No. 8,734,697, US 2011/0028905 A1, US 2011/0152792, U.S. Pat. No. 8,491,534 and US 2008/0269685. All of these patents utilize a mold-filling method to generate microneedles with multiple layers. Briefly, a microneedle master (typically made of metal or silicon) is used to generate a polymeric mold, often cast in PDMS. This mold is then partially filled with a specified quantity of the first material with a series of time consuming vacuum and centrifugation steps. After drying, the remainder of the mold is filled with a second material of interest.

However, the disclosed microneedles may be accomplished with the methods of additive manufacturing. Utilizing an additive manufacturing process for the production of microneedles enables microneedles to be produced more quickly than mold-based techniques. Microneedles may also be produced in shapes that cannot be molded, such as, for example, undercut microneedles. Additive manufacturing also has the opportunity to increase consistency in microneedle composition (microneedle dimensions, drug-loading, tip sharpness, etc.) across an array by automating the production process.

Figure 9:
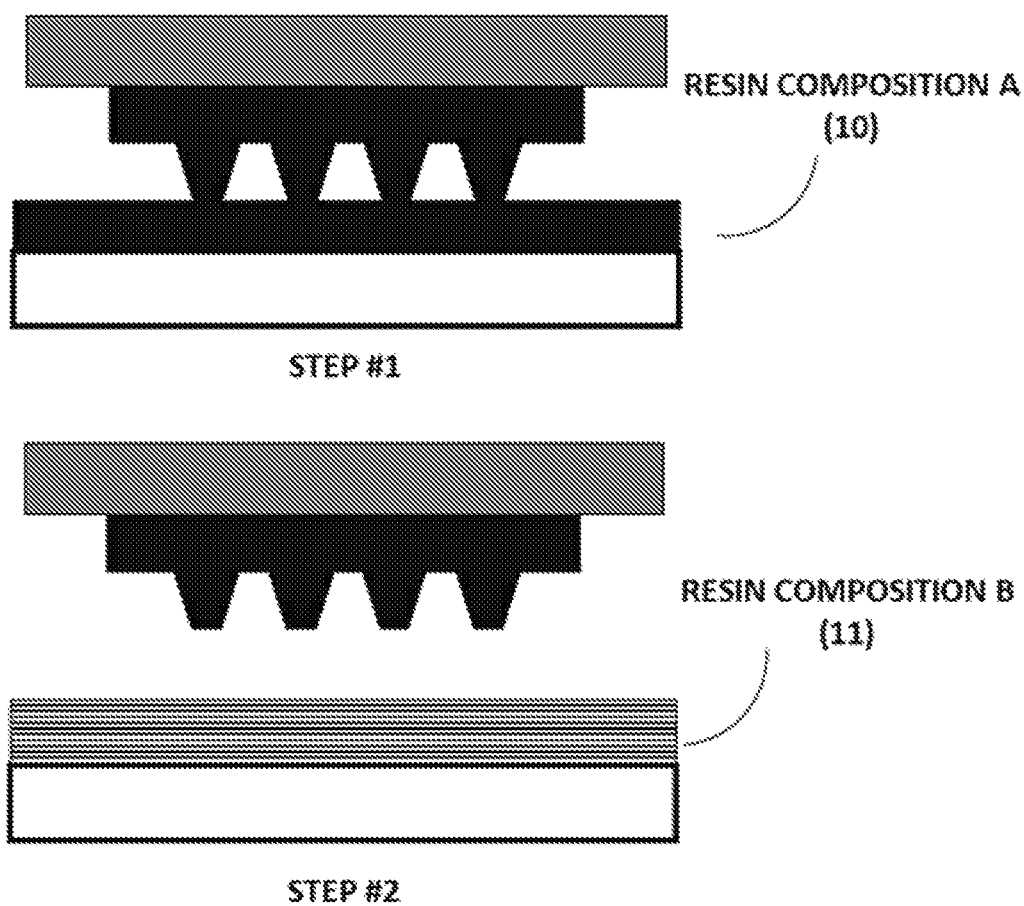
FIG. 9 shows a representative schematic of a mid-production resin exchange.
Figure 9:
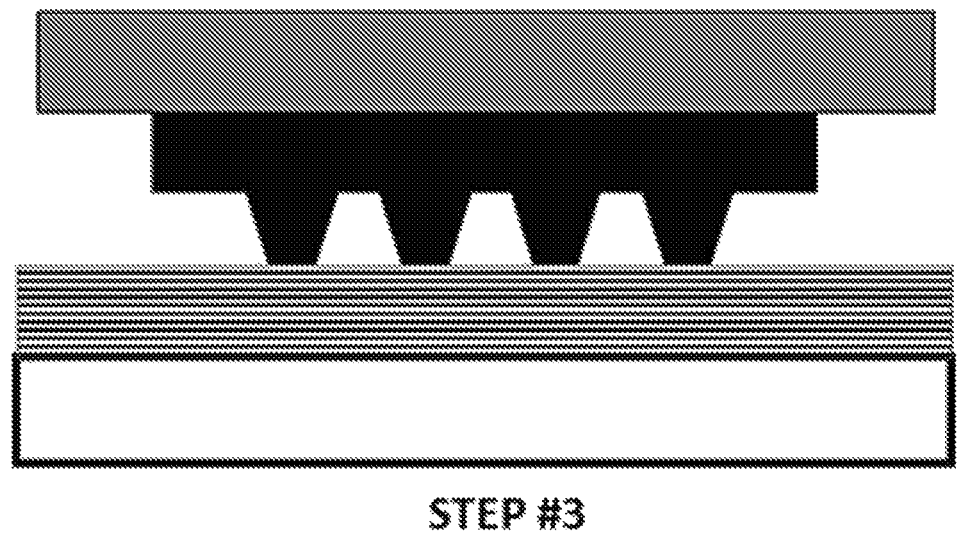
Figure 9:
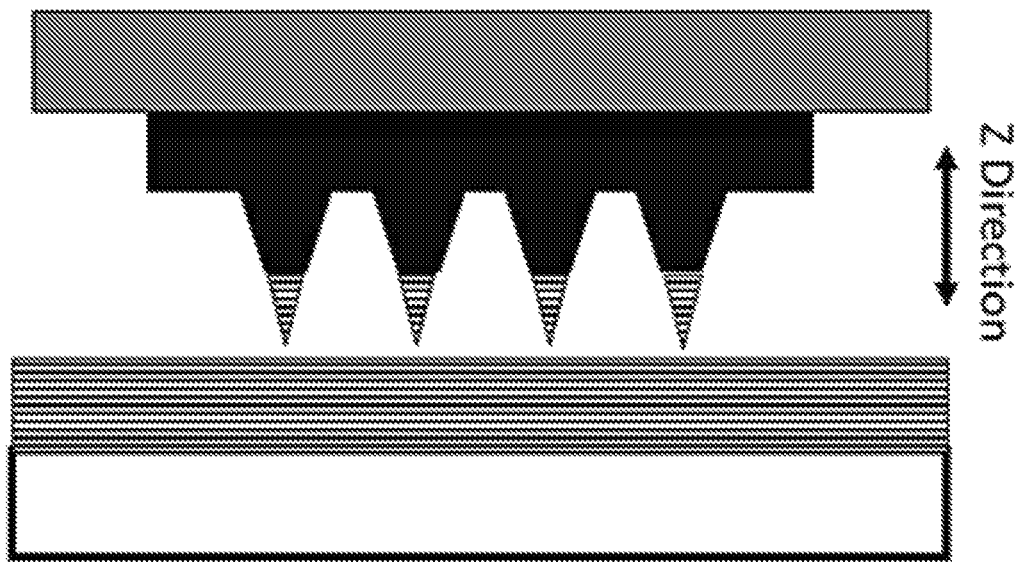

FIG. 9 shows a representative CLIP process that could be utilized to produce multi-component microneedles wherein components are spatially segmented along the z axis of the needle. Briefly, the CLIP method shown in FIG. 7A can be utilized to fabricate a portion of the microneedle patch from a resin of resin composition A 10, Build elevator 4 is then lifted above the build platform in step 2 and the liquid resin pool is removed and replaced with a new resin pool of resin composition B 11. The remainder of the microneedle is then fabricated with resin composition B.

The technique demonstrated in FIG. 7A could be utilized to produce multi-component microneedle patches of a number of different aspects, depicted in FIG. 10A-D. These aspects can be utilized for a variety of different purposes. For example, the aspect shown in FIG. 10A is a microneedle in which the needle tip is a different composition than the remainder of the needle. In some cases, the therapeutic would be loaded into the microneedle tip, but not be loaded into the base. Without wishing to be bound by theory, this may be useful for maximizing the amount of a therapeutic that is delivered to the skin if the needle does not completely insert into the skin. This high delivery efficiency is particularly useful for therapeutics that are expensive or have limited availability, where a dose-sparing effect is desirable. Localizing the therapeutic at the tip may also enable more consistent delivery in cases where different clinicians have different insertion techniques, which result in differences in penetration depth of the needle between applications.

Furthermore, this technique enables therapeutic to be delivered to a specific layer within the skin (e.g., stratum cornerum, epidermis, dermis). Without wishing to be bound by theory, layer-specific delivery may enable localization of the therapeutic to a specific cell type or allow for more control over the rate of diffusion of this therapeutic from the site of insertion into the skin to the bloodstream.

In other aspects, both the base and tip may be loaded with therapeutic. Compositions with different release/degradation kinetics may enable further control over pharmacokinetic profiles. For example, one composition could enable rapid burst release of the therapeutic, while the other composition could provide sustained release of the therapeutic out of the needle.

In other aspects, the tip and base compositions could be chosen for differing mechanical properties, wherein a strong material could be used for the tip and a weaker material (which is desirable for another property, such as its drug solubility or release characteristics) could be utilized for the base. In this way, the desired chemical and mechanical properties of the needle could be obtained by combining the properties of each individual matrix.

Other aspects include, but are not limited to, patches in which the patch backing is a different material than the needles (FIG. 10B), tip-loaded patches that contain a backing of a distinct composition (FIG. 10C) and needles in which multiple layers are present (FIG. 10D). These aspects may be utilized for any of the purposes listed above. An additional use of patches which contain a distinct backing composition is the ability to dissolve away a water soluble backing layer to deposit needles within the skin.

In a further aspect, the method further comprises continuing and/or repeating steps (c)-(e) to create a subsequent polymerized region adhered to a previous polymerized region. This may be continued, for example, until the continued or repeated deposition of polymerized regions adhered to one another forms said microneedle device.

In a further aspect, steps (c)-(e) are performed simultaneously. In a still further aspect, steps (c)-(e) are performed sequentially.

In a further aspect, the polymerizable liquid comprises a free radical polymerizable liquid and the polymerization inhibitor comprises oxygen. In a still further aspect, the polymerizable liquid comprises an acid-catalyzed or canonically polymerizable liquid and the polymerization inhibitor comprises a base.

In a further aspect, irradiating is via actinic radiation.

In a further aspect, advancing is carried out at a cumulative rate of at least 0.1, 1, 10, 100, or 1000 microns per second. In a still further aspect, advancing is carried out at a cumulative rate of at least 0.1, 1, 10, or 100 microns per second. In yet a further aspect, advancing is carried out at a cumulative rate of at least 0.1, 1, or 10 microns per second. In an even further aspect, advancing is carried out at a cumulative rate of at least 0.1 or 1 microns per second. In a still further aspect, advancing is carried out at a cumulative rate of at least 1, 10, 100, or 1000 microns per second. In yet a further aspect, advancing is carried out at a cumulative rate of at least 10, 100, or 1000 microns per second. In an even further aspect, advancing is carried out at a cumulative rate of at least 100 or 1000 microns per second.

In a further aspect, advancing comprises moving the build elevator vertically from the build surface.

In a further aspect, the microneedle device is formed in less than 30 minutes, less than 20 minutes, or less than 10 minutes. In a still further aspect, the microneedle device is formed in less than 30 minutes. In yet a further aspect, the microneedle device is formed in less than 25 minutes. In an even further aspect, the microneedle device is formed in less than 20 minutes. In a still further aspect, the microneedle device is formed in less than 15 minutes. In yet a further aspect, the microneedle device is formed in less than 10 minutes. In an even further aspect, the microneedle device is formed in less than 5 minutes.

D. METHODS OF DELIVERING THERAPEUTIC AGENTS

In one aspect, disclosed are methods of delivering a therapeutic agent to a subject, the method comprising administering to the subject a microneedle device comprising: (a) a backing; and (b) a plurality of biocompatible microneedles projecting from the backing, wherein the microneedles comprise a therapeutic agent and one or more of: (i) a curved, discontinuous, undercut, or perforated sidewall; (ii) a sidewall comprising a breakable support; and (iii) a cross-section that is non-circular and non-polygonal, and/or wherein the microneedles are tiered, thereby delivering the therapeutic agent. Thus, in various aspects, the disclosed microneedle devices could be utilized for delivery of therapeutic agents useful for a number of different therapeutic indications. Cargos may include, for example, nano- or micro-particles, proteins, small molecules, enzymes, sugars, and nucleic acids, etc. See also Kim et al., "Microneedles for drug and vaccine delivery," Adv. Drug Deliv. Rev. 64(14):1547-1568, 2012; Indermun et al., "Current advances in the fabrication of microneedles for transdermal delivery," 3 Controlled Release 185:130-138, 2014.

Exemplary agents and indications include, but are not limited to, delivery of insulin for diabetes, delivery of chemotherapeutics or vaccines for cancer, e.g., skin cancer (melanoma, basal cell carcinoma, inflammatory breast cancer, etc.), delivery of anesthetics, delivery of cosmeceutical agents such as botox, delivery of anticoagulants such as heparin, delivery of various enzymes (such as butyrylcholinesterase) and growth hormones, delivery of immunomodulatory agents for treating autoimmune diseases such as psoriasis, bullous pemphigoid, epidermolysis bullosa, dermatomyositis, scleroderma, eczema, rheumatoid arthritis, and multiple sclerosis, etc. Microneedles also may be used for vaccines (e.g., particulate, protein subunit, nucleic acid, or whole pathogen) for a number of different infectious or non-infectious diseases. Microneedles also may be utilized to diagnose a variety of conditions such as, for example, diabetes, heart attacks, infectious diseases, and bacterial infections, or to perform a standard blood test.

In a further aspect, the microneedle devices described herein can be used for cutaneous immunization.

In a further aspect, the microneedle devices can be used for chemotherapy and immunochemotherapy applications, for example, as an alternative to or in addition to traditional topical chemotherapy approaches. In the case of cutaneous tumors, including skin derived tumors (e.g., basal cell, squamous cell, Merkel cell, and melanomas) and tumors metastatic to skin (e.g., breast cancer and melanoma), topical delivery may be desired. Current methods of topical delivery generally require the application of creams or repeated local injections. The effectiveness of these approaches is currently limited by limited penetration of active agents into the skin, non-specificity, and unwanted side effects.

Further, multiple bioactive agents can be delivered in a single microneedle array (e.g., a patch). This enables an immunochemotherapeutic approach based on the co-delivery of a cytotoxic agent with and immune stimulant (adjuvants). In an immunogenic environment created by the adjuvant, tumor antigens releases from dying tumor cells will be presented to the immune system, inducing a local and systemic anti-tumor immune response capable of rejecting tumor cells at the site of the treatment and throughout the body. See also U.S. Pat. No. 8,834,423 to Palo et al.

In a further aspect, the therapeutic agent comprises a protein therapeutic, a small molecule therapeutic, a vaccine antigen, or an antigenic fragment thereof.

E. METHODS OF TREATING A DISEASE IN A SUBJECT

In one aspect, disclosed are methods of treating a disease in a subject, the method comprising administering to the subject a microneedle device comprising: (a) a backing; and (b) a plurality of biocompatible microneedles projecting from the backing, wherein the microneedles comprise a therapeutic agent and one or more of: (i) a curved, discontinuous, undercut, or perforated sidewall; (ii) a sidewall comprising a breakable support; and (iii) a cross-section that is non-circular and non-polygonal, and/or wherein the microneedles are tiered, thereby treating the disease.

In one aspect, disclosed are methods of treating a disease or condition in a subject in need thereof, comprising administering to the subject a disclosed microneedle device.

Thus, in various aspects, the disclosed microneedle devices may be useful for the delivery of therapeutic agents useful for treatment a number of different therapeutic indications.

"Treat" or "treatment" as used herein refers to any type of treatment that imparts a benefit to a subject afflicted with a disease or disorder that may benefit from microneedle delivery of a therapeutic agent, including improvement in the condition of the patient (e.g., in one or more symptoms), delay in the progression of the disease or disorder, delay in onset or recurrence of the disease or disorder, etc.

For example, microneedle devices as taught herein may be used to deliver insulin in the treatment of diabetes. See Fukushima et al., "Pharmacokinetic and Pharmacodynamic Evaluation of Insulin Dissolving Microneedles in Dogs," Diabetes Technology & Therapeutics 12(6):465-474, 2010; Ito et al., "Transdermal Insulin Application System with Dissolving Microneedles," Diabetes Technology & Therapeutics 14(10):891-899, 2012; Ito et al., "Two-layered dissolving microneedles formulated with intermediate-acting insulin," International J Pharmaceutics 436:387-393, 2012; Ling et al., "Dissolving polymer microneedle patches for rapid and efficient transdermal delivery of insulin to diabetic rats," Acta Biomaterialia 9:8952-8961, 2013.

The present invention is primarily concerned with the treatment of human subjects, but the invention may also be carried out on animal subjects, particularly mammalian subjects such as mice, rats, dogs, cats, livestock and horses for veterinary purposes, and for drug screening and drug development purposes. Subjects may be of any age, including infant, juvenile, adolescent, adult, and geriatric subjects.

The ability to easily modulate patch size and shape can be used to make personalized microneedle patches. For example, a microneedle patch could be made to specifically cover the area of an individual's wound or to alter the size of a microneedle patch to match the dosage of a medication to a patient's body weight, etc. Additive manufacturing methods also provide the opportunity to produce microneedle patches at the point of care.

In a further aspect, the therapeutic agent comprises a protein therapeutic or a small molecule therapeutic.

In a further aspect, the disease is diabetes and the therapeutic agent is insulin. In a still further aspect, the disease is a bacterial infection and the therapeutic agent is an antibiotic. In yet a further aspect, the disease is cancer and the therapeutic agent is a chemotherapeutic agent.

F. METHODS OF DETECTING A BIOMARKER IN A SAMPLE

In one aspect, disclosed are methods of detecting a biomarker in a sample, the method comprising: (a) providing a microneedle device comprising: (i) a backing; and (ii) a plurality of biocompatible microneedles projecting from the backing, wherein the microneedles comprise a probe for the biomarker and one or more of (1) a curved, discontinuous, undercut, and/or perforated sidewall; (2) a sidewall comprising a breakable support; and (3) a cross-section that is non-circular and non-polygonal, and/or wherein the microneedles are tiered; (b) contacting the device with the sample; and (c) identifying the biomarker, thereby detecting the biomarker in the sample.

In a further aspect, contacting is during an intraoperative procedure. In a still further aspect, contacting is after the sample has been removed from the subject.

In a further aspect, the sample is a tissue or biological sample. In a still further aspect, the sample is a tissue sample. In yet a further aspect, the sample is a biological sample. The tissue or biological sample can be from an organ such as, for example, a brain, a heart, a breast, a liver, a pancreas, a spleen, a bladder, a stomach, a lung, a uterus, a cervix, a prostate, a kidney, an intestine, an appendix, and a colon.

In a further aspect, the sample is in a mammal. In a still further aspect, the mammal is human.

The probe may be covalently attached to a microneedle. Alternatively, the probe may be non-covalently attached to a microneedle. Examples of probes include, but are not limited to, polynucleotides, polypeptides, proteins, antibodies, small molecules, and biological receptors.

The present invention is explained in greater detail in the following non-limiting examples.

G. EXAMPLES

The following examples are put forth so as to provide those of ordinary skill in the art with a complete disclosure and description of how the devices and/or methods claimed herein are made and evaluated, and are intended to be purely exemplary of the invention and are not intended to limit the scope of what the inventors regard as their invention. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

1. Materials

Figure 11B:
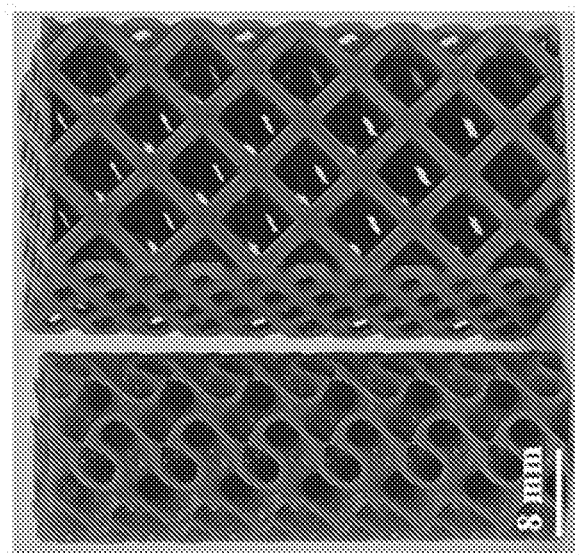
FIG. 11A-C show representative images illustrating that CLIP enables fast print speeds and layerless part construction.
Figure 11A:
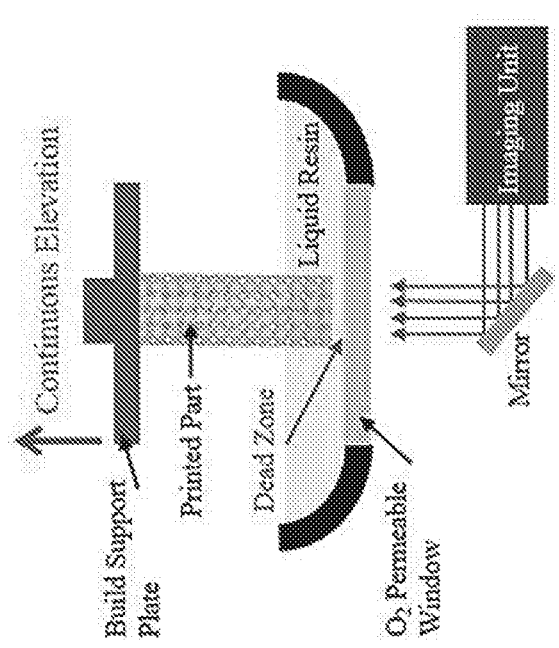
Figure 11C:
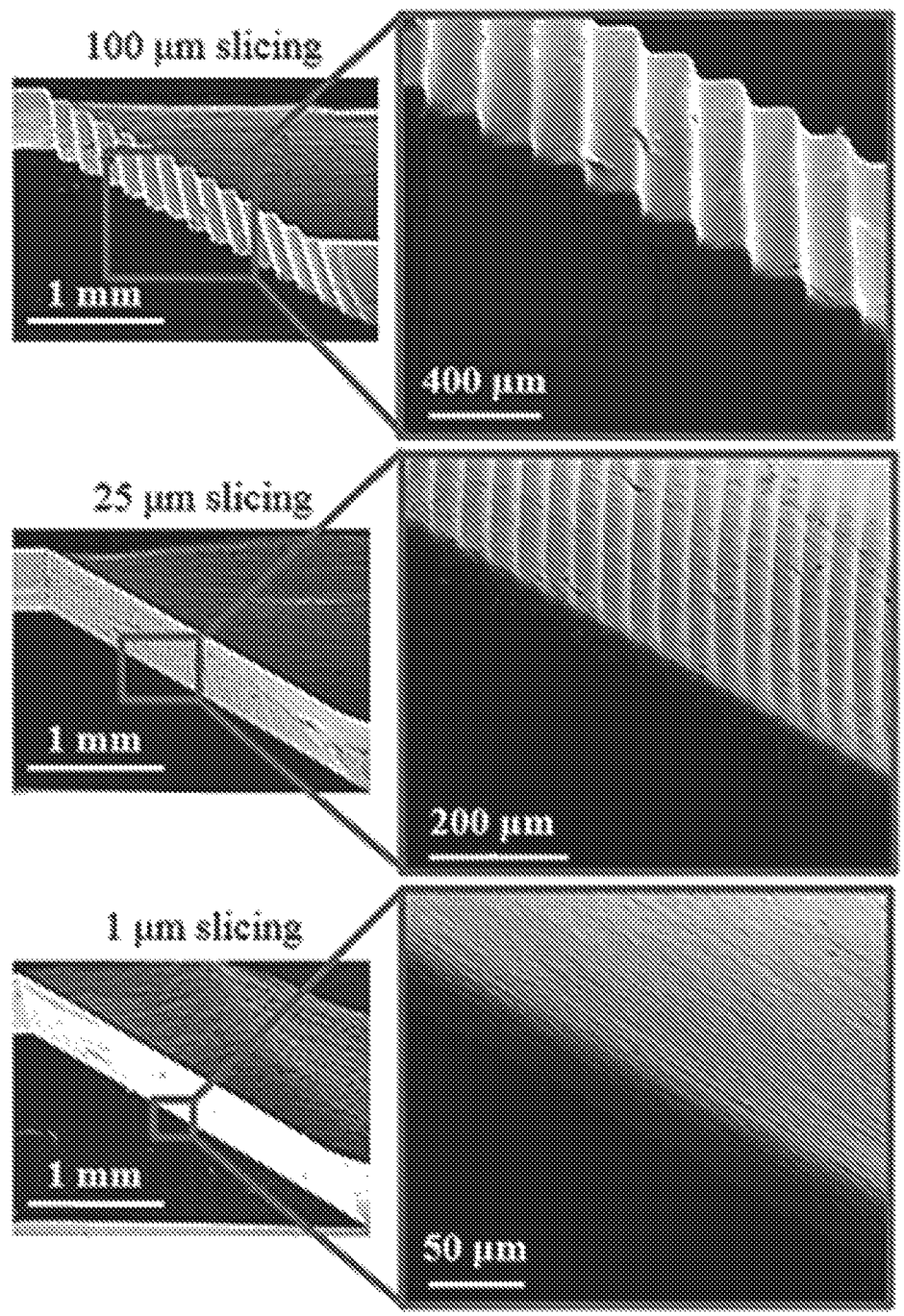

The ramp test patterns in FIG. 11C were printed with trimethylolpropane triacrylate (TMPTA) using the photoinitiator, diphenyl (2,4,6-trimethyl-benzoyl)phosphine oxide. Other objects were printed with a combination of monomers from Sartomer (CN2920 & CN981), TMPTA, and reactive diluents such as n-vinylpyrrolidone, isobornyl acrylate, and cyclohexane dimethanol di-vinyl ether. Photoinitiators, phenylbis(2,4,6-trimethyl-benzoyl)phosphine oxide, 1-hydroxycyclohexyl phenyl ketone, and 2-benzyl-2-(dimethylamino)-4'-morpholinobutyrophenone, and an assortment of dyes from Wikoff and Mayzo were also utilized.

2. Continuous Liquid Interface Printing

FIG. 11A illustrates the simple architecture and operation of a 3D printer that takes advantage of an oxygen inhibited dead zone. As shown in FIG. 11A, the part (gyroid) is printed continuously by simultaneously elevating the build support plate while changing the 2-D cross-sectional UV images from the imaging unit. The oxygen permeable window creates a dead zone (persistent liquid interface) between the elevating part and window.

Figure 12:
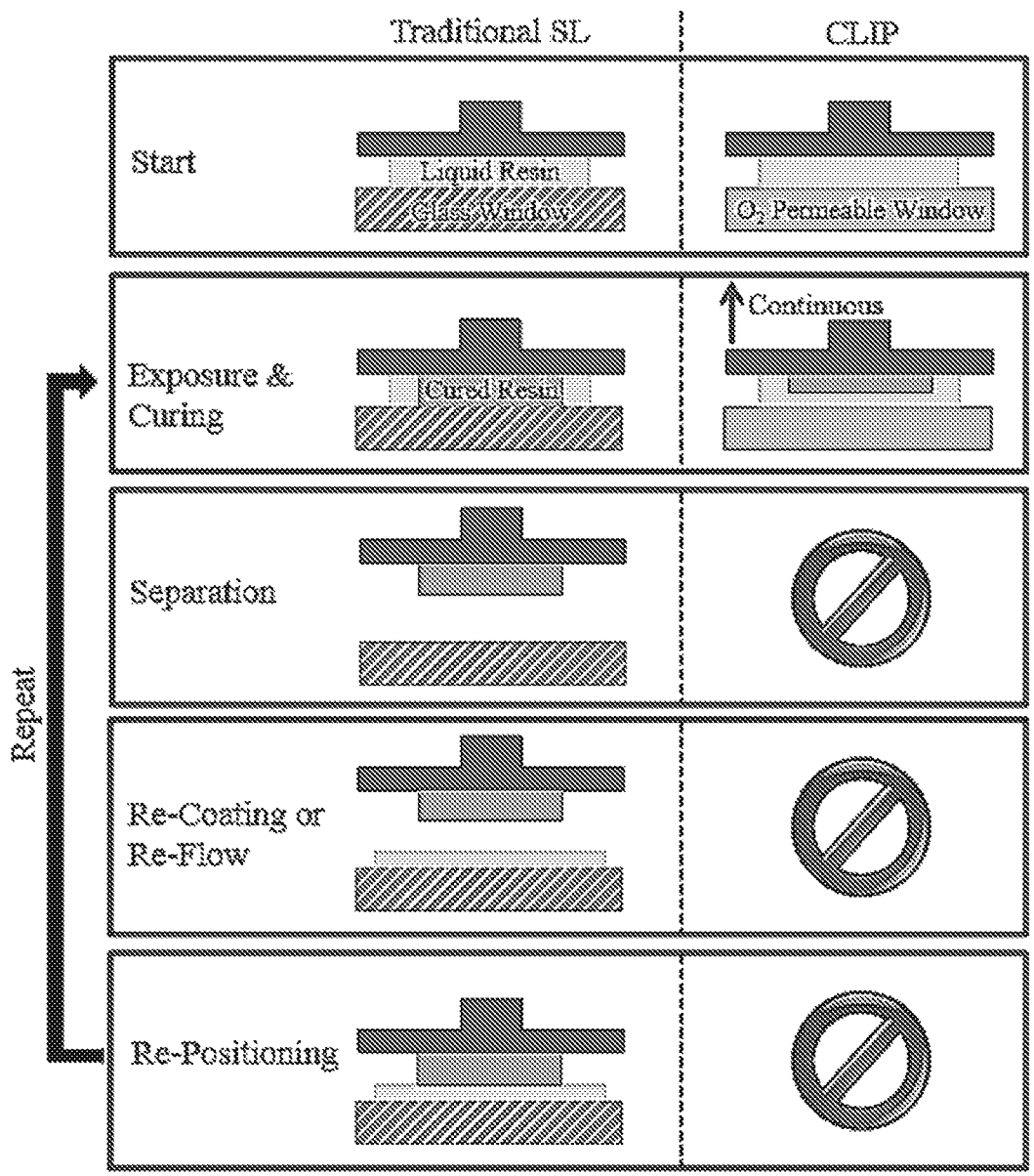
FIG. 12 shows a representative diagram indicating that CUP removes sequential steps from traditional stereolithography (SL).
Figure 14:
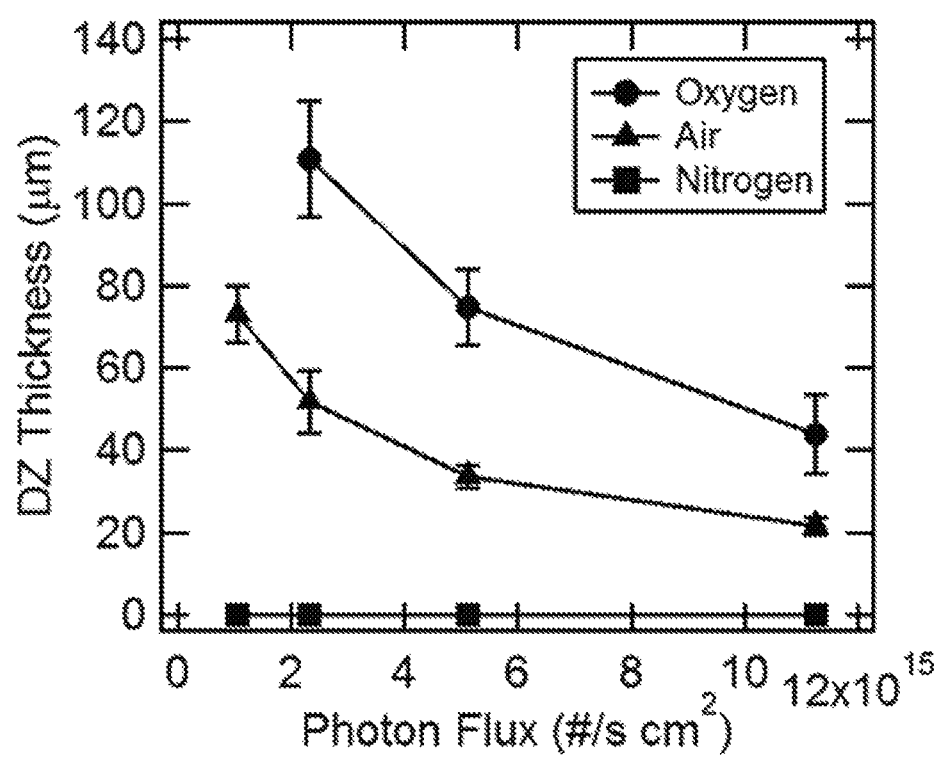
FIG. 14 shows a representative graph illustrating that the dead zone is created by oxygen permeation through the window.
Figure 15B:
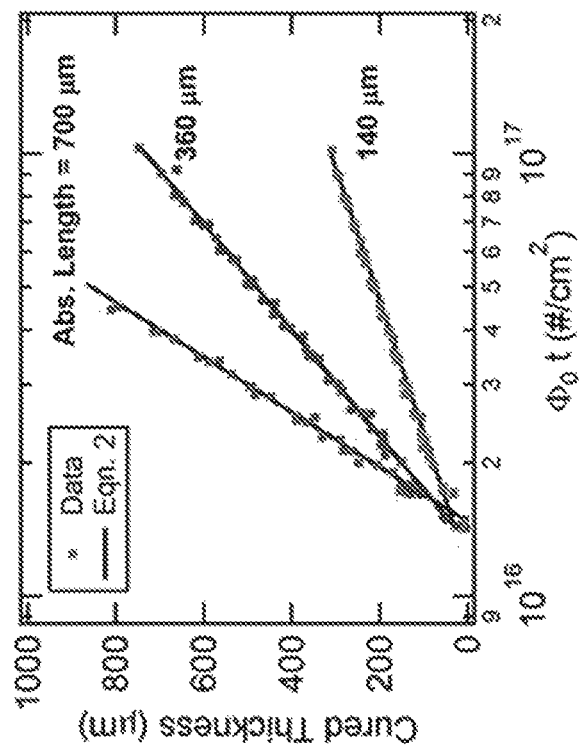
FIG. 15A-D show representative images illustrating that a trade-off exists between print speed and print resolution.
Figure 15A:
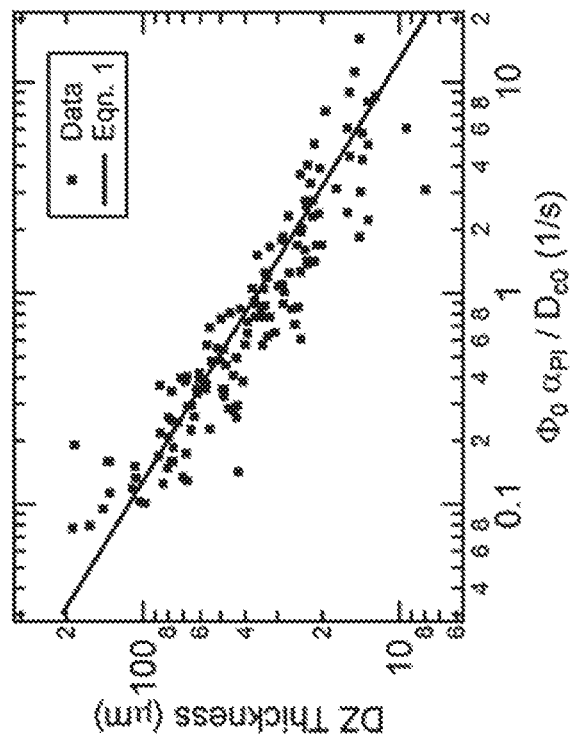
Figure 15D:
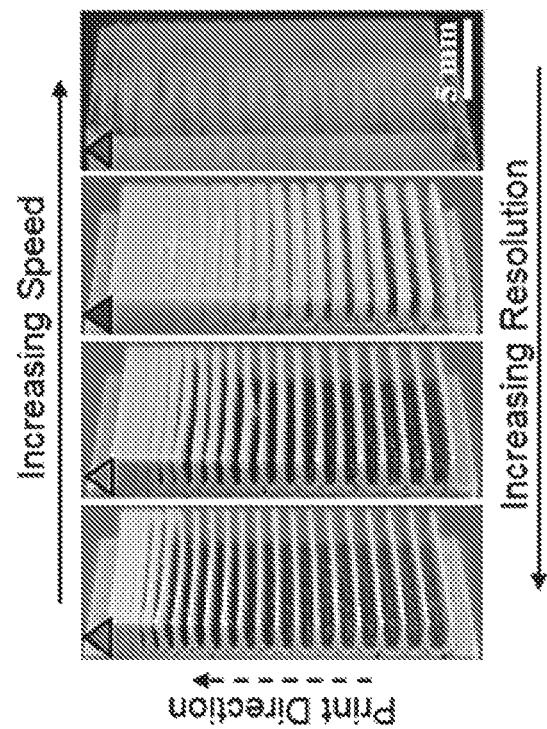
Figure 15C:
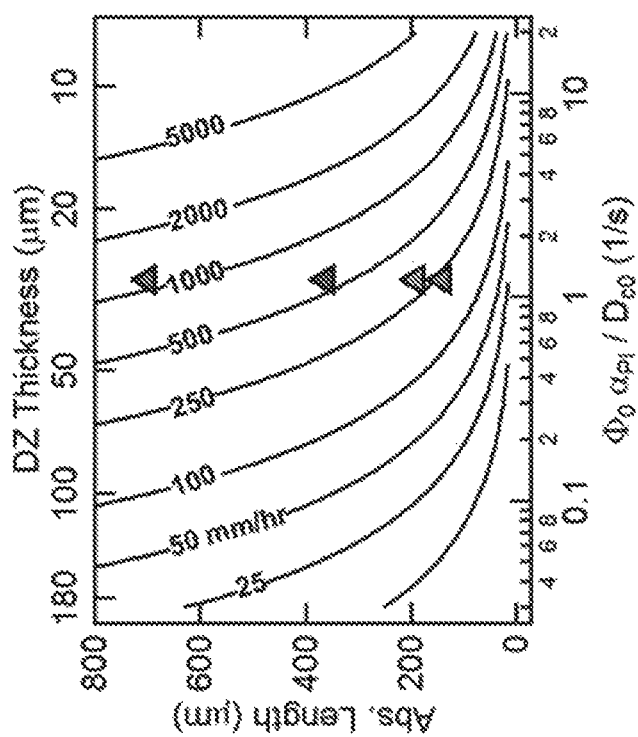
Figure 16:
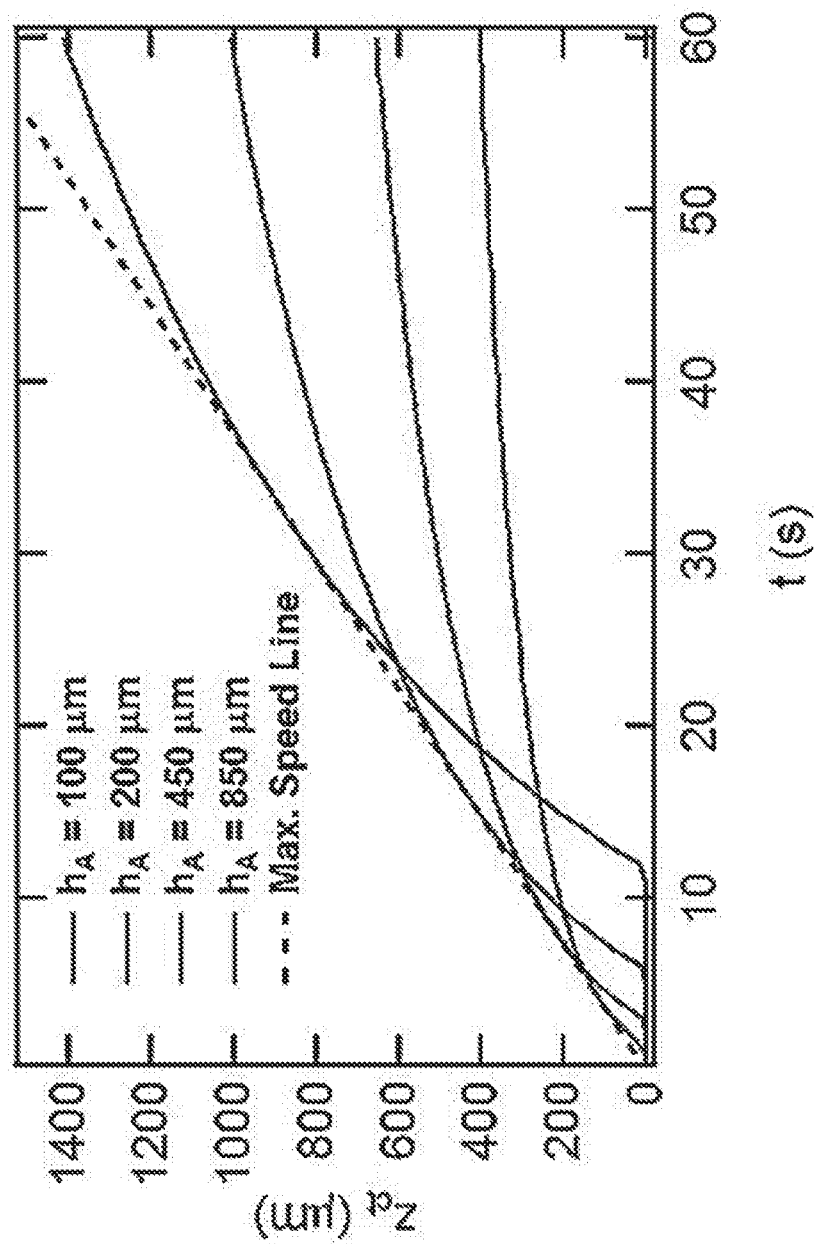
FIG. 16 shows a representative diagram illustrating that maximum print speed is identical for resins with different photoinitiator concentration.
Figure 17:
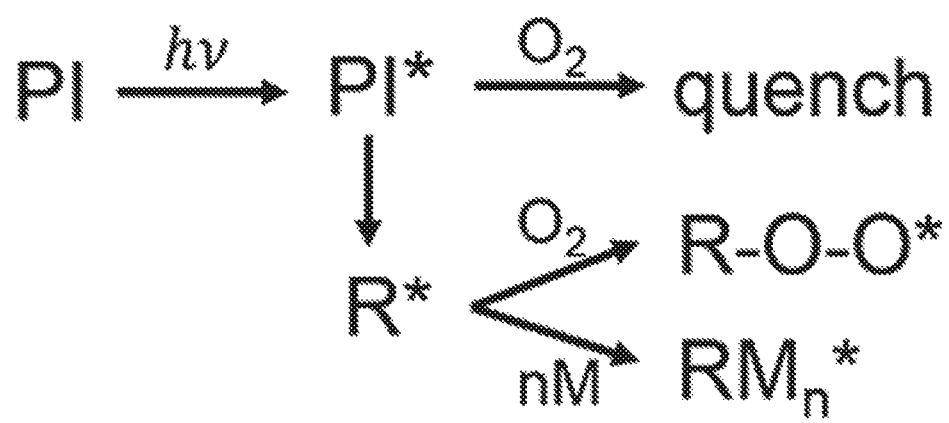
FIG. 17 shows a representative schematic illustrating that free radicals either inhibit oxygen or initiate polymerization.
Figure 18A:
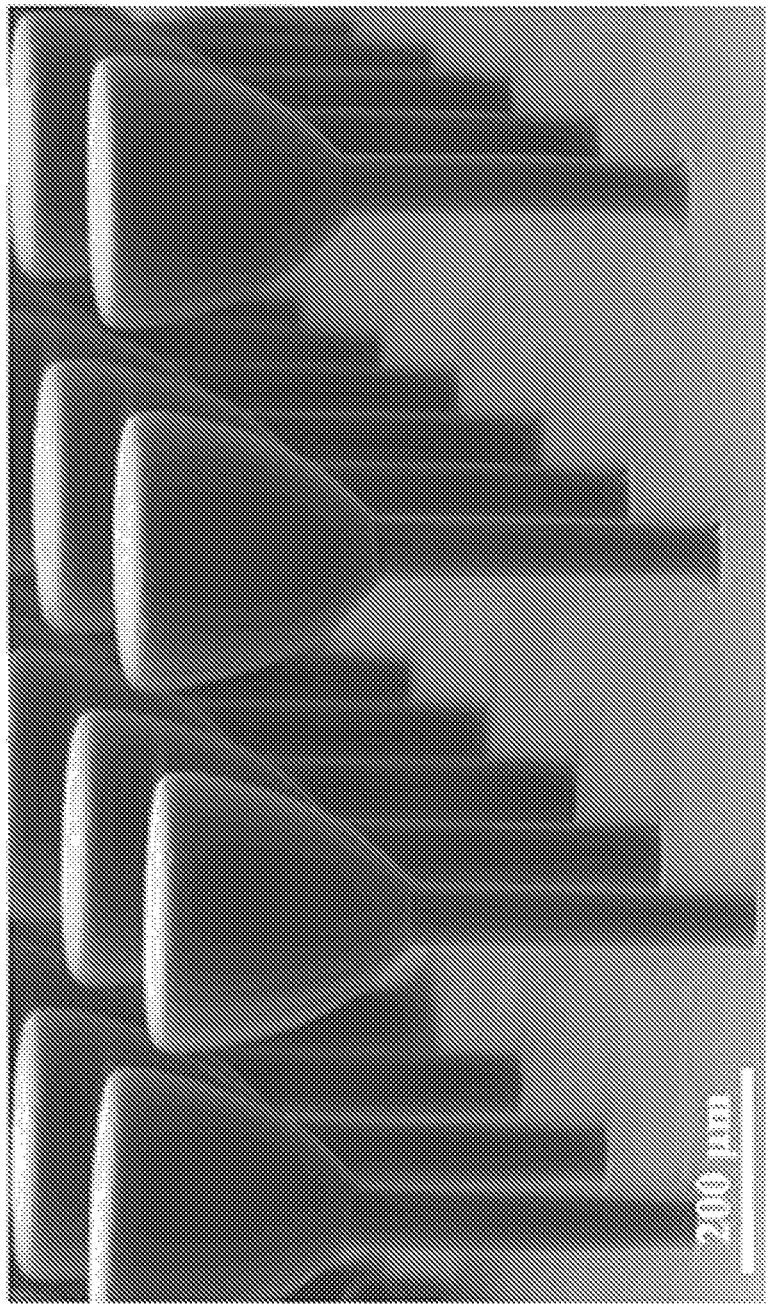
FIG. 18A-C show representative images illustrating that parts fabricated using CLIP can range in size from micropaddles with 50 μM diameter stems (18A, printed at 25 mm/hr), a 10 cm tall Eiffel Tower model (18B, printed at 100 mm/hr; features <1 mm in size are obtained as shown in the inset), and a shoe cleat over 20 cm long (18C, printed at 100 mm/hr).
Figure 18C:
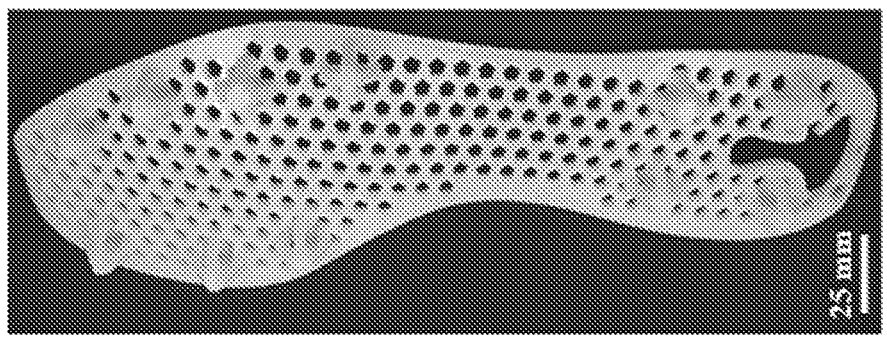
Figure 18B:
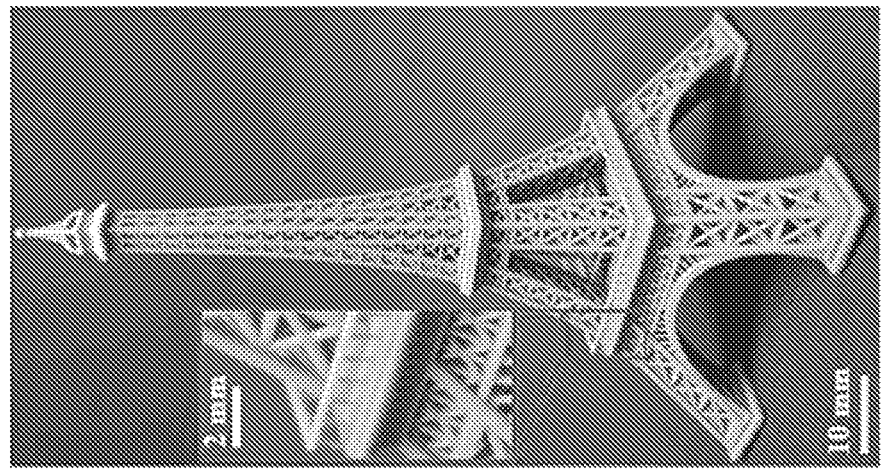
Figures 19A, 19B:
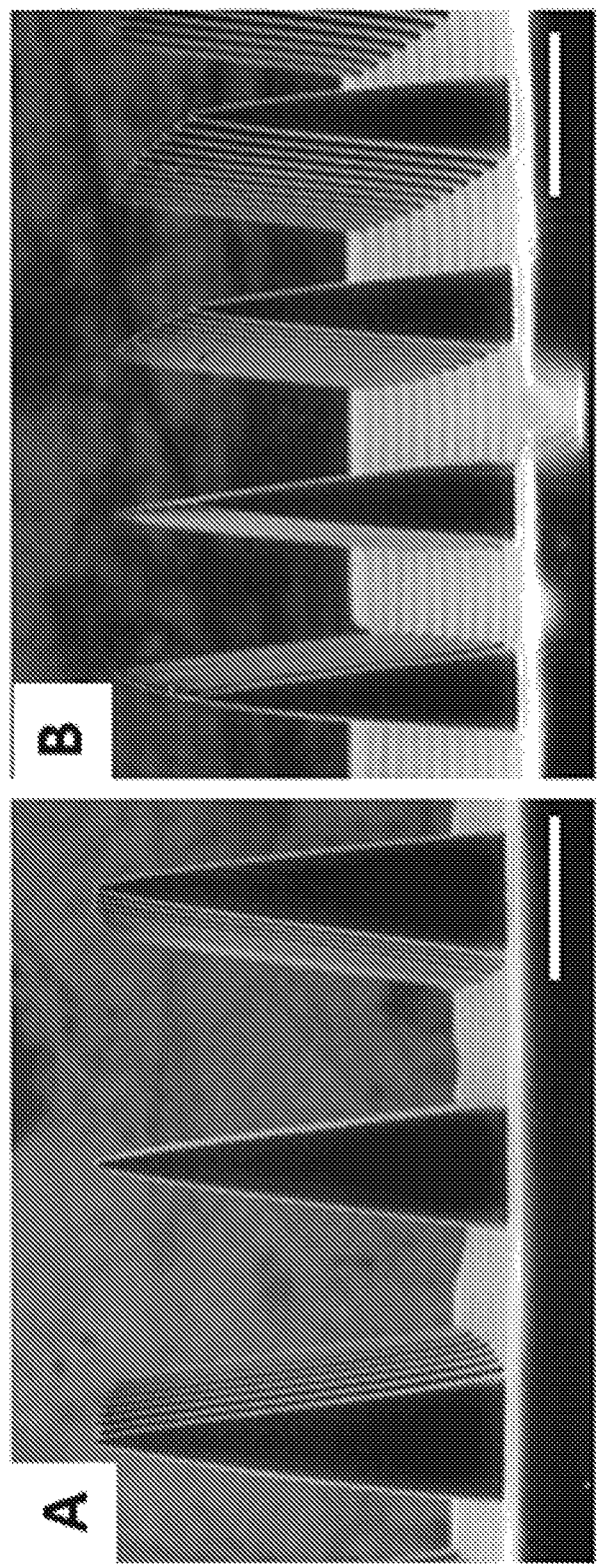
FIG. 19A-D show representative images of CLIP microneedles with a variety of dimensions. Specifically.
Figure 19D:
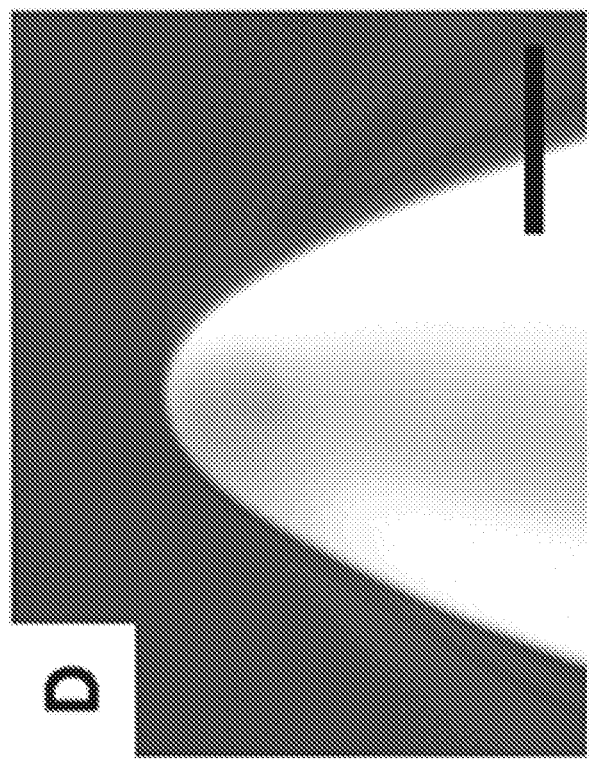
Figure 19C:
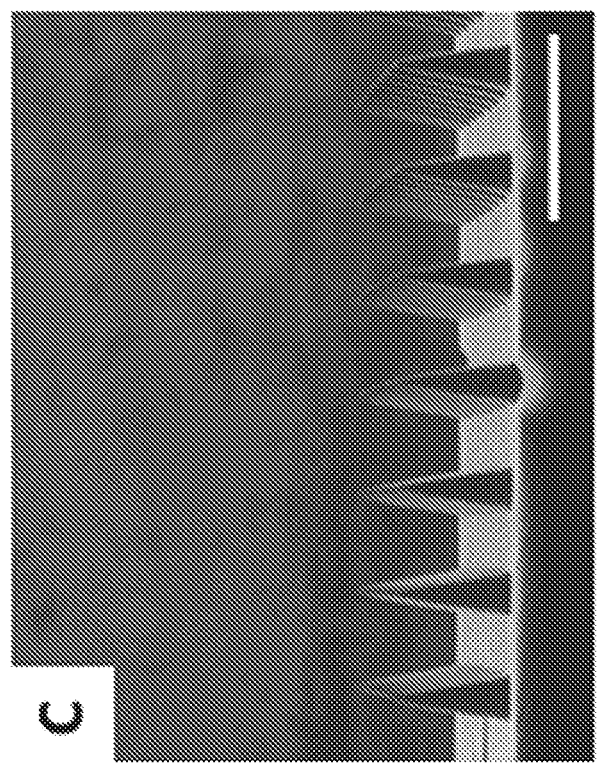
Figures 20A, 20B:
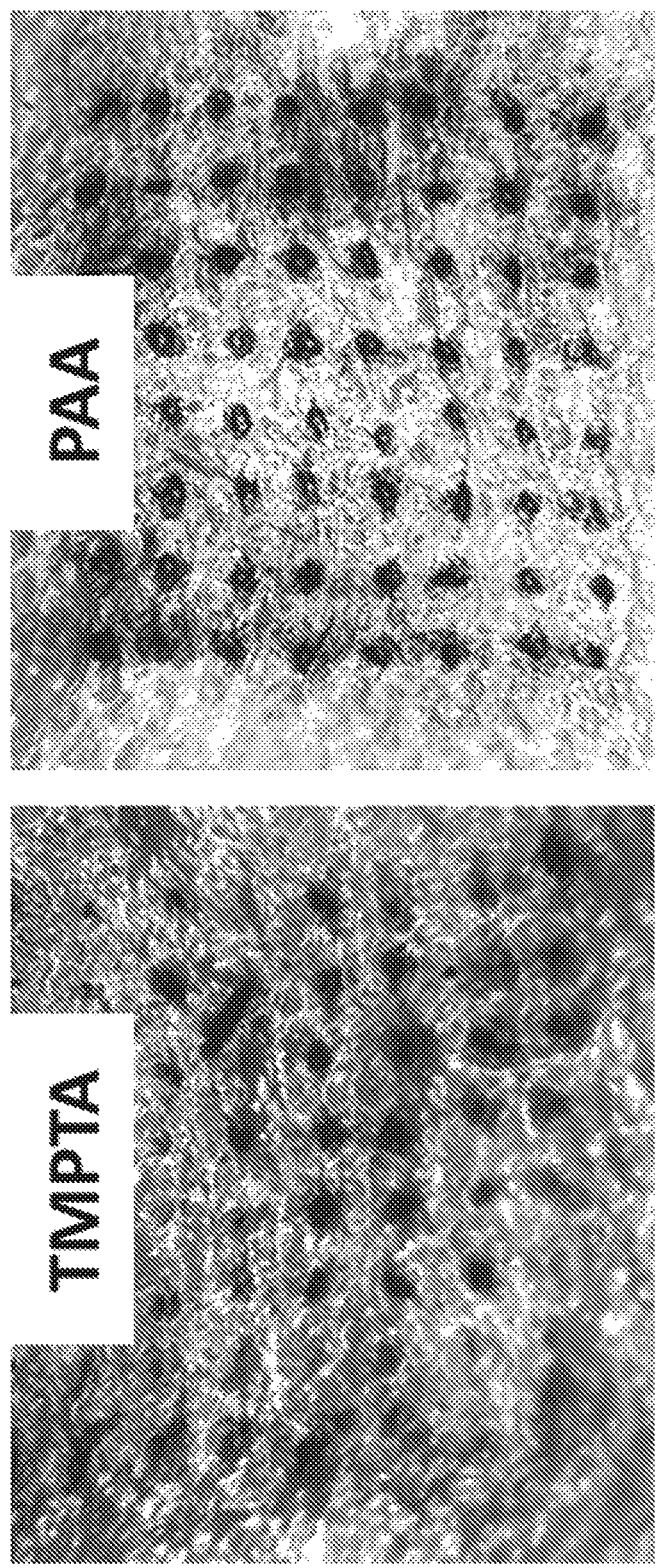
FIG. 20A-D show representative images of skin penetration of CLIP microneedle arrays. Specifically.
Figures 20C, 20D:
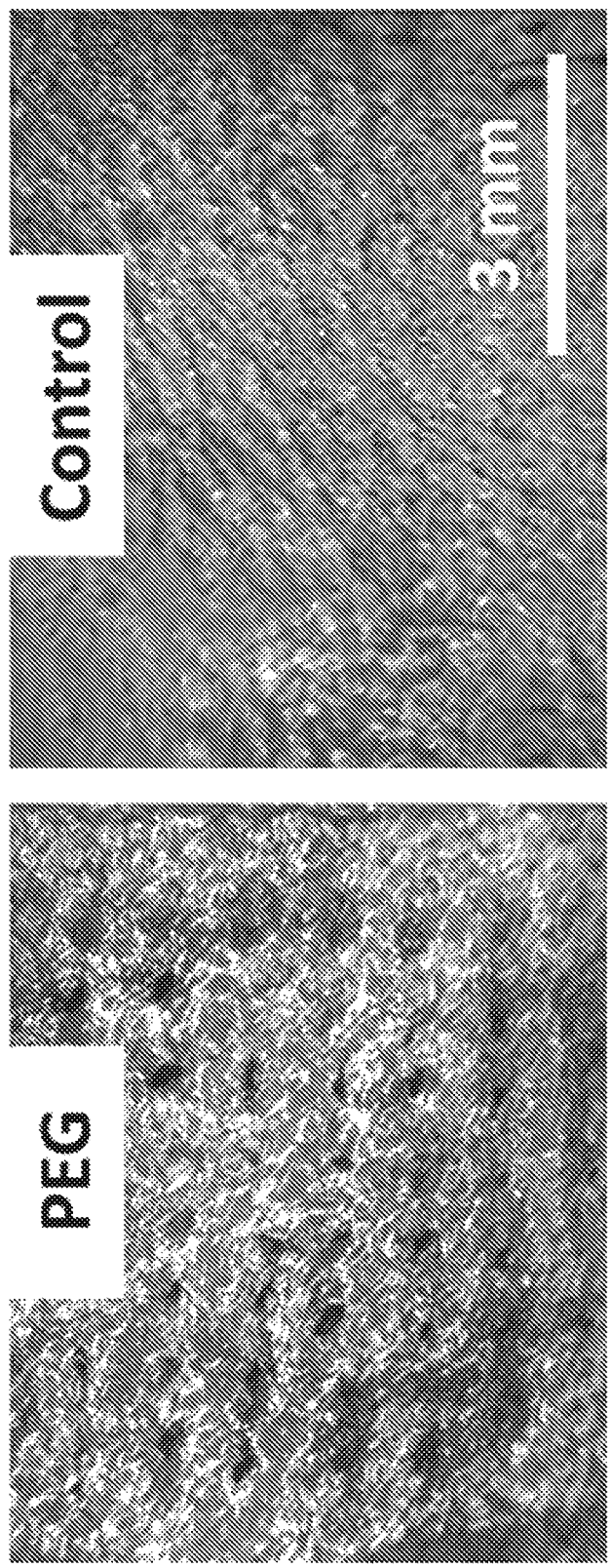

CLIP proceeds via projecting a continuous sequence of UV images (generated by a digital light processing imaging unit) through an oxygen-permeable, UV-transparent window below a liquid resin bath. The dead zone created above the window maintains a liquid interface below the advancing part. Above the dead zone, the curing part is continuously drawn out of the resin bath creating suction forces that continually renew reactive liquid resin. This continual process is fundamentally different from traditional bottom-up stereolithography printers where UV exposure, resin renewal, and part movement must be conducted in separate and discrete steps (FIG. 12). Even for inverted top-down approaches where photo-polymerization occurs at an air-resin interface (the part is successively lowered into a resin bath during printing (Gibson et al., *Additive Manufacturing Technologies: Rapid Prototyping to Direct Digital* Manufacturing. (Springer, New York, 2010); Jacobs, P. F., *Rapid Prototyping & Manufacturing: Fundamentals of Stereo-Lithography*. Society of Manufacturing Engineers, Dearborn, Mich., 1992)), these steps must be conducted sequentially for the formation of each layer. Since each step takes several seconds to implement for each layer, and since each layer of a part has a typical thickness of 50-100 µm, vertical print speeds are restricted to a few mm/hr (Gibson et al., *Additive Manufacturing Technologies: Rapid Prototyping to Direct Digital* Manufacturing. (Springer, New York, 2010)). By contrast, the print speed for CLIP is limited by resin cure rates and viscosity not by step-wise layer formation. For example, the 5 cm tall gyroid and argyle structures shown in FIG. 11B were printed at vertical draw speeds 500 min/hr, i.e., in less than 10 minutes. An additional benefit of continuous printing is that choice of slicing thickness, which affects part resolution, does not influence print speed as shown in the ramp test patterns in FIG. 11C. Specifically, FIG. 11C shows representative RAMP test patterns printed at the same print speed regardless of slicing thickness (100 μM, 25 μM, and 1 μM). Since CLIP is continuous, the refresh rate of projected images may be increased without altering print speed, ultimately allowing for parts to approach layerless 3D objects.

Referring to FIG. 12, traditional stereolithography first exposes resin to UV light, which causes cured adhesion to a build window such as glass. Next, the part must be mechanically separated, followed by resin re-coating and part re-positioning, before the next layer can be exposed. CLIP, with a permanent liquid interface at the window, allows the part to be continuously exposed while elevating, thereby eliminating three steps in the process.

3. Fabrication of Microneedles

To demonstrate the utility of CLIP in addressing challenges associated with microneedle fabrication times, microneedles were fabricated using trimethylolpropane triacrylate (TMPTA) plus 2.5 wt % DPO. Briefly, a computer aided design (CAD) file was generated and sliced using the open source software Slic3r in 1 μm slices. This file was printed using the CLIP7 (Table 2) with 5.4 mW/cm² of light at 100 mm/hr. Environmental Scanning Electron Micrographs of microneedles of three different heights along with their dimensions and print times are illustrated in FIG. 19A-D and Table 3.

TABLE 2

|  | CLIP | CLIP Mini |
|---|---|---|
| Light Source (nM LED) | 7 | 365 |
| Max. Light Intensity (W/cm²) | 77 | 30 |
| Theoretical Resolution (μM) | 10 | 20 |
| Build Area (mm) | ~7.7 × 10.3 × 100 | 15 × 24 × 100 |
| Unit Size (inches) | ~36 H × 12 W × 24 D | 18¼ H × 9¹⁵⁄₁₆ W × 12½ D |

TABLE 3

| Nominal Height (μM) | Actual Height (μM) | Nominal Width (μM) | Actual Width (μM) | Print Time (s) | Tip Radius (μM) |
|---|---|---|---|---|---|
| 1000 | 1023.5 ± 52.8 | 333.3 | 321.4 ± 20.0 | 84.6 | 2.3 ± 0.5 |
| 700 | 712.6 ± 13.7 | 233.3 | 236.3 ± 8.7 | 79.5 | 3.1 ± 0.4 |
| 400 | 383.7 ± 8.6 | 133.3 | 135.4 ± 8.3 | 80.6 |  |

The example microneedles fabricated with CLIP are particularly sharp based on measurement of tip radius. Because insertion force is directly related to force of insertion, it is hypothesized that less force would be required to insert these needles into the skin than other polymeric microneedles.

4. Microneedle Composition and Testing

Microneedles have been fabricated with CLIP from a number of compositions, such as polyethylene glycol, polyacrylic acid, and polycaprolactone, as shown in FIG. 8A-C. The resin compositions for these needles are acrylic acid (Acros Organics, 99.5% purity), a polycaprolactone trimethacrylate (Mn=900, synthesized by known methods) and a poly (ethylene glycol) dimethacrylate (Mn=550. Sigma), all mixed with 2.5 wt % Diphenyl(2,4,6-trimethylbenzoyl) phosphine oxide as a photoinitiator. Microneedles were fabricated on the CLIP7 (see Table 1) at 25 mm/hr with 8.3, 1.5, and 1.2 mW/cm² of light (λ=370), for acrylic acid, polyethylene glycol, and polycaprolactone, respectively. The fabrication of each patch took approximately 5 minutes.

Monomers selected for CLIP microneedle fabrication were chosen for the differing solubility and release characteristics of their respective polymers. Poly(ethylene glycol) is a water-miscible polymer previously used for microneedle fabrication and encapsulation of hydrophilic cargos. Drug release from the PEG hydrogel is likely to occur via diffusion out of the swellable matrix, followed by slow degradation of the residual needle. Poly(caprolactone) is a lipophilic material useful for incorporating hydrophobic molecules (such as chemotherapeutics), which typically exhibit poor oral bioavailability. It is susceptible to hydrolytic degradation of ester linkages, enabling sustained release of lipophilic cargo. Acrylic acid, which undergoes precipitation polymerization to form linear polyacrylic acid, was selected as a rapidly degrading hydrophilic matrix which is expected to dissolve upon insertion into the skin.

Microneedles of three different compositions were applied to ex vivo murine skin by pressing firmly on the back of the patch with the thumb for 30 seconds. The ability of these microneedles to insert into the skin was assessed using a green tissue marking dye, which only stains live cells. The skin samples shown in FIG. 20A-D show that TMPTA microneedles, polyacrylic acid microneedles, and poly(ethylene glycol) microneedles effectively insert into the skin.

Figure 21B:
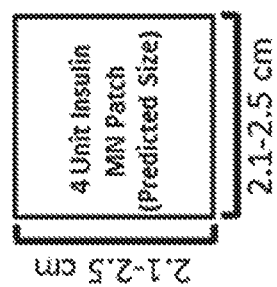
FIG. 21A and FIG. 21B show representative images illustrating that feasibility of using a microneedle patch for insulin delivery. Specifically.
Figure 21A:
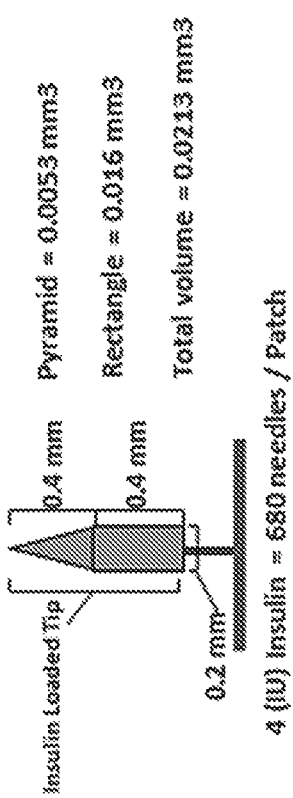

Calculations presented below demonstrate that microneedles are a feasible method for delivery of therapeutic proteins such as insulin. Specifically, for a 4 U dose of insulin, with an arrowhead shape of the given dimensions (FIG. 21A and FIG. 21B), it is estimated that a patch of 4.25 cm²-6.25 cm² would be required, depending on spacing between needles. A square patch measuring 2.1-2.5 cm on each side would provide sufficient volume. The calculations of the patch area are illustrated below:

$$V_{pyramid} = \frac{0.2 \text{ mm} \times 0.2 \text{ mm} \times 0.4 \text{ mm}}{3} = 0.0053 \text{ mm}^3$$

$$V_{rectangle} = 0.2 \text{ mm} \times 0.2 \text{ mm} \times 0.4 \text{ mm} = 0.016 \text{ mm}^3$$

$0.0213 \text{ mm}^3 = 0.0213$ ul volume/Needle Tip 4 (IU) Insulin=145 μg insulin=14.5 μL insulin [10 μg/μL max solubility]

14.5 μL volume/0.0213 μL per needle=680 needles

Wide Needle Spacing (0.1 mm Between Needles)

Area/needle=0.09 mm²×680 needles=61.2 mm²=6.12 cm²

Narrow Needle Spacing (0.05 mm Between Needles)

Area/needle=0.0625 mm²×680 needles=42.5 mm²=4.25 cm²

Of course, alternative sizes, shapes and dimensions of the microneedles and patch hacking could also be used.

Figure 22B:
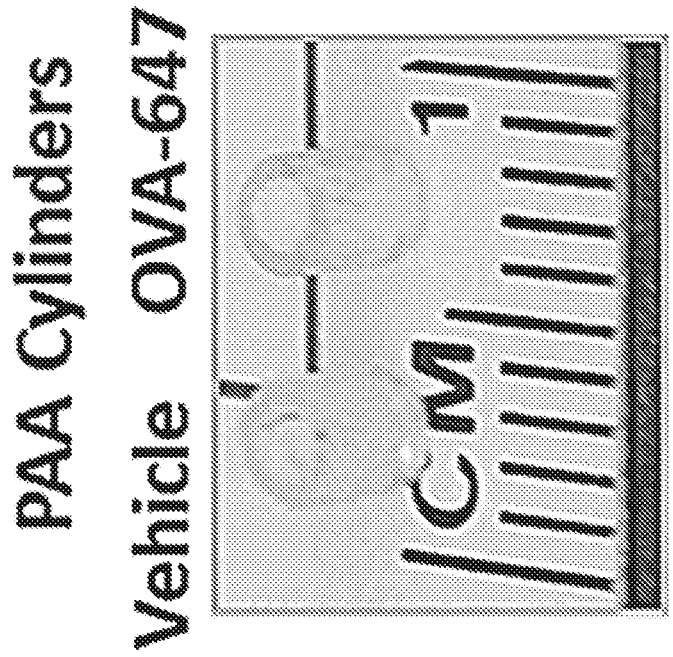
FIG. 22A-C show representative dimensions and images CLIP fabricated poly(acrylic acid) (PAA) cylinders. Specifically.
Figure 22A:
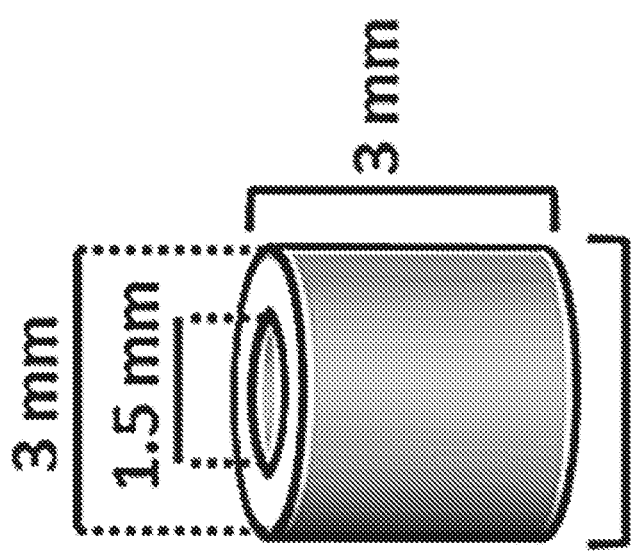
Figure 22C:
Figure 22C:
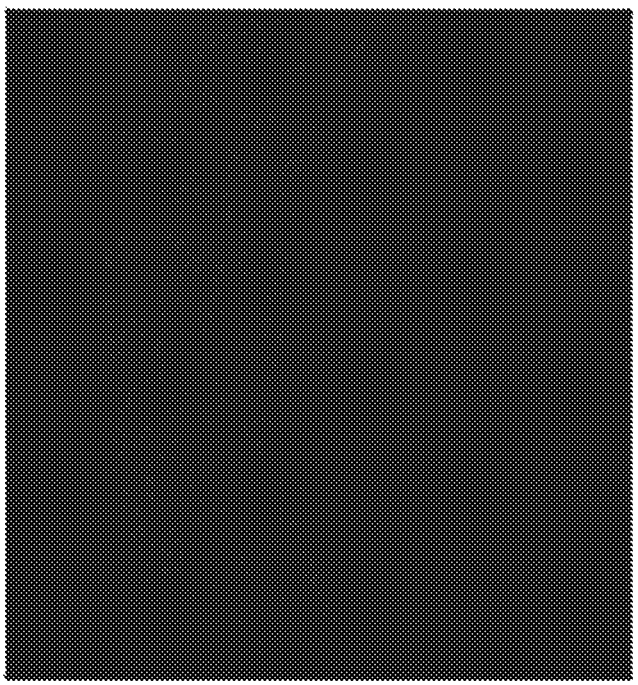

5. Incorporation and Release of Biological Payloads from CLIP Fabricated Biocompatible Material a. Incorporation of Vaccine Antigen into CLIP Fabricated Poly(acrylic acid) (PAA) Materials Fluorescently labeled (Alexa Fluor® 647) model vaccine antigen ovalbumin (referred to as OVA-647) was incorporated into a PAA matrix using CLIP and a resin containing 97.5 wt % acrylic acid monomer (Sigma), 2.3 wt % DPO photo initiator (Sigma), 8.97 wt % water, 0.01 wt % OVA-647 (Invitrogen). Resin of an identical composition, excluding the 0.01 wt % OVA-647, was used as a negative control for OVA-647 incorporation. The shape of the CLIP fabricated test parts was cylindrical with 3 mm diameter×3 mm height, containing a hollowed out center 1.5 mm diameter (FIG. 22A and FIG. 22B). Parts were fabricated using continuous printing on the CLIP7 apparatus (Carbon 3D) with a drawspeed of 100 mm/hr and 8.4 mW/cm2 light intensity. OVA-647 incorporation into CLIP fabricated PAA parts was confirmed using microscopy (FIG. 22C). The OVA-647 and vehicle control PAA cylinders were dissolved in 2 mL of water and the solution was then centrifuged at 20,000×g for 10 minutes to remove any insoluble material and OVA-647 release was measured using a fluorescence plate reader. OVA-647 was readily detected above background florescence levels from vehicle control cylinders (FIG. 23), indicating that OVA-647 is released form PAA cylinders dissolved in water. Without wishing to be bound by theory, these results indicate that vaccine antigens can be incorporated and released form CLIP fabricated biomaterials.

Figure 23:
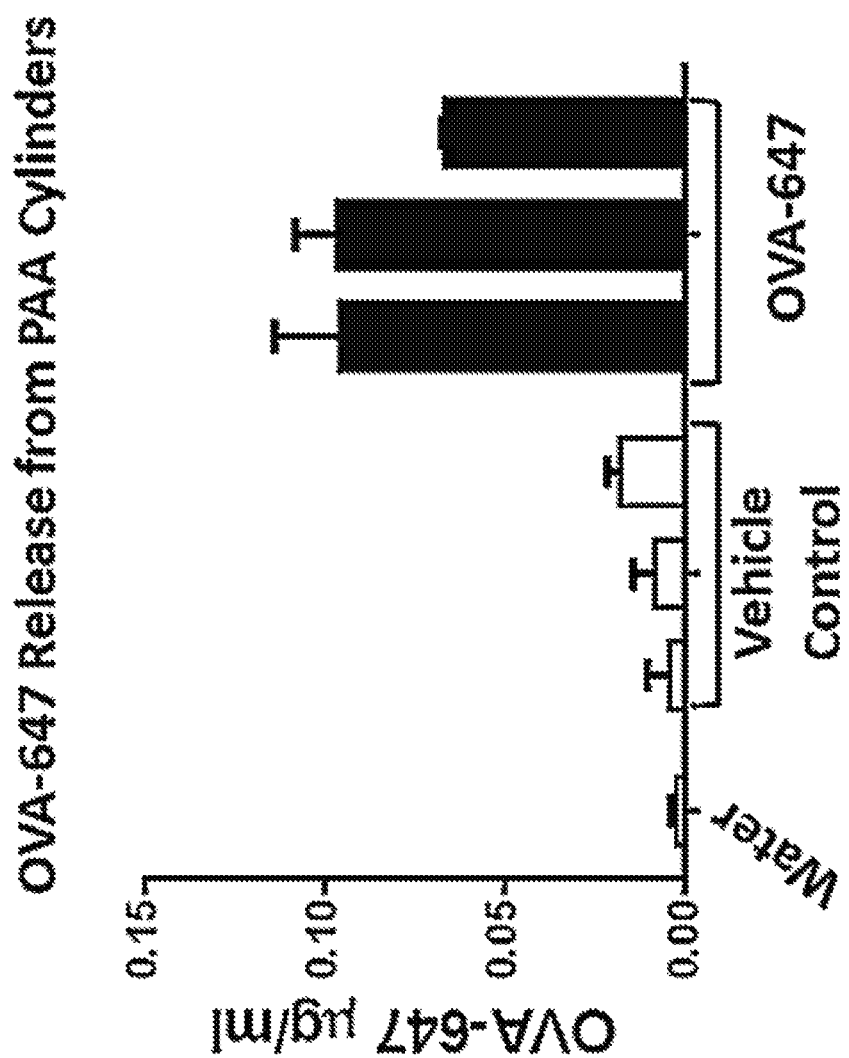
FIG. 23 shows a representative chart illustrating OVA-647 release from CLIP fabricated PAA cylinders.

Referring to FIG. 23, vehicle PAA cylinders (containing 8.97 wt % water) or OVA-647 resin (0.09 wt % OVA-647 in water) were tested. Each bar represents an independent cylinder dissolved in 2 mL of water and the supernatant was measured for OVA-647 fluorescence. Values were normalized to a standard curve of soluble OVA-647. All measurements were performed in duplicate.

b. Incorporation of Active Vaccine Adjuvant into CLIP Fabricated Poly(acrylic acid) (PAA) Material Resiquimod (R-848, Chemdea) was incorporated into test parts with identical dimensions described in FIG. 22A using CLIP and a resin containing 95.42 wt % acrylic acid monomer, 2.44 wt % DPO photo initiator, 2.12 wt % DMSO, 0.02 wt % R-848. Resin of an identical composition, excluding the 0.02 wt % R-848, was used as a negative control for R-848 incorporation and release.

Parts were fabricated using continuous printing on the CLIP7 apparatus (Carbon 3D) with a draw-speed of 100 mm/hr and 8.4 mW/cm2 light intensity. CLIP fabricated PAA parts were washed for 16 hours in acetone to remove residual resin and dried by desiccation. PAA parts were then dissolved in 3 mL of water and the solution was then centrifuged at 20,000×g for 10 minutes to remove any insoluble material and R-848 bioactivity was measured using a cellular based bioassay. Primary murine macrophages were stimulated with supernatant from R-848 containing cylinders or vehicle control cylinders dissolved in phosphate buffered saline (PBS, Sigma) water for 8 hours and an Enzyme Linked immunosorbant Assay (ELISA) method was used to measure inflammatory cytokine IL-6 (ELISA kit from BD Biosciences) release by macrophages, a well-established assay for measuring innate immune responses to adjuvants. R-848 bio-activity was readily detectable in the supernatant fraction of dissolved CLIP fabricated PAA cylinders made with R-848 containing resin (FIG. 24), whereas no activity is measured with the vehicle control cylinders, suggesting that the macrophages were responding specifically to the R-848 and not to the CLIP fabricated PAA polymer itself. Without wishing to be bound by theory, these results indicate that small molecule drugs have the capacity to remain bioactive after incorporation and release from CLIP fabricated biomaterials.

Figure 24:
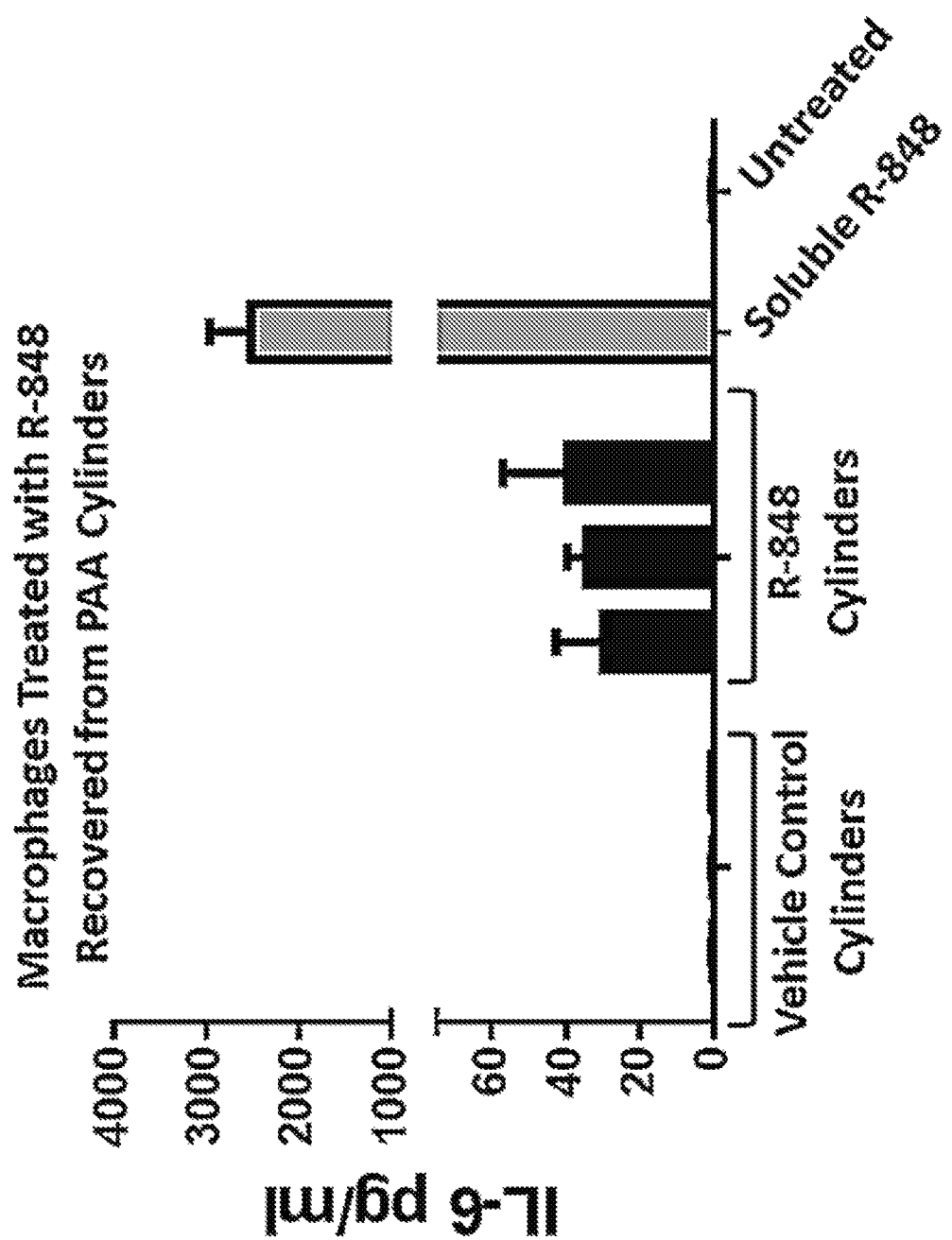
FIG. 24 shows a representative chart illustrating R-848 bio-activity following release from CLIP fabricated PAA cylinders.

Referring to FIG. 24, cylinders were made with resin containing 2.12 wt % DMSO (Vehicle Control) or 0.02 wt % R848 in DMSO (R-848). Cylinders were washed in acetone, desiccated, and dissolved in 3 mL of water and the supernatant was used to stimulate bone marrow macrophages for 8 hours. Each bar represents an independent cylinder. IL-6 secretion was measured in duplicate by ELISA as a readout for R848 activity. Pos. Cntrl, soluble R848 (100 ng/mL).

c. Incorporation of Human Insulin (Insulin) into CLIP Fabricated Poly(acrylic acid) (PAA) Material Insulin (Sigma) was incorporated into test parts with identical dimensions described in FIG. 22A using CLIP and a resin containing 87.1 wt % acrylic acid monomer, 2.52 wt % DPO photo initiator, 10.4 wt % acetic acid, 0.17 wt % human insulin. Resin of an identical composition, excluding the 1.75 wt % insulin, was used as a negative control for insulin incorporation and release. Parts were fabricated using continuous printing on the CLIP7 apparatus (Carbon 3D) with a drawspeed of 100 mm/hr and 14.5 mW/cm2 light intensity. CLIP fabricated PAA parts were dissolved in 2 mL of water and the solution was then centrifuged at 20,000×g for 10 minutes to remove any insoluble material and insulin release was quantified using an sandwich ELIS A method (3A6 anti-insulin coating antibody, 8E2-HRP detection antibody from AbCam) combined with and an insulin standard curve. Insulin was readily detected in dissolved CLIP fabricated PAA cylinders made with insulin containing resin (FIG. 25) with an average of 0.5 unit/mL insulin (1 unit/cylinder), which was close to the theoretical insulin loading levels of 1 unit per cylinder based on PAA cylinder dry weight (20-22 mg). No insulin was detected in the supernatant of dissolved vehicle control cylinders (FIG. 25), validating the specificity of the ELISA-based insulin assay. Without wishing to be bound by theory, these results indicate that small peptide pharmaceuticals have the capacity to be efficiently incorporated and released from CLIP fabricated biomaterials.

Figure 25:
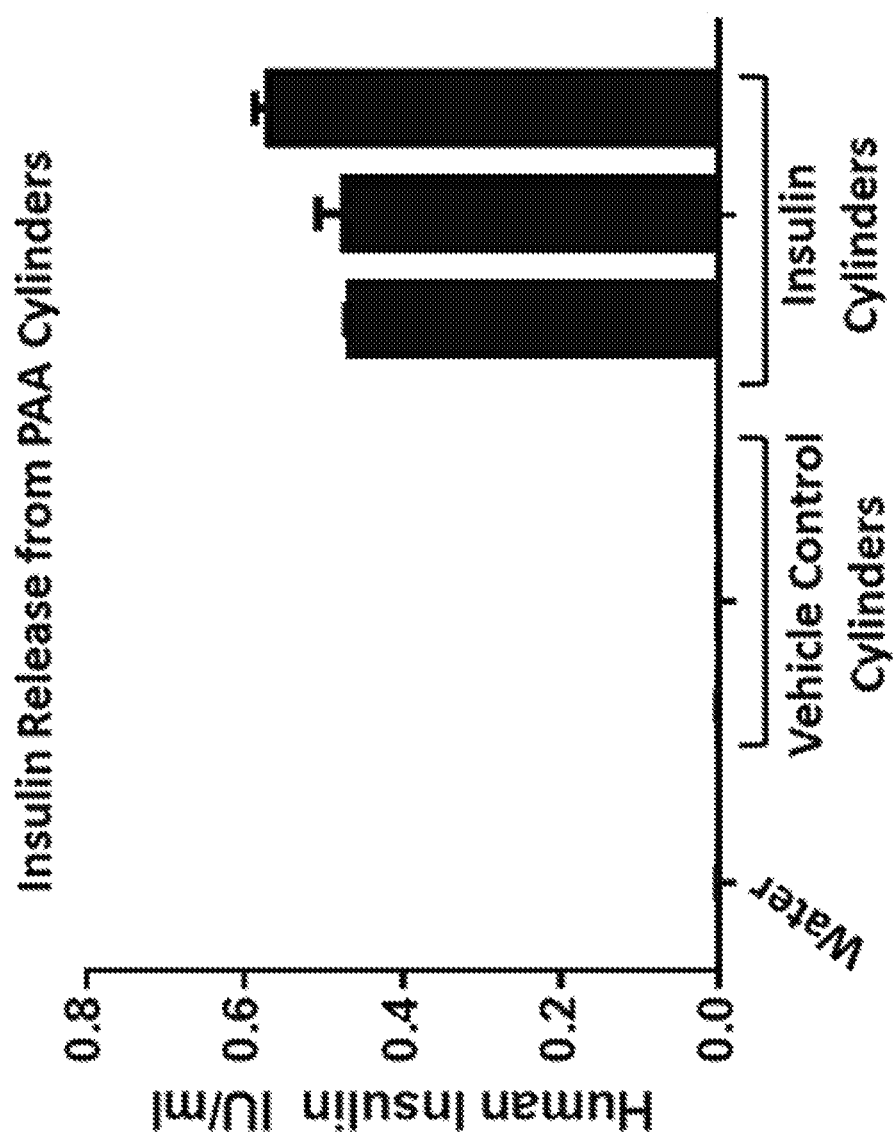
FIG. 25 shows a representative chart illustrating human insulin release from CLIP fabricated. PAA cylinders.

Referring to FIG. 25, PAA cylinders were made with resin containing 10.4 wt % acetic acid (Vehicle Control) or 50 units/mL insulin in acetic acid (Insulin). Cylinders were dissolved in 2 mL of water and the supernatant was tested for insulin release by ELISA with values based on a standard curve.

d. Incorporation and Release of Model Protein from CLIP Microneedles

Figure 26A:
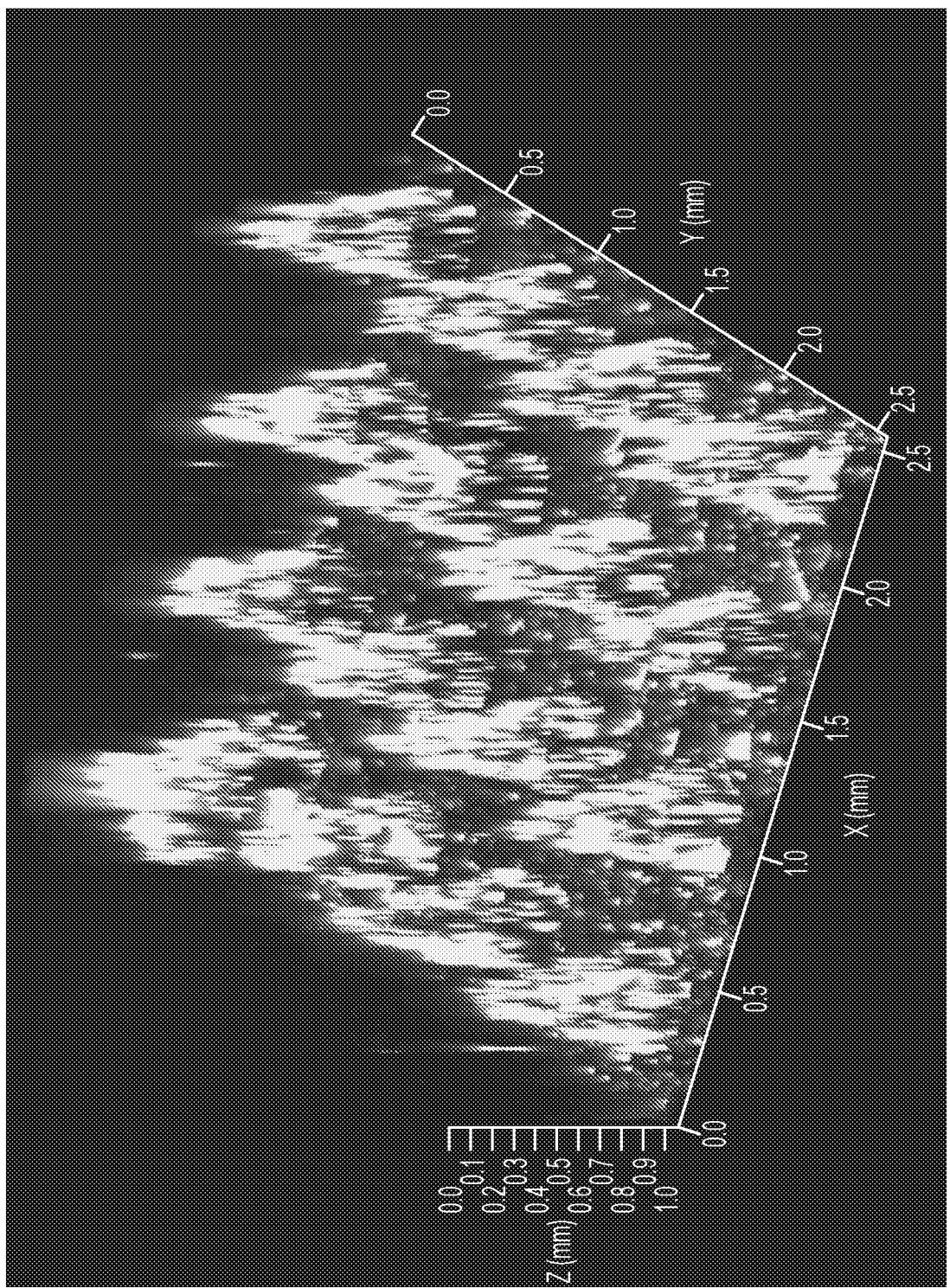
FIG. 26A and FIG. 26B show a representative image (26A) and corresponding data (26B) illustrating FITC-BSA incorporation and release from CLIP PEG microneedles.
Figure 26B:
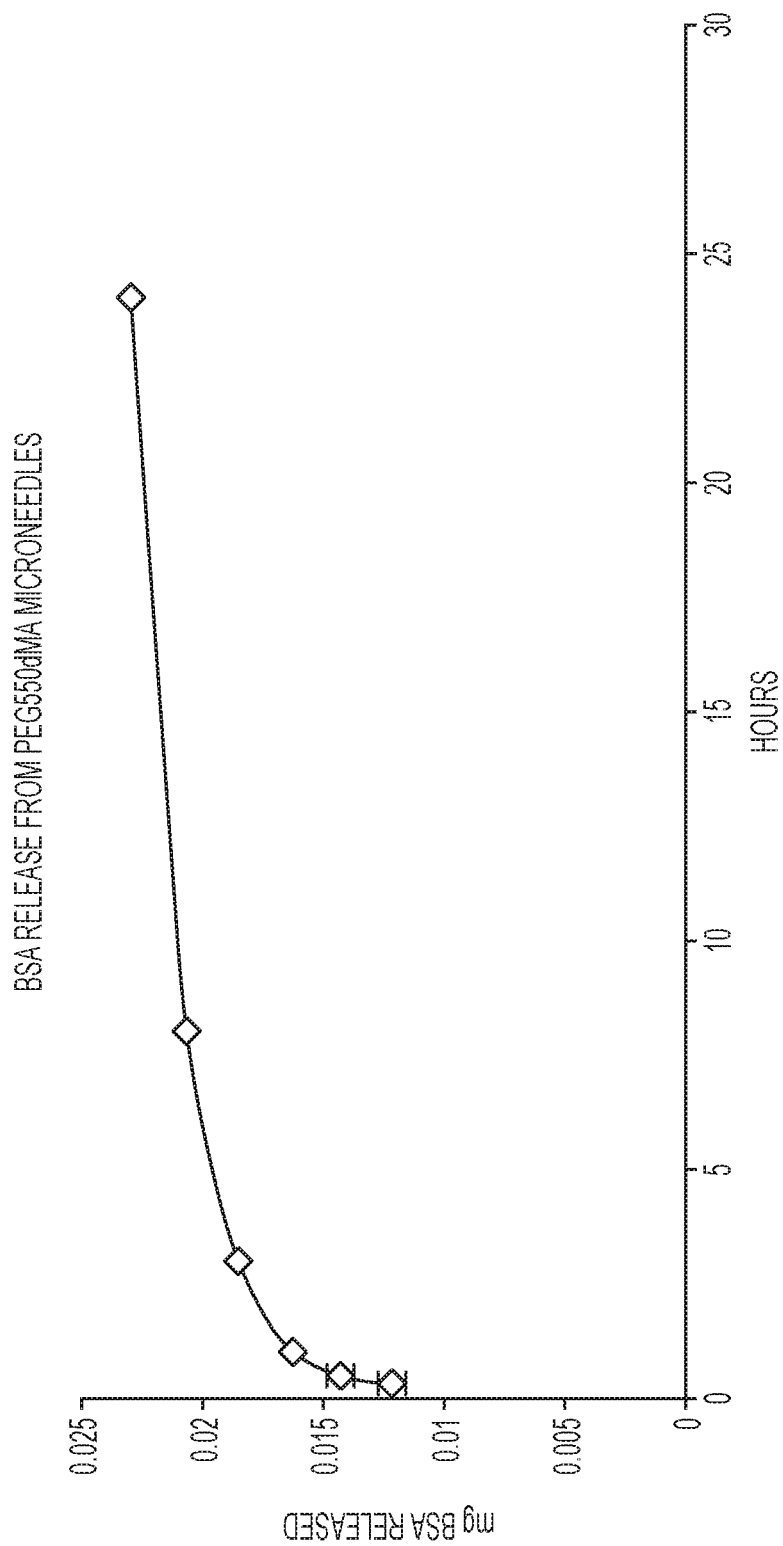

In order to demonstrate that CLIP microneedles are capable of incorporating and releasing cargo, 0.1 wt % FITC-BSA (Invitrogen) was mixed with PEG550-dMa (Sigma) at 97.4 wt % with 2.5 wt % DPO. This resin was used to make PEG microneedles on the CLIP7 apparatus by exposing the resin to light at 1.5 mW/cm$^2$ at 100 mm/hr, FITC-BSA was found to be evenly distributed through the microneedle matrix via confocal microscopy (FIG. 26A). Release of the FITC-BSA from these hydrogel needles in phosphate buffered saline over 24 hours is shown in FIG. 26B. Without wishing to be bound by theory, these results demonstrate that photopolymerizable PEG microneedles fabricated using CLIP are capable of incorporating and releasing proteins.

6. Multi-Component Microneedles Produced by Mid-Production Resin Exchange

Figure 27:
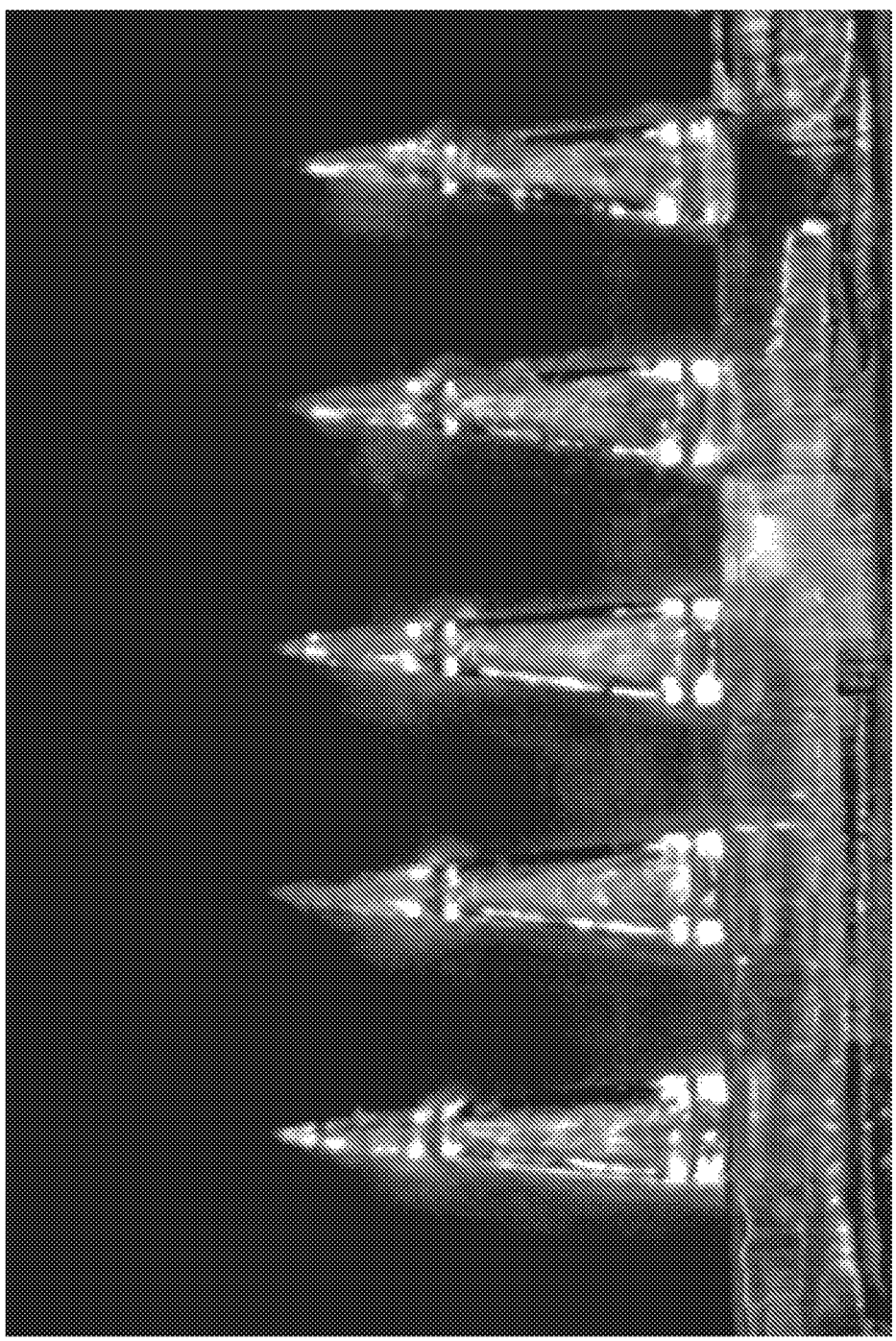
FIG. 27 shows a representative image of tip-loaded microneedles produced using the mid-production resin exchange method.

An example of a multi-component microneedle produced using CLIP is given in FIG. 27. In this example, the microneedle base is composed of trimethylpropylol triacrylate whereas the tips are composed of trimethylpropylol triacrylate plus rhodamine.

7. Undercut Microneedles

Figure 28B:
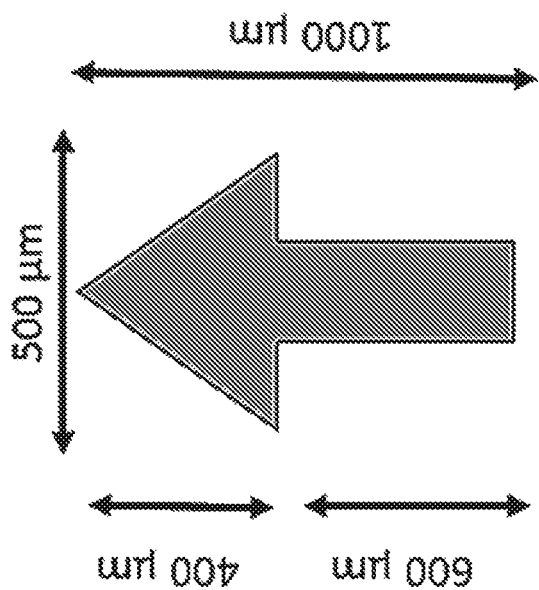
FIG. 28A-C show representative images of undercut CLIP microneedles. Specifically, TMPTA arrowhead microneedles produced using CLIP (28A), the dimensions of the arrowhead microneedles in 28A (28B), and other examples of undercut structures (28C).
Figure 28A:
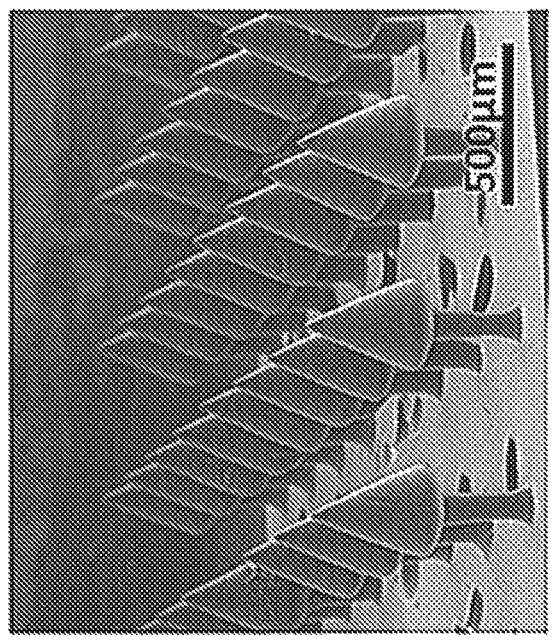
Figure 28C:
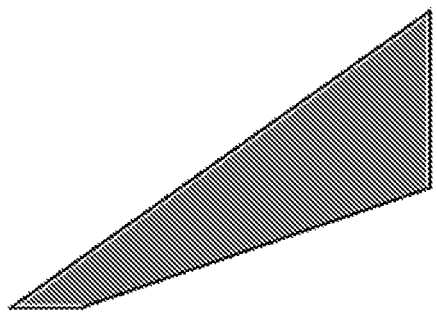
Figure 28C:
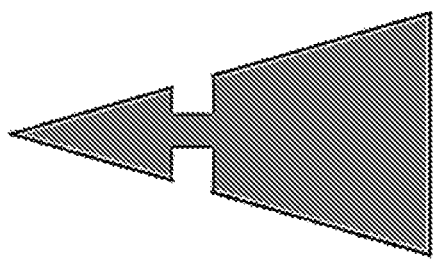
Figure 28C:
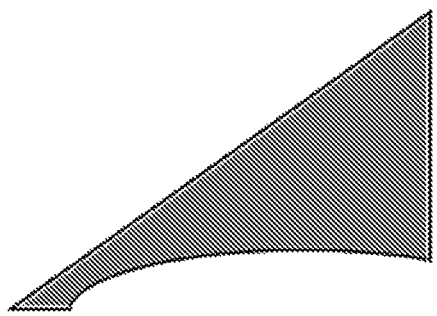
Figure 28C:
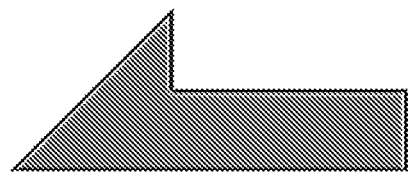

Some arrowhead microneedles produced using CLIP are shown in FIG. 28A. These microneedles were fabricated from a mixture of TMPTA and 2.5 wt % DPO plus 0.1 wt % Mayzo BLS1326 ultraviolet light absorber with 5.4 mW/cm$^2$ of light at 41 mm/hr. Microneedle dimensions are given in FIG. 28B, The specific dimensions may be altered to optimize microneedle efficacy. Without wishing to be bound by theory, it is hypothesized that these microneedles will insert more deeply and more consistently into the skin than a control microneedle, which contains no undercut. A variety of other undercut microneedle shapes that could be produced using CLIP are shown in FIG. 28C. The mechanical stability of such shapes as compared to their efficacy in reducing microneedle relaxation out of the skin is an area of potential study which would allow for down-selection of ideal microneedle shapes.

8. Tiered Microneedles

Figure 29:
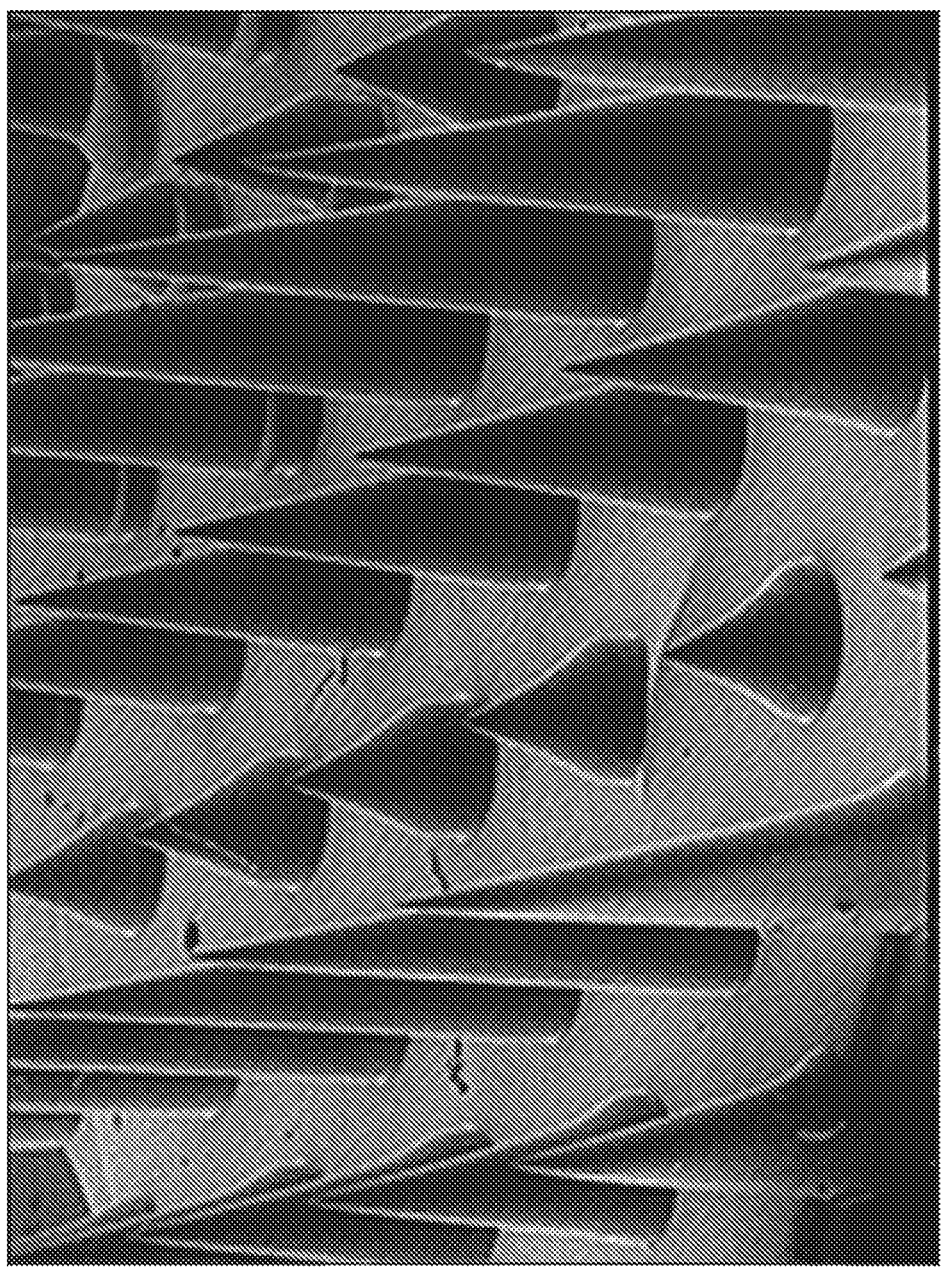
FIG. 29 shows a representative image of a TMPTA tiered microneedle array.

A tiered microneedle array was generated using CLIP technology (FIG. 29). This array of TMPTA microneedles was fabricated using equivalent techniques to those used in FIG. 19A-D. Conical microneedles measure 300 μm in diameter and 300, 600, and 900 μm in height.

Figure 30:
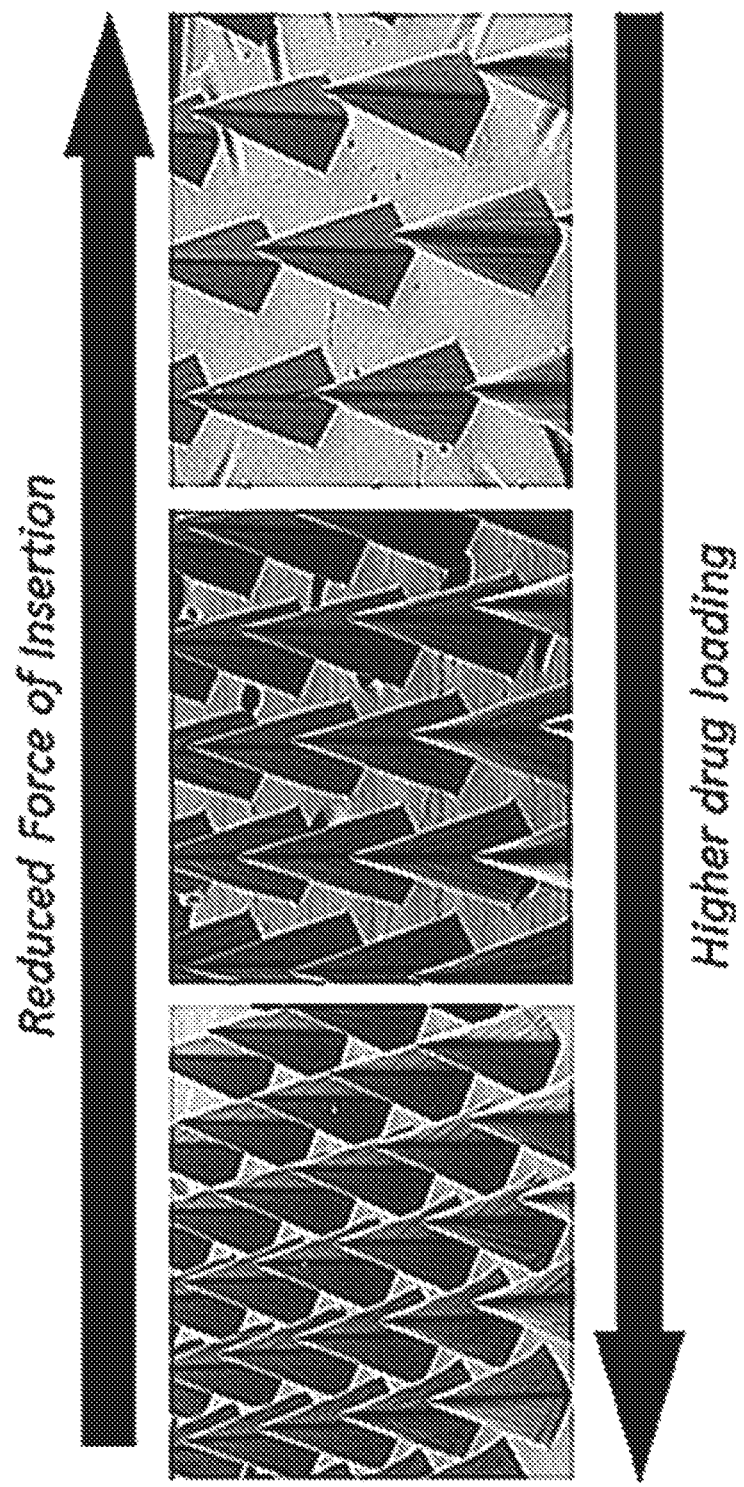
FIG. 30 shows a representative image of illustrating that higher drug loading may result in higher insertion forces.

Note that in addition to decreasing insertion forces, this technique also circumvents the optimization problem that exists, wherein increasing the available volume for drug loading in a traditional array typically increases the force required for insertion (FIG. 30). By using a tiered microneedle array, a larger volume of therapeutic can be delivered using an equivalent force (Table 4). These calculations assume that all tiers have the same number of microneedles and that the base width of all microneedle heights is equivalent.

TABLE 4

| # of Tiers | Force Required to Insert Equivalent # of MNs | # of MNs inserted with force F | MN Heights (μM) | Volume of Cargo inserted with force F |
|---|---|---|---|---|
| 1 | F | X | 1000 | V |
| 2 | F/2 | 2X | 1000, 900 | 1.9 V |
| 3 | F/3 | 3X | 1000, 900, 800 | 2.7 V |
| 4 | F/4 | 4X | 1000, 900, 800, 700 | 3.4 V |
| 5 | F/5 | 5X | 1000, 900, 800, 700, 600 | 4 V |
| 6 | F/6 | 6X | 1000, 900, 800, 700, 600, 500 | 4.5 V |

9. Microneedles with Curved or Discontinuous Sidewall Profiles

Examples of microneedles fabricated with a curved and discontinuous sidewall profile are shown in FIG. 5B. These microneedles, which measure 1000 μm in height and 500 μm in width, were fabricated using the CLIP Mini Apparatus (see Table 1) at 100 mm/hr using 5.9 mW/cm$^2$ of light. In various aspects, it may be desirable to fabricate such microneedles out of two distinct compositions, such as, for example, a strong material at the tip, chosen for its material properties, over a soft base, chosen for its chemical or biological properties, as shown in FIG. 5C. A number of different specific conformations could be chosen, such as those depicted in FIG. 5D.

10. Fabrication of Microneedles with Water Soluble Chemical Perforations

Figures 31A, 31B:
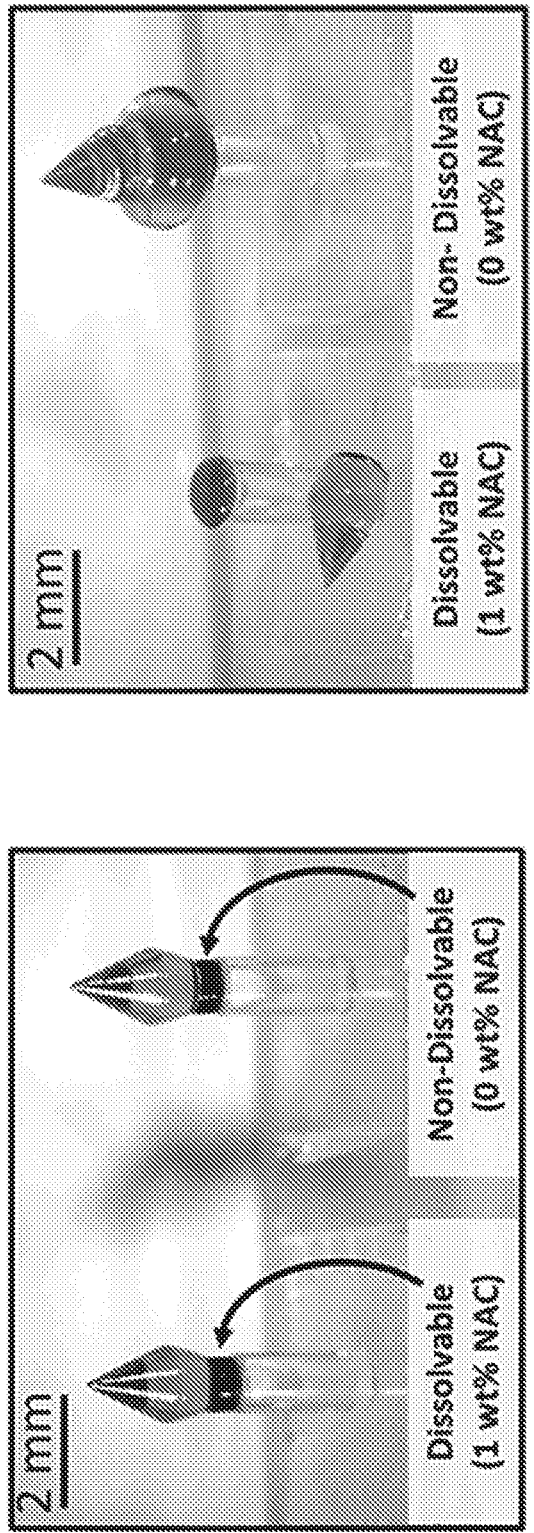
FIG. 31A and FIG. 31B show representative images illustrating Tri-material microneedles with dissolvable (left) and non-dissolvable (right) perforations made using CLIP technology prior to exposure to water (31A) and following submersion in water for 12 minutes (31B).

MNs were made using a computer-aided design (CAD) file consisting of a needle patch backing, a needle shaft, and an undercut arrowhead needle tip. The CAD file was converted to an SIL and sliced into 1 μm cross sections using the Slic3r software to create an SVG file. The backing and lower portion of the shaft (slices 1-2750) were printed continuously using TMPTA+2 wt % TPO at a speed of 100 mm/hour and light intensity of 5.8 mW/cm$^2$. The part was then washed of any residual resin using isopropanol while affixed to the build platform. The resin in the reservoir was exchanged for a water soluble resin consisting of acrylic acid monomer+2 wt % DPO+1 wt % N-acetyl cysteine (NAC)+4.2 wt % water. The NAC serves as a chain transfer agent to reduce the average molecular weight of PAA chains to form a water soluble perforation. Layers 2751-3250 were continuously printed using the water soluble resin at a speed of 25 mm/hr with a light intensity of 9 mW/cm$^2$. The part was then washed of any residual resin using isopropanol while still affixed to the build platform. The resin in the reservoir was exchanged for TMPTA+2 wt % TPO+0.01 wt % Rhodamine, which was used to continuously print the undercut arrow head structure (layers 3251-5368) at a speed of 100 mm/hour and light intensity of 5.8 mW/cm$^2$. The part was then rinsed a final time with isopropanol and post-cured for 90 seconds under a mercury lamp in the presence of nitrogen gas. The tri-material CLIP fabricated needle containing a dissolvable perforation can be seen (FIG. 31A, left). A control needle was made using an identical process a loosely crosslinked acrylic acid resin containing a small amount of the crosslinker TMPTA, which rendered the PAA water insoluble. The base and lower shaft are made of TMPTA+2 wt % TPO, the dissolvable layer is made of poly acrylic acid (PAA)+1 wt % NAC. The non-dissolvable layer in the control needle is comprised of PAA with 1 wt % water as a control. The tips for both needles are made of non-dissolvable TMPTA+0.01 wt % rhodamine to serve as a drug surrogate.

Both needles were submerged in water for 12 min., at which time the dissolvable perforation dissolved and gave a clean separation of the needle arrow head from the Wise/shaft (FIG. 31B, left). In contrast the non-dissolvable perforation swelled and maintained continuity between the needle shaft and arrowhead tip (FIG. 31B, right).

The above method for CLIP fabrication of a needle structure containing a dissolvable perforation utilizes the FDA approved molecule N-Acetyl-Cysteine as a chain transfer agent to reduce the molecular weight of PAA chains and facilitate solubility. Likewise, other chain transfer agents, including other thiol containing compounds (e.g. N-acetyl-cysteine, cysteine, DTT, 2-ME) and non-thiol containing compounds (e.g. isopropanol, ethanol) could also be added to resins for the purpose of controlling polymer molecular weight and improve water solubility of parts fabricated using CLIP technology.

Figure 32:
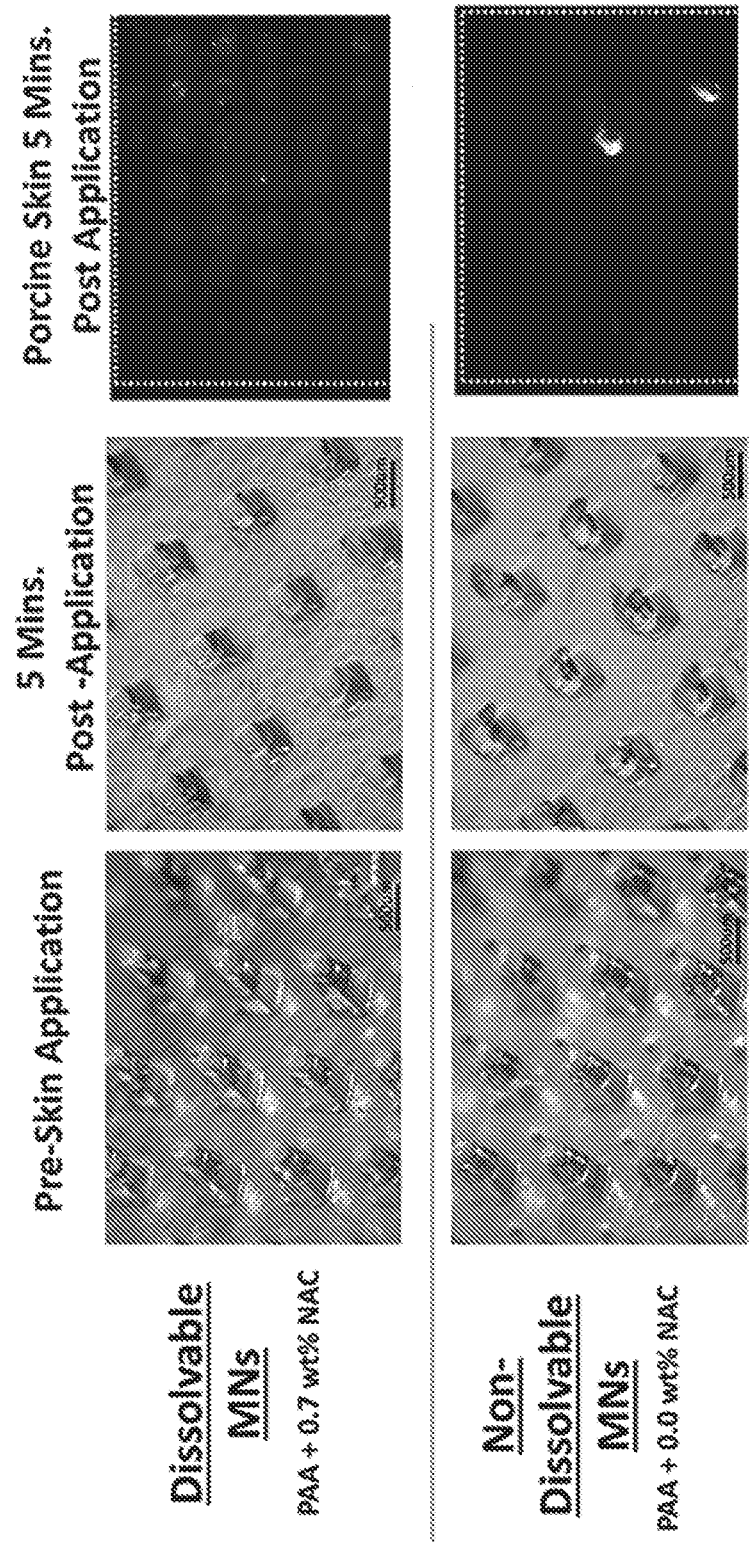
FIG. 32 shows representative images of microneedles with dissolving (top) and non-dissolving (bottom) tips containing rhodamine prior to skin application (left) and following 5 minute application to porcine skin (middle). Rhodamine fluorescence in porcine skin imaged following microneedle patch application is also shown (right).

11. Fabrication of Dual Material Needles with Dissolvable Tips and Non-Dissolvable Backing CAD software was used to generate an STL file of a microneedle patch containing 81 pyramidal needles with dimensions of 1.2 mm in height and an aspect ratio of 3:1. The STL version of this file was sliced into 1 μm cross sections using the Slic3r software and uploaded into the CLIP control panel as an SVG file. Slices 1-900 encoded the 500 μm base and 400 μm of the 1.2 mm tall needles, and were printed continuously using a non-dissolvable hydrogel resin (poly(ethylene glycol)-diacrylate+2 wt % TPO) at 60 mm/hr with a light intensity of 2 mW/cm$^2$. The part was then washed of any residual resin using isopropanol and was post-cured for 60 seconds under a mercury lamp in the presence of nitrogen gas. The resin in the reservoir was exchanged for an acrylic acid resin containing 0.7 wt % NAC+3 wt % H2O+2 wt % DPO+0.01 wt % Rhodamine (as drug surrogate). This resin was used to make the dissolvable microneedle tips by showing frames 801-1674 of the sliced STL file with light intensity of 12 mW/cm$^2$ at 25 mm/hr. The needle patch was washed thoroughly with IPA and then post-cured for 90 seconds under a mercury lamp in the presence of nitrogen gas. The final microneedle patch is shown in FIG. 32. A control microneedle patch was made using an identical process with the omission of NAC from the acrylic acid resin, which renders the tip water insoluble (FIG. 32).

These needles were applied to porcine skin ex vivo using even pressure applied by gentle force with a 200 gram weight for 10 seconds. The weight remained in place on the skin for five minutes and then the patch was removed and imaged. The tips on the needle patch containing 0.7 wt % NAC dissolved completely after application to the skin and the rhodamine dye is visible in the porcine skin in a pattern that reflects the needle arrangement. In contrast, the control needles lacking NAC swelled and bent after application to the skin, but they did not dissolve. There was little evidence of rhodamine deposition by the control needles in the porcine skin.

The foregoing is illustrative of the present invention, and is not to be construed as limiting thereof. The invention is defined by the following claims, with equivalents of the claims to be included therein.

It will be apparent to those skilled in the art that various modifications and variations can be made in the present invention without departing from the scope or spirit of the invention. Other aspects of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. A method of making a microneedle device, the method comprising the steps of:
    (a) providing a build elevator and an optically transparent build surface, wherein the build elevator and the build surface together define a build region there between, wherein the build surface is permeable to a polymerization inhibitor, and wherein the build surface is in fluid communication with a source of the polymerization inhibitor;
    (b) filling the build region with a polymerizable liquid;
    (c) irradiating the build region through the build surface to produce a solid polymerized region coinciding with a cross-section of the device in the build region;
    (d) forming or maintaining a liquid film release layer between the solid polymerized region and the build surface by supplying the polymerization inhibitor thereto, wherein the liquid film release layer comprises the polymerizable liquid, and wherein the polymerization of the polymerizable liquid is inhibited by the polymerization inhibitor at the liquid film release layer; and
    (e) advancing the build elevator away from the build surface to create a subsequent build region between the solid polymerized region and the build surface while concurrently filling the subsequent build region with the polymerizable liquid,
    wherein steps (c)-(e) are repeated so as to form the device to comprise:
    (f) a backing; and
    (g) a plurality of biocompatible microneedles projecting from the backing, wherein the microneedles comprise one or more of:
        (i) a curved, discontinuous, undercut, or perforated sidewall;
        (ii) a sidewall comprising a breakable support; and
        (iii) a cross-section that is non-circular and non-polygonal, and/or wherein the microneedles are tiered in addition or in the alternative to (i)-(iii), and
    wherein the polymerizable liquid is exchanged with another polymerizable liquid of different polymerizable material prior to at least one instance of said repeating so as to produce multi-component microneedles.

2. The method of claim 1, wherein said irradiating is via actinic radiation.

3. The method of claim 1, wherein said advancing comprises moving the build elevator vertically away from the build surface.

4. The method of claim 1, wherein the microneedle device is formed in less than about 30 minutes.

5. The method of claim 1, wherein the microneedles comprise a curved, discontinuous, undercut, or perforated sidewall.

6. The method of claim 5, wherein the microneedles comprise a sidewall comprising a breakable support.

7. The method of claim 5, wherein the microneedles are tiered.

8. The method of claim 1, wherein the microneedles comprise an undercut sidewall.

9. The method of claim 8, wherein the microneedles comprise a sidewall comprising a breakable support.

10. The method of claim 8, wherein the microneedles are tiered.

11. The method of claim 1, wherein the microneedles comprise a sidewall comprising a breakable support.

12. The method of claim 11, wherein the microneedles are tiered.

13. The method of claim 1, wherein the microneedles comprise a cross-section that is non-circular and non-polygonal.

14. The method of claim 1, wherein the microneedles are tiered.

15. The method of claim 1, wherein the microneedles are hollow or porous.

16. The method of claim 15, wherein the microneedles are hollow.

17. The method of claim 1, wherein the microneedles have an average diameter of from 5 to 1,000 micrometers, an average length of from 5 to 1,500 micrometers, and an average distance from one another of from 5 to 1,000 micrometers.

* * * * *